US010064856B2

(12) United States Patent
Bosse et al.

(10) Patent No.: US 10,064,856 B2
(45) Date of Patent: *Sep. 4, 2018

(54) PHARMACEUTICAL COMPOSITIONS

(71) Applicant: LOCL PHARMA, INC., Las Vegas, NV (US)

(72) Inventors: Paul Bosse, Jupiter, FL (US); John Ameling, Jupiter, FL (US); Bernard Schachtel, Jupiter, FL (US); Ray Takigiku, Loveland, OH (US)

(73) Assignee: LOCAL PHARMA, INC., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/683,635

(22) Filed: Aug. 22, 2017

(65) Prior Publication Data

US 2017/0348303 A1 Dec. 7, 2017

Related U.S. Application Data

(63) Continuation of application No. 14/930,496, filed on Nov. 2, 2015, now Pat. No. 9,789,105, which is a continuation of application No. 14/036,946, filed on Sep. 25, 2013, now Pat. No. 9,226,901, which is a continuation of application No. 13/347,552, filed on Jan. 10, 2012, now Pat. No. 9,198,867, which is a continuation of application No. 12/351,704, filed on Jan. 9, 2009, now Pat. No. 8,124,126.

(60) Provisional application No. 61/060,758, filed on Jun. 11, 2008, provisional application No. 61/043,037, filed on Apr. 7, 2008, provisional application No. 61/020,139, filed on Jan. 9, 2008.

(51) Int. Cl.
| | |
|---|---|
| *A61K 31/485* | (2006.01) |
| *A61K 9/20* | (2006.01) |
| *A61K 45/06* | (2006.01) |
| *A61K 31/404* | (2006.01) |
| *A61K 31/403* | (2006.01) |
| *A61K 31/454* | (2006.01) |
| *A61K 31/422* | (2006.01) |
| *A61K 31/4196* | (2006.01) |
| *A61K 31/522* | (2006.01) |
| *A61K 31/515* | (2006.01) |
| *A61K 31/24* | (2006.01) |
| *A61K 9/48* | (2006.01) |
| *A61K 31/5415* | (2006.01) |
| *A61K 31/437* | (2006.01) |
| *A61K 31/167* | (2006.01) |
| *A61K 31/165* | (2006.01) |
| *A61K 9/24* | (2006.01) |
| *A61K 47/36* | (2006.01) |
| *A61K 9/16* | (2006.01) |
| *A61K 9/00* | (2006.01) |

(52) U.S. Cl.
CPC ........... *A61K 31/485* (2013.01); *A61K 9/209* (2013.01); *A61K 9/2013* (2013.01); *A61K 9/2027* (2013.01); *A61K 9/2054* (2013.01); *A61K 9/4808* (2013.01); *A61K 31/165* (2013.01); *A61K 31/167* (2013.01); *A61K 31/24* (2013.01); *A61K 31/403* (2013.01); *A61K 31/404* (2013.01); *A61K 31/4196* (2013.01); *A61K 31/422* (2013.01); *A61K 31/437* (2013.01); *A61K 31/454* (2013.01); *A61K 31/515* (2013.01); *A61K 31/522* (2013.01); *A61K 31/5415* (2013.01); *A61K 45/06* (2013.01); *A61K 9/0024* (2013.01); *A61K 9/0056* (2013.01); *A61K 9/1694* (2013.01); *A61K 9/2086* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 3,048,526 | A | 8/1962 | Boswell |
| 3,108,046 | A | 10/1963 | Harbit |
| 3,536,809 | A | 10/1970 | Norman |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,113,866 | A | 9/1978 | Lednicer |
| 4,265,875 | A | 5/1981 | Byrne et al. |
| 4,478,822 | A | 10/1984 | Haslam et al. |
| 4,532,126 | A | 7/1985 | Ebert et al. |
| 4,588,580 | A | 5/1986 | Gale et al. |
| 4,624,665 | A | 11/1986 | Nuwayser |
| 4,625,494 | A | 12/1986 | Iwatschenko et al. |
| 4,626,539 | A | 12/1986 | Aungst et al. |

(Continued)

FOREIGN PATENT DOCUMENTS

| | | |
|---|---|---|
| CA | 2262267 A1 | 8/1999 |
| DE | 102005013726 A1 | 9/2006 |

(Continued)

OTHER PUBLICATIONS

US 8,975,271, 03/2015, Oshlack et al. (withdrawn)
Alexander, et al. Comparison of ondansetron and droperidol in reducing postoperative nausea and vomiting associated with patient-controlled analgesia. Anaesthesia. Dec. 1995;50(12):1086-8.
Amdipharm Plc. Opioid-induced nausea and vomiting. Web Site by Nexus Internet Solutions Ltd. Apr. 2004.
Amo, et al. Subchronic and chronic effects of feeding of large amounts of acetaminophen in B6C3F1 mice. Jap J Hyg. 40:567-574, 1985.

(Continued)

*Primary Examiner* — Susan T Tran
(74) *Attorney, Agent, or Firm* — Wilson Sonsini Goodrich & Rosati

(57) ABSTRACT

Methods and compositions are provided which comprise effective amounts of an analgesic to treat a subject, including reducing or eliminating an adverse effect associated with the analgesic.

7 Claims, 5 Drawing Sheets

(56) References Cited

U.S. PATENT DOCUMENTS

| | | |
|---|---|---|
| 4,671,953 A | 6/1987 | Stanley et al. |
| 4,685,911 A | 8/1987 | Konno et al. |
| 4,717,713 A | 1/1988 | Zatz et al. |
| 4,786,505 A | 11/1988 | Lovgren et al. |
| 4,788,055 A | 11/1988 | Fischer et al. |
| 4,800,083 A | 1/1989 | Hom et al. |
| 4,820,522 A | 4/1989 | Radebaugh et al. |
| 4,834,978 A | 5/1989 | Nuwayser |
| 4,853,211 A | 8/1989 | Kurobe et al. |
| 4,871,353 A | 10/1989 | Thomsen |
| 4,904,479 A | 2/1990 | Illum |
| 4,906,463 A | 3/1990 | Cleary et al. |
| 4,919,939 A | 4/1990 | Baker |
| 4,925,444 A | 5/1990 | Orkin et al. |
| 4,935,243 A | 6/1990 | Borkan et al. |
| 4,950,484 A | 8/1990 | Olthoff et al. |
| 5,013,726 A | 5/1991 | Ivy et al. |
| 5,055,461 A | 10/1991 | Kelleher et al. |
| 5,059,595 A | 10/1991 | Le Grazie |
| 5,073,543 A | 12/1991 | Marshall et al. |
| 5,120,548 A | 6/1992 | McClelland et al. |
| 5,266,331 A | 11/1993 | Oshlack et al. |
| 5,298,520 A | 3/1994 | Baker et al. |
| 5,354,556 A | 10/1994 | Sparks et al. |
| 5,373,022 A | 12/1994 | Fawzi et al. |
| 5,376,672 A | 12/1994 | Pilgrim |
| 5,393,773 A | 2/1995 | Craig et al. |
| 5,425,950 A | 6/1995 | Dandiker et al. |
| 5,445,829 A | 8/1995 | Paradissis et al. |
| 5,464,864 A | 11/1995 | King et al. |
| 5,468,504 A | 11/1995 | Schaeffer |
| 5,478,577 A | 12/1995 | Sackler et al. |
| 5,484,406 A | 1/1996 | Wong et al. |
| 5,508,042 A | 4/1996 | Oshlack et al. |
| 5,536,249 A | 7/1996 | Castellano et al. |
| 5,549,912 A | 8/1996 | Oshlack et al. |
| 5,554,639 A | 9/1996 | Craig et al. |
| 5,585,115 A | 12/1996 | Sherwood et al. |
| 5,591,767 A | 1/1997 | Mohr et al. |
| 5,602,162 A | 2/1997 | Baker et al. |
| 5,610,184 A | 3/1997 | Shahinian, Jr. |
| 5,629,333 A | 5/1997 | Young |
| 5,635,204 A | 6/1997 | Gevirtz et al. |
| 5,637,611 A | 6/1997 | King et al. |
| 5,639,476 A | 6/1997 | Oshlack et al. |
| 5,656,295 A | 8/1997 | Oshlack et al. |
| 5,674,533 A | 10/1997 | Santus et al. |
| 5,705,506 A | 1/1998 | Merlet et al. |
| 5,705,520 A | 1/1998 | Craig et al. |
| 5,712,302 A | 1/1998 | Young |
| 5,733,556 A | 3/1998 | Schrier et al. |
| 5,738,874 A | 4/1998 | Conte et al. |
| 5,741,510 A | 4/1998 | Rolf et al. |
| 5,827,852 A | 10/1998 | Russell et al. |
| 5,827,871 A | 10/1998 | King et al. |
| 5,837,284 A | 11/1998 | Mehta et al. |
| 5,840,731 A | 11/1998 | Mayer et al. |
| 5,854,270 A | 12/1998 | Gambhir |
| 5,863,559 A | 1/1999 | Phillips et al. |
| 5,863,922 A | 1/1999 | Mayer et al. |
| 5,866,161 A | 2/1999 | Childers et al. |
| 5,871,776 A | 2/1999 | Mehta |
| 5,891,885 A | 4/1999 | Caruso |
| 5,895,663 A | 4/1999 | Irwin et al. |
| 5,902,632 A | 5/1999 | Mehta |
| 5,919,479 A | 7/1999 | Zhang et al. |
| 5,929,059 A | 7/1999 | Sanger et al. |
| 5,954,700 A | 9/1999 | Kovelman |
| 5,962,494 A | 10/1999 | Young |
| 5,968,551 A | 10/1999 | Oshlack et al. |
| 6,020,001 A | 2/2000 | Phillips et al. |
| 6,063,802 A | 5/2000 | Winterborn |
| 6,146,361 A | 11/2000 | DiBiasi et al. |
| 6,160,020 A | 12/2000 | Ohannesian et al. |
| 6,228,398 B1 | 5/2001 | Devane et al. |
| 6,228,863 B1 | 5/2001 | Palermo et al. |
| 6,255,502 B1 | 7/2001 | Penkler et al. |
| 6,258,380 B1 | 7/2001 | Overholt |
| 6,261,595 B1 | 7/2001 | Stanley et al. |
| 6,287,600 B1 | 9/2001 | Ouali et al. |
| 6,303,142 B1 | 10/2001 | Zhang et al. |
| 6,335,033 B1 | 1/2002 | Oshlack et al. |
| 6,341,387 B1 | 1/2002 | Zars |
| 6,348,216 B1 | 2/2002 | Kushla et al. |
| 6,368,627 B1 | 4/2002 | Phillips et al. |
| 6,372,254 B1 | 4/2002 | Ting et al. |
| 6,376,550 B1 | 4/2002 | Raber et al. |
| 6,465,006 B1 | 10/2002 | Zhang et al. |
| 6,469,227 B1 | 10/2002 | Cooke et al. |
| 6,475,494 B2 | 11/2002 | Kaiko et al. |
| 6,482,435 B1 | 11/2002 | Stratton et al. |
| 6,491,945 B1 | 12/2002 | Childers et al. |
| 6,572,871 B1 | 6/2003 | Church et al. |
| 6,572,885 B2 | 6/2003 | Oshlack et al. |
| 6,599,531 B2 | 7/2003 | Kushla et al. |
| 6,613,350 B1 | 9/2003 | Zhang et al. |
| 6,649,183 B2 | 11/2003 | Rubin et al. |
| 6,699,502 B1 | 3/2004 | Fanara et al. |
| 6,730,325 B2 | 5/2004 | Devane et al. |
| 6,733,783 B2 | 5/2004 | Oshlack et al. |
| 6,756,053 B2 | 6/2004 | Zhang et al. |
| 6,756,056 B2 | 6/2004 | Rubin |
| 6,780,426 B2 | 8/2004 | Zhang et al. |
| 6,827,946 B2 | 12/2004 | Hirsh |
| 6,855,332 B2 | 2/2005 | Gizurarson et al. |
| 6,902,742 B2 | 6/2005 | Devane et al. |
| 6,913,768 B2 | 7/2005 | Couch et al. |
| 6,923,988 B2 | 8/2005 | Patel et al. |
| 6,976,647 B2 | 12/2005 | Reed et al. |
| 7,029,698 B2 | 4/2006 | Waranis et al. |
| RE39,221 E | 8/2006 | Raffa et al. |
| 7,094,228 B2 | 8/2006 | Zhang et al. |
| 7,172,767 B2 | 2/2007 | Kaiko et al. |
| 7,201,920 B2 | 4/2007 | Kumar et al. |
| 7,214,385 B2 | 5/2007 | Gruber |
| 7,214,711 B2 | 5/2007 | Hochman |
| 7,332,183 B2 | 2/2008 | Plachetka et al. |
| 7,342,028 B2 | 3/2008 | Hagan et al. |
| 7,514,100 B2 | 4/2009 | Oshlack et al. |
| 7,585,493 B2 | 9/2009 | Hale et al. |
| 7,585,520 B2 | 9/2009 | Hirsh et al. |
| 7,666,337 B2 | 2/2010 | Yang et al. |
| 7,744,916 B2 | 6/2010 | Pauletti et al. |
| 7,794,750 B2 | 9/2010 | Naringrekar et al. |
| 7,863,296 B2 | 1/2011 | Weiner et al. |
| 7,943,174 B2 | 5/2011 | Oshlack et al. |
| 8,022,095 B2 | 9/2011 | Plachetka |
| 8,124,126 B2 | 2/2012 | Bosse et al. |
| 8,236,328 B2 | 8/2012 | Babcock et al. |
| 8,263,126 B2 | 9/2012 | Oury et al. |
| 8,268,791 B2 | 9/2012 | Maggio |
| 8,597,681 B2 | 12/2013 | Park et al. |
| 8,632,805 B2 | 1/2014 | Naringrekar et al. |
| 8,637,503 B2 | 1/2014 | Boland et al. |
| 8,653,066 B2 | 2/2014 | Bosse |
| 8,703,196 B2 | 4/2014 | Babcock et al. |
| 8,728,522 B2 | 5/2014 | Bosse et al. |
| 8,822,489 B2 | 9/2014 | Kumar et al. |
| 8,920,837 B2 | 12/2014 | Pilgaonkar et al. |
| 9,034,377 B2 | 5/2015 | Wright et al. |
| 9,044,435 B2 | 6/2015 | Wright et al. |
| 9,226,901 B2 | 1/2016 | Bosse et al. |
| 9,393,207 B2 | 7/2016 | Bosse |
| 9,399,022 B2 | 7/2016 | Bosse |
| 9,402,813 B2 | 8/2016 | Bosse |
| 9,427,407 B2 | 8/2016 | Bosse |
| 9,433,625 B2 | 9/2016 | Bosse et al. |
| 2003/0008892 A1 | 1/2003 | Coe et al. |
| 2003/0044458 A1 | 3/2003 | Wright et al. |
| 2003/0068370 A1 | 4/2003 | Sackler |
| 2003/0068375 A1 | 4/2003 | Wright et al. |
| 2003/0092724 A1 | 5/2003 | Kao et al. |
| 2003/0124185 A1 | 7/2003 | Oshlack et al. |
| 2003/0133982 A1 | 7/2003 | Heimlich et al. |

(56) References Cited

U.S. PATENT DOCUMENTS

| | | |
|---|---|---|
| 2003/0181462 A1 | 9/2003 | Doods et al. |
| 2003/0225002 A1 | 12/2003 | Livingstone |
| 2004/0019080 A1 | 1/2004 | Sheftell et al. |
| 2004/0043071 A1 | 3/2004 | Pauletti et al. |
| 2004/0047907 A1 | 3/2004 | Oshlack et al. |
| 2004/0136913 A1 | 7/2004 | Dugger et al. |
| 2004/0136914 A1 | 7/2004 | Dugger et al. |
| 2004/0152713 A1 | 8/2004 | Petrie |
| 2004/0156859 A1 | 8/2004 | Ezrin et al. |
| 2004/0156903 A1 | 8/2004 | Abrams et al. |
| 2004/0167200 A1 | 8/2004 | Coe et al. |
| 2004/0170680 A1 | 9/2004 | Oshlack et al. |
| 2004/0185096 A1 | 9/2004 | Oshlack et al. |
| 2004/0195413 A1 | 10/2004 | Reed et al. |
| 2004/0213828 A1 | 10/2004 | Smith |
| 2004/0241159 A1 | 12/2004 | De |
| 2004/0248956 A1 | 12/2004 | Hagmann et al. |
| 2004/0266807 A1 | 12/2004 | Oshlack et al. |
| 2005/0074493 A1 | 4/2005 | Mehta et al. |
| 2005/0080012 A1 | 4/2005 | Mickle et al. |
| 2005/0084530 A1 | 4/2005 | Rao et al. |
| 2005/0106249 A1 | 5/2005 | Hwang et al. |
| 2005/0147710 A1 | 7/2005 | Teckoe et al. |
| 2005/0158382 A1 | 7/2005 | Cruz et al. |
| 2005/0163856 A1 | 7/2005 | Maloney et al. |
| 2005/0232986 A1 | 10/2005 | Brown et al. |
| 2005/0232987 A1 | 10/2005 | Srinivasan et al. |
| 2005/0232993 A1* | 10/2005 | Brown ............... A61K 9/2077 424/468 |
| 2005/0266032 A1 | 12/2005 | Srinivasan et al. |
| 2005/0272810 A1 | 12/2005 | Davis et al. |
| 2005/0281875 A1 | 12/2005 | Srinivasan et al. |
| 2005/0282879 A1 | 12/2005 | Salehani |
| 2006/0009512 A1 | 1/2006 | Curwen et al. |
| 2006/0029664 A1 | 2/2006 | Srinivasan et al. |
| 2006/0057205 A1 | 3/2006 | Srinivasan et al. |
| 2006/0073189 A1 | 4/2006 | Pinney et al. |
| 2006/0110327 A1 | 5/2006 | Emigh et al. |
| 2006/0127479 A1 | 6/2006 | Kumaraperumal et al. |
| 2006/0134207 A1 | 6/2006 | Srinivasan et al. |
| 2006/0142273 A1 | 6/2006 | Rudolf et al. |
| 2006/0165604 A1 | 7/2006 | Dugger, III |
| 2006/0177380 A1 | 8/2006 | Emigh et al. |
| 2006/0183693 A1 | 8/2006 | Doods et al. |
| 2006/0198790 A1 | 9/2006 | Dugger, III |
| 2006/0204578 A1 | 9/2006 | Vergez et al. |
| 2006/0240105 A1 | 10/2006 | Devane et al. |
| 2007/0003622 A1 | 1/2007 | Srinivasan et al. |
| 2007/0059254 A1 | 3/2007 | Singh |
| 2007/0060500 A1 | 3/2007 | Mickle et al. |
| 2007/0099849 A1 | 5/2007 | Livingstone |
| 2007/0148097 A1 | 6/2007 | Finn et al. |
| 2007/0166336 A1 | 7/2007 | Delmarre et al. |
| 2007/0191462 A1 | 8/2007 | Hettiarachchi et al. |
| 2007/0197573 A1 | 8/2007 | Sadee et al. |
| 2007/0231268 A1 | 10/2007 | Emigh et al. |
| 2007/0286875 A1 | 12/2007 | Dagar et al. |
| 2008/0044482 A1 | 2/2008 | Oshlack et al. |
| 2008/0057122 A1 | 3/2008 | Toney-Parker et al. |
| 2008/0074208 A1 | 3/2008 | Lee |
| 2008/0075781 A1 | 3/2008 | Oshlack et al. |
| 2008/0103134 A1 | 5/2008 | Rudolf et al. |
| 2008/0131517 A1 | 6/2008 | Fawzy et al. |
| 2008/0181941 A1 | 7/2008 | Oshlack et al. |
| 2008/0213343 A1 | 9/2008 | Obermeier et al. |
| 2008/0292699 A1 | 11/2008 | Brown et al. |
| 2009/0004281 A1 | 1/2009 | Nghiem et al. |
| 2009/0068269 A1 | 3/2009 | Oshlack et al. |
| 2009/0118170 A1 | 5/2009 | Dugger, III |
| 2009/0124554 A1 | 5/2009 | Dugger, III |
| 2009/0156581 A1 | 6/2009 | Dillon et al. |
| 2009/0162297 A1 | 6/2009 | Dugger, III et al. |
| 2009/0162298 A1 | 6/2009 | Dugger, III et al. |
| 2009/0163451 A1 | 6/2009 | Porreca et al. |
| 2009/0175939 A1 | 7/2009 | Bosse et al. |
| 2009/0232898 A1 | 9/2009 | Pettersson et al. |
| 2009/0311335 A1 | 12/2009 | Jenkins et al. |
| 2010/0008995 A1 | 1/2010 | Duncalf et al. |
| 2010/0112050 A1 | 5/2010 | Ryoo et al. |
| 2010/0143469 A1 | 6/2010 | Bosse |
| 2010/0144754 A1 | 6/2010 | Peltz et al. |
| 2010/0159007 A1 | 6/2010 | Staniforth |
| 2010/0160378 A1 | 6/2010 | Maggio |
| 2010/0196471 A1 | 8/2010 | Jain et al. |
| 2011/0066100 A1 | 3/2011 | Sebree et al. |
| 2011/0077272 A1 | 3/2011 | Main |
| 2011/0105441 A1 | 5/2011 | Zhang et al. |
| 2011/0118189 A1 | 5/2011 | Farr et al. |
| 2011/0262539 A1 | 10/2011 | Bosse et al. |
| 2012/0201888 A1 | 8/2012 | Bosse et al. |
| 2012/0202866 A1 | 8/2012 | Dugger, III et al. |
| 2014/0030322 A1 | 1/2014 | Bosse et al. |
| 2014/0073678 A1 | 3/2014 | Dadey et al. |
| 2014/0112981 A1 | 4/2014 | Oshlack et al. |
| 2014/0134248 A1 | 5/2014 | Bosse |
| 2014/0221416 A1 | 8/2014 | Guido et al. |
| 2014/0271896 A1 | 9/2014 | Abu et al. |
| 2014/0323512 A1 | 10/2014 | McKenna |
| 2014/0357658 A1 | 12/2014 | Kaiko et al. |
| 2015/0030677 A1 | 1/2015 | Adjei et al. |
| 2015/0290211 A1 | 10/2015 | Bosse et al. |
| 2015/0297525 A1 | 10/2015 | Bosse et al. |
| 2015/0306040 A1 | 10/2015 | Bosse et al. |
| 2015/0320685 A1 | 11/2015 | Bosse et al. |
| 2015/0328210 A1 | 11/2015 | Bosse |
| 2015/0328212 A1 | 11/2015 | Bosse |
| 2016/0051474 A1 | 2/2016 | Bosse et al. |
| 2016/0317447 A1 | 11/2016 | Bosse |
| 2016/0375013 A1 | 12/2016 | Bosse |
| 2016/0375014 A1 | 12/2016 | Bosse |
| 2017/0049704 A1 | 2/2017 | Bosse |

FOREIGN PATENT DOCUMENTS

| | | |
|---|---|---|
| FR | 2787713 A1 | 6/2000 |
| WO | WO-9718801 A1 | 5/1997 |
| WO | WO-9942095 A1 | 8/1999 |
| WO | WO-02080953 A2 | 10/2002 |
| WO | WO-02080953 A3 | 12/2002 |
| WO | WO-2006022996 A2 | 3/2006 |
| WO | WO-2006103407 A2 | 10/2006 |
| WO | WO-2006103418 A1 | 10/2006 |
| WO | WO-2006022996 A3 | 12/2006 |
| WO | WO-2007035573 A2 | 3/2007 |
| WO | WO-2007035573 A3 | 6/2007 |
| WO | WO-2007130507 A2 | 11/2007 |
| WO | WO-2008027350 A2 | 3/2008 |
| WO | WO-2008027350 A3 | 5/2008 |
| WO | WO-2008070268 A2 | 6/2008 |
| WO | WO-2008074419 A1 | 6/2008 |
| WO | WO-2008124081 A2 | 10/2008 |
| WO | WO-2008070268 A3 | 11/2008 |
| WO | WO-2009089494 A2 | 7/2009 |
| WO | WO-2009089494 A3 | 1/2010 |
| WO | WO-2010062688 A2 | 6/2010 |
| WO | WO-2011006012 A1 | 1/2011 |
| WO | WO-2010062688 A3 | 5/2012 |
| WO | WO-2014043346 A2 | 3/2014 |
| WO | WO-2015157738 A1 | 10/2015 |

OTHER PUBLICATIONS

Anderson. Paracetamol (Acetaminophen): mechanisms of action. Paediatr Anaesth. Oct. 2008;18(10):915-21. doi: 10.1111/j.1460-9592.2008.02764.x.

Anesthetic, Analgesic, Rheumatic Drugs Division, Pre-IND Meeting with Charleston Laboratories, Inc. Nov. 8, 2007, Silver Springs, MD.

Aparasu, et al. Opioid-induced emesis among hospitalized nonsurgical patients: effect on pain and quality of life. J Pain Symptom Manage. Oct. 1999;18(4):280-8.

Apfel, et al. A factorial trial of six interventions for the prevention of postoperative nausea and vomiting. n. Engl J Med. Jun. 10, 2004;350(24):2441-51.

(56) References Cited

OTHER PUBLICATIONS

Apfel, et al. A risk score to predict the probability of postoperative vomiting in adults. Acta Anaesthesiol Scand. May 1998;42(5):495-501.
Apfel, et al. A simplified risk score for predicting postoperative nausea and vomiting: conclusions from cross-validations between two centers. Anesthesiology. Sep. 1999;91(3):693-700.
Apfel, et al. The discriminating power of a risk score for postoperative vomiting in adults undergoing various types of surgery. Acta Anaesthesiol Scand. May 1998;42(5):502-9.
Apfelbaum, et al. Reliability and validity of the perioperative opioid-related symptom distress scale. Anesth Analg. Sep. 2004;99(3):699-709, table of contents.
Armstrong, et al. Pharmacokinetic drug interactions of morphine, codeine, and their derivatives: Theory and clinical reality, Part II. Psychosomatics. 44(6):515-20, 2003.
Aronson Ce, Hanno Ers. Effect of promethazine on the isolated perfused rat heart. Gen Pharmacol. 10:389-395, 1979.
Atkinson, et al. Hierarchical construct validity of the treatment satisfaction questionnaire for medication (TSQM version II) among outpatient pharmacy consumers. Value Health. Nov.-Dec. 2005;8 Suppl 1:S9-S24.
Balster, et al. Guidelines and methodological reviews concerning drug abuse liability assessment. Drug Alcohol Depend. Jun. 5, 2003;70(3 Suppl):S13-40.
Barkin. Acetaminophen, aspirin, or Ibuprofen in combination analgesic products. Am J Ther. Nov.-Dec. 2001;8(6):433-42.
Becker, et al. Drug-induced QT interval prolongation in cancer patients. Oncol Rev., 2010; 4(4):223-232.
Benning, et al. Validation of the in vivo CD1 mouse splenocyte micronucleus test. Mutagenesis. May 1994;9(3):199-204.
Bergman, et al. Series: current issues in mutagenesis and carcinogenesis, No. 65. The genotoxicity and carcinogenicity of paracetamol: a regulatory (re)view.Mutat Res. Feb. 1, 1996;349(2):263-88.
Bessems, et al. Paracetamol (acetaminophen)-induced toxicity: molecular and biochemical mechanisms, analogues and protective approaches. Crit Rev Toxicol. Jan. 2001;31(1):55-138.
Betancourt, et al. Efficacy of ibuprofen-hydrocodone for the treatment of postoperative pain after periodontal surgery. J Periodontol. Jun. 2004;75(6):872-6.
Bouillon, T. et al. A model of the ventilatory depressant potency of remifentanil in the non-steady state. Anesthesiology 2003;99:779-87.
Bovbjerg, et al. An experimental analysis of classically conditioned nausea during cancer chemotherapy. Psychosom Med. Nov.-Dec. 1992;54(6):623-37.
Braude, et al. Ondansetron versus promethazine to treat acute undifferentiated nausea in the emergency department: a randomized, double-blind, noninferiority trial. Acad Emerg Med. Mar. 2008;15(3):209-15. doi: 10.1111/j.1553-2712.2008.00060.x.
Bruera, et al. The Edmonton Symptom Assessment System (ESAS): a simple method for the assessment of palliative care patients. J Palliat Care. 1991 Summer;7(2):6-9.
Burke, et al. Evaluation of pyrazole and ethanol induced S9 fraction in bacterial mutagenicity testing. Mutagenesis. Jan. 1994;9(1):23-9.
Chang DJ, et al. Comparison of rofecoxib and a multidose oxycodone/ acetaminophen regimen for the treatment of acute pain following oral surgery: a randomized controlled trial. Curr. Med. Res. Opin. 2004; 20: 939-49.
Chang, et al. Validation of the Edmonton Symptom Assessment Scale. Cancer. May 1, 2000;88(9):2164-71.
Chapin, et al. Reproductive assessment by continuous breeding: evolving study design and summaries of ninety studies. Environ Health Perspect. Feb. 1997;105 Suppl 1:199-205.
Charleston Laboratories' Investigational New Drug Application, pp. 93-94, filed with the U.S. Food and Drug Administration on Sep. 5, 2008. Charleston Laboratories is the assignee of the present application.
Chen, et al. Design and analysis for drug abuse potential studies: issues and strategies for implementing a crossover design. DIA J. 2007; 41:481-489.
Cherny. Opioid analgesics: comparative features and prescribing guidelines. Drugs. May 1996;51(5):713-37.
Chia, et al. The effect of promethazine on postoperative pain: a comparison of preoperative, postoperative, and placebo administration in patients following total abdominal hysterectomy. Acta Anaesthesiol Scand. May 2004;48(5):625-30.
Chow, et al. Chapter 4: Statistical Methods for Average Bioavailability. Design and Analysis of Bioavailability and Bioequivalence Studies. 2nd Edition. Published by Marcel Dekker, 2000. p. 98. DCN 3007688.
Chow, et al. Chapter 6: Transformation and analysis of individual subject ratios. Design and Analysis of Bioavailability and Bioequivalence Studies. 2nd Edition. Published by Marcel Dekker, 2000. p. 161.
Cisternas, et al. Trends in medical care expenditures of US adults with arthritis and other rheumatic conditions 1997 to 2005. J Rheumatol. Nov. 2009;36(11):2531-8. doi: 10.3899/jrheum.081068. Epub Oct. 1, 2009.
Cleren, et al. Promethazine protects against 1-methyl-4-phenyl-1,2,3,6-tetrahydropyridine neurotoxicity. Neurobiol Dis. Dec. 2005;20(3):701-8. Epub Aug. 26, 2005.
Cliet, et al. In vivo micronucleus test using mouse hepatocytes. Mutat Res. Dec. 1989;216(6):321-6.
Codapane Forte Paracetamol and codeine phosphate Product Information pp. 1-10 Jul. 6, 2016.
Colagiuri, et al. Patient expectancy and post-chemotherapy nausea: a meta-analysis. Ann Behav Med. Aug. 2010;40(1):3-14. doi: 10.1007/s12160-010-9186-4.
Colloca, et al. Placebo and Nocebo. In the: Textbook of Clinical Pain Management 2E, edited by Rice A, Howard R, Justins D, Miaskowski C, Newton-John T. Hodder Arnold, Practice and Procedures. London NW1 3BH, 2008, 499-513.
Colloca, et al. The role of learning in nocebo and placebo effects. Pain. May 2008;136(1-2):211-8. doi: 10.1016/j.pain.2008.02.006. Epub Mar. 26, 2008.
Coluzzi, F. et al. Non-Analgesic Effects of Opioids: Opioid-induced Nausea and Vomiting: Mechanisms and Strategies for their Limitation. Current Pharmaceutical Design, 18(37):6043-6052 (2012).
Cone, et al. Comparative metabolism of hydrocodone in man, rat, guinea pig, rabbit, and dog. Drug Metab Dispos. Jul.-Aug. 1978;6(4):488-93.
Connolly, et al. Alpha 4-2 beta 2 and other nicotinic acetylcholine receptor subtypes as targets of psychoactive and addictive drugs. Br J Pharmacol. Mar. 1992;105(3):657-66.
Cooper, et al. A model to evaluate mild analgesics in oral surgery outpatients. Clin Pharmacol Ther. Aug. 1976;20(2):241-50.
Cooper, et al. Ibuprofen and acetaminophen in the relief of acute pain: a randomized, double-blind, placebo-controlled study. J Clin Pharmacol. Nov. 1989;29(11):1026-30.
Dagenais, et al. Systematic review of the prevalence of radiographic primary hip osteoarthritis. Clin Orthop Relat Res. Mar. 2009;467(3):623-37. doi: 10.1007/s11999-008-0625-5. Epub Nov. 27, 2008.
Daniels, et al. The analgesic efficacy of valdecoxib vs. oxycodone/ acetaminophen after oral surgery. J Am Dent Assoc. May 2002;133(5):611-21; quiz 625.
Daniels S., et al. A randomized, double-blind, placebo-controlled phase 3 study of the relative efficacy and tolerability of tapentadol IR and oxycodone IR for acute pain Curr Med Res Opin. 2009; 25: 1551-61.
Davis, et al. Species differences in hepatic glutathione depletion, covalent binding and hepatic necrosis after acetaminophen. Life Sci. Jun. 1, 1974;14(11):2099-109.
Davis. Hydrocodone. Opioids for cancer pain. Oxford UK: Oxford University Press. 2005. pp. 59-68. ISBN 0-19-852943-0.
DeSchepper, H.U. et al. Opioids and the gut: pharmacology and current clinical experience. Neurogastroenterol Motil. Aug. 2004;16(4):383-94.

(56) References Cited

OTHER PUBLICATIONS

Desjardins, et al. A randomized controlled study comparing rofecoxib, diclofenac sodium, and placebo in post-bunionectomy pain. Curr Med Res Opin. Oct. 2004;20(10):1523-37.
Desjardins, et al. A single preoperative oral dose of valdecoxib, a new cyclooxygenase-2 specific inhibitor, relieves post-oral surgery or bunionectomy pain. Anesthesiology. Sep. 2002;97(3):565-73.
Desjardins, et al. Analgesic efficacy of preoperative parecoxib sodium in an orthopedic pain model. J Am Podiatr Med Assoc. May-Jun. 2004;94(3):305-14.
Devalia, et al. Dissociation of cell death from covalent binding of paracetamol by flavones in a hepatocyte system. Biochem Pharmacol. Dec. 1, 1982;31(23):3745-9.
Dipasquale, et al. Post nidatory action of various compounds representing several pharmacological classes. Res Commun Chem Pathol Pharmacol. Apr. 1974;7(4):701-14.
Dunn, et al. Genotoxicity of analgesic compounds assessed by an in vitro micronucleus assay. Mutat Res. Nov. 1987;189(3):299-306.
European search report dated Nov. 19, 2014 for EP Application No. 14177981.9.
Farrar, et al. Clinically important changes in acute pain outcome measures: a validation study. J Pain Symptom Manage. May 2003;25(5):406-11.
FDA Monograph for Phenergan, Revised Jul. 2005; http://www.drugs.com/pro/phenergan.html; accessed Feb. 19, 2014.
Fendrick, et al. Self-selection and use patterns of over-the-counter omeprazole for frequent heartburn. Clin Gastroenterol Hepatol. Jan. 2004;2(1):17-21.
Fishman, et al. Bonica's Management of Pain, 4th Edition, Chapter 43: Cancer Pain: Principles of Management and Pharmacotherapy, pp. 582 & 588 (2010).
Ford. Soft-tissue bunionectomy in podiatric surgery. Clin Podiatr Med Surg. Jan. 1991;8(1):63-70.
Foster, et al. Complicated pain management in a CYP450 2D6 poor metabolizer. Pain Pract. Dec. 2007;7(4):352-6.
Fricke, et al. A double-blind, single-dose comparison of the analgesic efficacy of tramadol/acetaminophen combination tablets, hydrocodone/acetaminophen combination tablets, and placebo after oral surgery. Clin Ther. Jun. 2002;24(6):953-68.
Gan, et al. A consensus panel identification of risk factors for PONV. Anesth. 2002; 96:A19.
Gan, et al. Consensus guidelines for managing postoperative nausea and vomiting. Anesth Analg. Jul. 2003;97(1):62-71, table of contents.
Gan, et al. Risk factors for postoperative nausea and vomiting. Anesth Analg. Jun. 2006;102(6):1884-98.
Gordon, et al. Activation of P-glycoprotein efflux transport ameliorates opioid CNS effects without diminishing analgesia. Drug Disc Today: Therap Strat 2009; 6:97-103.
Gotzsche. Reporting of outcomes in arthritis trials measured on ordinal and interval scales is inadequate in relation to meta-analysis. Ann Rheum Dis. Apr. 2001;60(4):349-52.
Gotzsche. Sensitivity of effect variables in rheumatoid arthritis: a meta-analysis of 130 placebo controlled NSAID trials. J Clin Epidemiol. 1990;43(12):1313-8.
Gregorian, Jr. et al., Importance of Side Effects in Opioid Treatment: A Trade-Off Analysis With Patients and Physicians. J Pain. 2010; 11: 1095-108.
Griffiths, et al. Principles of initial experimental drug abuse liability assessment in humans. Drug Alcohol Depend. Jun. 5, 2003;70(3 Suppl):S41-54.
Guidance for Industry: Bioavailability and Bioequivalence Studies for Orally Administered Drug Products-General Considerations U.S. Department of Health and Human Services Food and Drug Administration Center for Drug Evaluation and Research (CDER) Mar. 2003.
Guidance for Industry: Statistical Approaches to Establishing Bioequivalence U.S. Department of Health and Human Services Food and Drug Administration Center for Drug Evaluation and Research (CDER) Jan. 2001.
Hardy, et al. A double-blind, randomised, parallel group, multinational, multicentre study comparing a single dose of ondansetron 24 mg p.o. with placebo and metoclopramide 10 mg t.d.s. p.o. in the treatment of opioid-induced nausea and emesis in cancer patients. Support Care Cancer. Apr. 2002;10(3):231-6.
Hays, et al. The RAND 36-Item Health Survey 1.0. Health Econ. Oct. 1993;2(3):217-27.
Hersh, E. et al. Opioid-Induced Nausea and Vomiting (OINV) in patients without immediate post-op nausea/vomiting. The Journal of Pain, 16(4); S80 (Apr. 2015).
Hersh, E. et al. What is the likelihood of opioid-induced nausea and vomiting (OINV) in patients with a history that is only suggestive of OINV? The Journal of Pain, vol. 16(4); S16 (Apr. 2015).
Hersh, E. et al. Efficacy of CL-108 compared to hydrocodone 7.5 mg/acetaminophen 325 mg in preventing vomiting and the use of anti-emetics, Opioid-Induced Nausea and Vomiting (OINV). The Journal of Pain, vol. 1(4): S82 (Apr. 2016).
Hersh, et al. Ibuprofen liquigel for oral surgery pain. Clin Ther. Nov. 2000;22(11):1306-18.
Holzer, P. Treatment of opioid-induced gut dysfunction. Expert Opin Investig Drugs 2007;16:181-194.
International Application No. PCT/US2015/025481 International Preliminary Report on Patentability dated Oct. 12, 2016.
International Application No. PCT/US2016/056910 International Search Report and Written Opinion dated Dec. 22, 2016.
International preliminary report on patentability dated Jul. 22, 2010 for PCT Application No. PCT/US09/30662.
International search report and written opinion dated Jun. 17, 2015 for PCT Application No. US2015/025481.
International search report dated May 22, 2009 for Application No. US2009/30662.
International search report dated Sep. 1, 2010 for PCT Application No. PCT/US2010/41433.
International search report dated Sep. 23, 2008 for Application No. PCT/US2007/80831.
Interview summary dated Sep. 18, 2015 for U.S. Appl. No. 14/789,888.
Interview summary dated Oct. 2, 2015 for U.S. Appl. No. 14/789,888.
Interview summary dated Oct. 20, 2015 for U.S. Appl. No. 14/036,946.
Interview summary dated Nov. 23, 2015 for U.S. Appl. No. 14/748,614.
Interview summary dated Nov. 23, 2015 for U.S. Appl. No. 14/748,617.
Interview summary dated Nov. 24, 2015 for U.S. Appl. No. 14/244,455.
Interview summary dated Nov. 24, 2015 for U.S. Appl. No. 14/748,605.
Interview summary dated Nov. 25, 2015 for U.S. Appl. No. 14/789,883.
Jang, J.O. et al. Pharmacokinetic Study of Promethazine in Korean Healthy Subjects Using a Validated HPLC Method. J Appl Pharm. 2005;13:118-122.
Kalso E., et al. Opioids in chronic non-cancer pain: systematic review of efficacy and safety Pain. 2004; 112: 372-80.
Korn, et al. Comparison of rofecoxib and oxycodone plus acetaminophen in the treatment of acute pain: a randomized, double-blind, placebo-controlled study in patients with moderate to severe postoperative pain in the third molar extraction model. Clin Ther. May 2004;26(5):769-78.
Kovac, A. Prophylaxis of postoperative nausea and vomiting: controversies in the use of serotonin 5-hydroxytryptamine subtype 3 receptor antagonists. J Clin Anesth. Jun. 2006;18(4):304-18.
Lalley, P.M. Mu-opioid receptor agonist effects on medullary respiratory neurons in the cat: evidence for involvement in certain types of ventilatory disturbances. Am J Physiol Regul Integr Comp Physiol. Dec. 2003;285(6):R1287-304.
Lasagna. A plea for the 'Naturalistic' study of medicines. Eur J Clin Pharmacol. 1974;7(3):153-4.
Lasagna. The clinical measurement of pain. Ann N Y Acad Sci. Mar. 30, 1960;86:28-37.

(56) References Cited

OTHER PUBLICATIONS

Lasagna. The controlled clinical trial: theory and practice. J Chronic Dis. Apr. 1955;1(4):353-67.

Litkowski, et al. Analgesic efficacy and tolerability of oxycodone 5 mg/ibuprofen 400 mg compared with those of oxycodone 5 mg/acetaminophen 325 mg and hydrocodone 7.5 mg/acetaminophen 500 mg in patients with moderate to severe postoperative pain: a randomized, double-blind, placebo-controlled, single-dose, parallel-group study in a dental pain model. Clin Ther. Apr. 2005;27(4):418-29.

Malmstrom, et al. Comparison of rofecoxib and celecoxib, two cyclooxygenase-2 inhibitors, in postoperative dental pain: a randomized, placebo- and active-comparator-controlled clinical trial. Clin Ther. Oct. 1999;21(10):1653-63.

Mayo Clinic Website. Cough and Cold Combination (Oral Route). Available at www.mayoclinic.com/health/drug-infomation/DR602361. Accessed Oct. 2, 2007.

Meert, et al. A preclinical comparison between different opioids: antinociceptive versus adverse effects. Pharmacol Biochem Behav. Feb. 2005;80(2):309-26. Epub Jan. 7, 2005.

Mellen, N.M., et al. Opioid-induced quantal slowing reveals dual networks for respiratory rhythm generation. Neuron. Mar. 6, 2003;37(5):821-6.

Melzack, et al. On the language of pain. Anesthesiology. Jan. 1971;34(1):50-9.

Moore, et al. Prevalence of opioid adverse events in chronic non-malignant pain: systematic review of randomised trials of oral opioids. Arthritis Res Ther. 2005;7(5):R1046-51. Epub Jun. 28, 2005.

Moser, et al. No more than necessary: Safety and efficacy of low-dose promethazine. Annals of Pharmacotherapy. 2006; 40:45-48.

Murphy, et al. Comorbidities are very common among people with arthritis. Poster 43. 20th national Conference on Chronic Disease Prevention and Control. Washing, DC, Centers for Disease Control and Prevention. 2009.

Musclow, Shirley L. et al., Long-acting morphine following hip or knee replacement: A randomized, double-blind, placebo-controlled trial. Pain Res Manag. 2012; 17: 83-8.

Navratil, H. Contribution to the study of dihydrone pectinate. Its administration in the course of anesthesia 100 observations. Rev. MRO. Toulouse. 1966, II. pp. 249-254 (in French with English translation).

Neogi, et al. Composite versus individual measures of disease activity in rheumatoid arthritis. J Rheumatol. Feb. 2008;35(2):185-7.

Neogi, et al. Relative responsiveness of physician/assessor-derived and patient-derived core set measures in rheumatoid arthritis trials. J Rheumatol. May 2008;35(5):757-62. Epub Apr. 15, 2008.

Notice of allowance dated Jan. 28, 2014 for U.S. Appl. No. 12/967,423.
Notice of allowance dated Feb. 8, 2016 for U.S. Appl. No. 14/789,888.
Notice of allowance dated Feb. 18, 2016 for U.S. Appl. No. 14/244,455.
Notice of allowance dated Feb. 18, 2016 for U.S. Appl. No. 14/748,609.
Notice of allowance dated Feb. 19, 2016 for U.S. Appl. No. 14/748,605.
Notice of allowance dated Feb. 19, 2016 for U.S. Appl. No. 14/748,614.
Notice of allowance dated Feb. 24, 2016 for U.S. Appl. No. 14/748,621.
Notice of allowance dated Sep. 24, 2015 for U.S. Appl. No. 14/036,946.
Notice of allowance dated Oct. 2, 2015 for U.S. Appl. No. 14/789,888.
Notice of allowance dated Oct. 7, 2013 for U.S. Appl. No. 12/444,521.
Notice of allowance dated Oct. 11, 2011 for U.S. Appl. No. 12/351,704.
Notice of allowance dated Nov. 3, 2015 for U.S. Appl. No. 14/036,946.
Notice of allowance dated Nov. 4, 2015 for U.S. Appl. No. 14/789,888.
Notice of Allowance dated Jun. 3, 2016 in U.S. Appl. No. 14/748,609.
Notice of Allowance dated Jun. 7, 2016 in U.S. Appl. No. 14/748,605.
Notice of Allowance dated Jun. 8, 2016 in U.S. Appl. No. 14/244,455.

O'Connor, et al. Framing effects on expectations, decisions, and side effects experienced: the case of influenza immunization. J Clin Epidemiol. Nov. 1996;49(11):1271-6.

Office action dated Feb. 29, 2012 for U.S. Appl. No. 12/967,423.
Office action dated Feb. 7, 2013 for U.S. Appl. No. 12/444,521.
Office action dated Mar. 27, 2015 for U.S. Appl. No. 14/036,946.
Office action dated Jun. 29, 2012 for U.S. Appl. No. 12/444,521.
Office action dated Aug. 14, 2015 for U.S. Appl. No. 14/789,883.
Office action dated Aug. 14, 2015 for U.S. Appl. No. 14/789,886.
Office action dated Sep. 6, 2012 for U.S. Appl. No. 12/967,423.
Office action dated Sep. 8, 2015 for U.S. Appl. No. 14/748,605.
Office action dated Sep. 8, 2015 for U.S. Appl. No. 14/748,609.
Office action dated Sep. 10, 2015 for U.S. Appl. No. 14/748,617.
Office action dated Sep. 17, 2015 for U.S. Appl. No. 14/244,455.
Office action dated Sep. 17, 2015 for U.S. Appl. No. 14/748,614.
Office action dated Sep. 18, 2015 for U.S. Appl. No. 14/789,888.
Office action dated Oct. 2, 2015 for U.S. Appl. No. 14/748,613.
Office action dated Oct. 2, 2015 for U.S. Appl. No. 14/748,621.
Office action dated Oct. 8, 2014 for U.S. Appl. No. 14/036,946.
Office action dated Sep. 20, 2010 for U.S. Appl. No. 12/351,704.

Oldfield, et al. Oxycodone/Ibuprofen combination tablet: a review of its use in the management of acute pain. Drugs. 2005;65(16):2337-54.

Package Insert. Duragesic. Janssen Pharmaceutica Products. 2003.
Package Insert. Oxycontin. Purdue Pharma L.P. Sep. 7, 2007.

Palangio, et al. Combination hydrocodone and ibuprofen versus combination oxycodone and acetaminophen in the treatment of moderate or severe acute low back pain. Clin Ther. Jan. 2002;24(1):87-99.

Palangio, M., et al. Dose-response effect of combination hydrocodone with ibuprofen in patients with moderate to severe postoperative pain. Clin Ther. Aug. 2000;22(8):990-1002.

Paoloni, et al. Low incidence of nausea and vomiting with intravenous opiate analgesia in the ED. Am J Emerg Med. Nov. 2002;20(7):604-8.

Park, Yong-Beom et al., A randomized study to compare the efficacy and safety of extended-release and immediate-release tramadol HCl/acetaminophen in patients with acute pain following total knee replacement. Curr Med Res Opin. 2015; 31: 75-84.

Peloso, P.M., et al. Protocol TRP-CAN-1 Study Group. Analgesic efficacy and safety of tramadol/ acetaminophen combination tablets (Ultracet) in treatment of chronic low back pain: a multicenter, outpatient, randomized, double blind, placebo controlled trial. J Rheumatol. Dec. 2004;31(12):2454-63.

Petersson, et al. Radiographic osteoarthritis of the knee classified by the Ahlbäck and Kellgren & Lawrence systems for the tibiofemoral joint in people aged 35-54 years with chronic knee pain. Ann Rheum Dis. Aug. 1997;56(8):493-6.

Porreca, et al. Nausea and vomiting side effects with opioid analgesics during treatment of chronic pain: mechanisms, implications, and management options. Pain Med. May-Jun. 2009;10(4):654-62. doi: 10.1111/j.1526-4637.2009.00583.x. Epub Mar. 19, 2009.

Promethazine, Description and Brand Names Drug Information by Micromedex Retrieved Mar. 27, 2017 from: http://www.mayoclinic.org/drugs-supplements/promethazine-oral- route/description/drg-20070609?p=1; pp. 1-17.

Promethazine HCl and Hydrocodone Bitartrate Syrup. WraSer Pharmaceuticals, Madison, MS. Jan. 2007.

Prosolve Data Sheet [online] retrieved on Feb. 27, 2012 from: http://www.jrspharma.de/Pharma/wEnglisch/produktinfo/prosolv_smcc/prosolv_smcc_grades.shtml; 2 pages.

(56) References Cited

OTHER PUBLICATIONS

Quessy. Two-stage enriched enrolment pain trials: a brief review of designs and opportunities for broader application. Pain. Jan. 2010;148(1):8-13. doi: 10.1016/j.pain.2009.10.029. Epub Nov. 25, 2009.
Ragg, et al. Comparison of the efficacy of paracetamol versus paracetamol, codeine and promethazine (Painstop) for premedication and analgesia for myringotomy in children. Anaesth Intensive Care. Feb. 1997;25(1):29-32.
Reidenberg, et al. Adverse nondrug reactions. N Engl J Med. Sep. 26, 1968;279(13):678-9.
Richardson, S. et al. Opioid-Induced Nausea and Vomiting (OINV) in Post-Operative Patients: A Comparison of CL-108 to Hydrocodone7.5 mg/Acetaminophen 325 mg. The Journal of Pain, 17(4); Supplement, p. S83 (Apr. 2016).
Richmond, B. S. Pharmacy & Therapeutics Committees. Antiemetic Prophylaxis and Treatment of Postoperative and Opioid-Induced Nausea and Vomiting. Jul. 2007.
Rodriguez, et al. Codeine/acetaminophen and hydrocodone/acetaminophen combination tablets for the management of chronic cancer pain in adults: a 23-day, prospective, double-blind, randomized, parallel-group study. Clin Ther. Apr. 2007;29(4):581-7.
Rodriguez, et al. Incidence of weak opioids adverse events in the management of cancer pain: a double-blind comparative trial. J Palliat Med. Feb. 2007;10(1):56-60.
Rush, et al. Chemically induced nephrotoxicity: role of metabolic activation. Crit Rev Toxicol. 1984;13(2):99-160.
Sadock, et al. Kaplan & Sadock's pocket handbook of psychiatric drug treatment 4th Ed, illustrated. Lippincott Williams & Wilkins 2005; Chapter 11.
Sanofi-Aventis. Phenergan® Tablets/Elixir Data Sheet. 2007.
Sasaki, et al. Cytogenetic effects of 60 chemicals on cultured human and Chinese hamster cells. Kromosomo. 1980; 20:574-584.
Savides, et al. Acetaminophen and its toxicity. J Appl Toxicol. Apr. 1983;3(2):96-111.
Savides, et al. The toxicity and biotransformation of single doses of acetaminophen in dogs and cats. Toxicol Appl Pharmacol. Jun. 15, 1984;74(1):26-34.
Schachtel. Analgesic agents. In: Yaffe SJ and Aranda JV, eds. Pediatric Pharmacology. Therapeutic Principles in Practice. Philadelphia: WB Saunders,1992:406-412.
Schachtel, B. et al. Affective and sensory qualities of pain complement evaluative measures of opioid analgesia: results from the Qualities of Dental Pain Index. Meeting Poster May 2015.
Schachtel, B. Demonstration of the safety and efficacy of CL-108 for moderate-to-severe pain with reduction of opioid-induced nausea and vomiting. The Journal of Pain, 15(4); S81 (Apr. 2014).
Schachtel, et al. A randomized, double-blind, placebo-controlled model demonstrating the topical effect of benzydamine in children with sore throat. Clin Pharmacol Ther 1996; 59:146.
Schachtel, et al. A placebo-controlled model for assaying systemic analgesics in children. Clin Pharmacol Ther. May 1993;53(5):593-601.
Schachtel, et al. Actual-use study of omeprazole magnesium. Clin Pharmacol Ther. 2000; 67:149.
Schachtel, et al. Assaying analgesic response in children: a double-blind, placebo-controlled model involving earache. Pediatr Res 1991; 29:124A.
Schachtel, et al. Caffeine as an analgesic adjuvant double-blind study comparing aspirin 800mg with caffeine 64mg to aspirin 800 mg and placebo in patients with sore throat. Arch Int Med. 1991; 151:733-8.
Schachtel, et al. Change in design of actual-use study assists in interpretation of study results. Abstract p. 11. Clin Pharmacol Ther. 2001; 69:p. 11.
Schachtel, et al. Demonstration of the safety and efficacy of CL-108 for moderate-to-severe pain with reduction of opioid-induced nausea and vomiting. Abstract No. 420, Journal of Pain, Apr. 2014, vol. 15, No. 4, Supp. Suppl. 1, p, S81, 33rd Annual Scientific Meeting of the American Pain Society, Apr. 30, 2014-May 3, 2014.
Schachtel, et al. Gastric side effects of aspirin compared to acetaminophen and placebo in the treatment of headache. Acta Pharmacol Toxicol. 1986; 59:170.
Schachtel, et al. Pain relief in children. A placebo-controlled model. Clin Pharmacol Ther 1991; 49:154.
Schachtel, et al. Patients' criteria for meaningful relief to determine onset of action. Clin Pharmacol Ther. 2005; 77:p. 51.
Schachtel, et al. Rating scales for analgesics in sore throat. Clin Pharmacol Ther. Aug. 1984;36(2):151-6.
Schachtel, et al. Sore throat pain model for the evaluation of analgesics in children. J Pain and Symptom Manag 1991; 6:159.
Schachtel, et al. The Lasagna Pain Scale (LPS). Clin Pharmacol Ther. 2005; 77:93.
Schachtel. How actual-use studies augment product development. Abstract A95. AAPS—Pharmaceutical Sciences Section, American Association of Pharmaceutical Sciences (AAPS). 1 (Suppl):A95. 1999.
Schachtel. Sore throat pain. In: Max MB, Portnoy RK, and Laska EM, eds. The Design of Analgesic Clinical Trials. (Advances in pain research and therapy; vol. 18) New York: Raven Press, 1991:393-406.
Schwinghammer, et al. Comparison of the bioavailability of oral, rectal and intramuscular promethazine. Biopharm Drug Dispos. Apr.-Jun. 1984;5(2):185-94.
Seeff, et al. Acetaminophen hepatotoxicity in alcoholics. Ann Intern Med. 1986;104:399-404.
Serratoni, et al. Promethazine protection in carbon tetrachloride liver injury. An electron microscopic study. Arch Pathol. Jan. 1969;87(1):46-51.
Severin, et al. Induction of chromosome aberrations in vivo in bone-marrow cells of mice by paracetamol. Rom J Morphol Embryol. Jul.-Dec. 1995;41(3-4):117-20.
Shafer, et al. The Roche friabilator. J Am Pharm Assoc. Feb. 1956;45(2 Part 1):114-6.
Shang, et al. Effect of promethazine on electrophysiological action of guinea pig hearts. Chin J Pharmacol Toxicol; 28(5): 691-697.
Sharma, a, & Hamelin, B. a. (2003). Classic histamine H1 receptor antagonists: a critical review of their metabolic and pharmacokinetic fate from a bird's eye view. Current Drug Metabolism, 4(2), 105-129. doi:10.2174/1389200033489523.
Shibata, et al. Modification by analgesics of lesion development in the urinary tract and various other organs of rats pretreated with dihydroxy-di-N-propylnitrosamine and uracil. Jpn J Cancer Res. Feb. 1995;86(2):160-7.
Shuey, et al. Oxymorphone hydrochloride, a potent analgesic, is not carcinogenic in rats or mice. Toxicol Sci. Mar. 2007;96(1):162-73. Epub Nov. 30, 2006.
Siegers, et al. Relationships between hepatotoxicity and pharmacokinetics of paracetamol in rats and mice. Pharmacology. 1978;16(5):273-8.
Silverman, et al. Influence of promethazine on symptom-therapy scores for nausea during patient-controlled analgesia with morphine. Anesth Analg. May 1992;74(5):735-8.
Song, et al. Quantitation of promethazine and metabolites in urine samples using on-line solid-phase extraction and column-switching. J Chromatogr B Biomed Sci Appl. Nov. 5, 2001;763(1-2):9-20.
Stavchansky, et al. Bioequivalence and pharmacokinetic profile of promethazine hydrochloride suppositories in humans. J Pharm Sci. Jun. 1987;76(6):441-5.
Stavrovskaya, et al. Clinically approved heterocyclics act on a mitochondrial target and reduce stroke-induced pathology. J Exp Med. Jul. 19, 2004;200(2):211-22.
Steyer, et al. Mehrdimensionaler Befindlichkeitsfrageboen. [Multi-dimensional well-being questionnaire] Gottingen: Hogrefe. 1997.
Strenkoski-Nix, et al. Pharmacokinetics of promethazine hydrochloride after administration of rectal suppositories and oral syrup to healthy subjects. Am J Health Syst Pharm. Aug. 15, 2000;57(16):1499-505.
Sullivan, et al. The pain catastrophizing scale: development and validation. Psychological Assessment, vol. 7(4), Dec. 1995, 524-532.

(56) References Cited

OTHER PUBLICATIONS

Suzuki Takahiro. Utilize codeine phosphate. Journal of Pain and Clinical Medicine (2006), vol. 6, No. 1, p. 77-82. (in Japanese with English translation).
Szyfelbein, et al. The assessment of pain and plasma beta-endorphin immunoactivity in burned children. Pain. Jun. 1985;22(2):173-82.
Takahama, K., et al. Central and peripheral mechanisms of narcotic antitussives: codeine-sensitive and-resistant coughs. Cough. 2007;3:8.
Takahiro, S. et al. Journal of Pain and Clinical Medicine, 2006, vol. 6, No. 1, p. 77-82.
Takeda, et al. Strong opioid analgesics in cancer pain management-starting timing of administration. Cancer patient and symptomatic therapy 2003, vol. 14, No. 2, pp. 24-28 (in Japanese with English translation by Machine).
Tanaka, et al. Blockade of Na+ current by promethazine in guinea-pig ventricular myocytes. Br J Pharmacol. Aug. 1992;106(4):900-5.
Tarkkila, et al. Premedication with promethazine and transdermal scopolamine reduces the incidence of nausea and vomiting after intrathecal morphine. Acta Anaesthesiol Scand. Oct. 1995;39(7):983-6.
Taylor, et al. Pharmacokinetics of promethazine and its sulphoxide metabolite after intravenous and oral administration to man. Br J Clin Pharmacol. Mar. 1983;15(3):287-93.
Thoden, et al. Adverse non-drug reactions (ANDRs) in patients with muscle-contraction headache. Clin Pharmacol Ther. 1990; 47:149.
Tomkins, et al. Effect of cytochrome P450 2D1 inhibition on hydrocodone metabolism and its behavioral consequences in rats. J Pharmacol Exp Ther. Mar. 1997;280(3):1374-82.
Tsuruzaki, et al. Maternal consumption of antipyretic analgesics produces chromosome anomalies in F1 embryos. Teratology. 1982; 26:42A.
Urie, et al. Pharmacy education: palliative care symptom control. In:The Pharmaceutical Journal. 2000; 265:603.
U.S. Appl. No. 14/099,432 Non-Final Office Action dated Feb. 22, 2017.
U.S. Appl. No. 14/099,432 Non-Final Office Action dated Jun. 3, 2016.
U.S. Appl. No. 14/244,455 Notice of Allowability dated Mar. 8, 2016.
U.S. Appl. No. 14/244,455 Notice of Allowance dated May 17, 2016.
U.S. Appl. No. 14/748,605 Notice of Allowance dated May 6, 2016.
U.S. Appl. No. 14/748,609 Notice of Allowance dated May 3, 2016.
U.S. Appl. No. 14/748,614 Notice of Allowance dated May 20, 2016.
U.S. Appl. No. 14/748,621 Notice of Allowance dated May 3, 2016.
U.S. Appl. No. 14/789,883 Final Office Action dated Mar. 17, 2016.
U.S. Appl. No. 14/789,883 Office Action dated Sep. 9, 2016.
U.S. Appl. No. 14/789,886 Final Office Action dated Mar. 18, 2016.
U.S. Appl. No. 14/789,888 Notice of Allowance dated Apr. 5, 2016.
U.S. Appl. No. 14/789,888 Notice of Allowance dated May 20, 2016.
U.S. Appl. No. 14/930,496, filed Nov. 2, 2015.
U.S. Appl. No. 14/930,496 Office Action dated Dec. 2, 2016.
U.S. Appl. No. 15/206,955 Notice of Allowability dated Nov. 10, 2016.
U.S. Appl. No. 15/206,955 Office Action dated Aug. 11, 2016.
U.S. Appl. No. 15/263,230 Non-final Office Action dated Feb. 7, 2017.
U.S. Appl. No. 15/263,235 Non-Final Office Action dated Dec. 30, 2016.
U.S. Appl. No. 15/263,243 Final Office Action dated Jul. 13, 2017.
U.S. Appl. No. 15/263,243 Office Action dated Dec. 19, 2016.
U.S. Appl. No. 60/948375, filed Jul. 6, 2007.
U.S. Appl. No. 61/020139, filed Jan. 9, 2008.
U.S. Appl. No. 61/043037, filed Apr. 7, 2008.
U.S. Appl. No. 61/060758, filed Jun. 11, 2008.
U.S. Appl. No. 61/223999, filed Jul. 8, 2009.
U.S. Appl. No. 61/224424, filed Jul. 9, 2009.
U.S. Appl. No. 14/683,886 Office Action dated Oct. 21, 2016.
U.S. Appl. No. 15/206,955 Notice of Allowance dated Oct. 7, 2016.
U.S. Pharmacopeia National Formulary Supplement. USP 23-NF 18, 9th dated Nov. 15, 1998, p. 4678.
Vaisman, et al. The effect of promethazine hydrochloride on bilirubin metabolism in the rat. Pediatr Res. Sep. 1976;10(9):788-91.
Vinson, D.R. Treatment patterns of isolated benign headache in US emergency departments. Ann Emerg Med. Mar. 2002;39(3):215-22. (Abstract).
Walsh, et al. The relative abuse liability of oral oxycodone, hydrocodone and hydromorphone assessed in prescription opioid abusers. Drug Alcohol Depend. Dec. 1, 2008;98(3):191-202. doi: 10.1016/j.drugalcdep.2008.05.007. Epub Jul. 7, 2008.
Ward, et al. The chronic hepatic or renal toxicity of di(2-ethylhexyl) phthalate, acetaminophen, sodium barbital, and phenobarbital in male B6C3F1 mice: autoradiographic, immunohistochemical, and biochemical evidence for levels of DNA synthesis not associated with carcinogenesis or tumor promotion. Toxicol Appl Pharmacol. Dec. 1988;96(3):494-506.
Ware, et al. The MOS 36-item short-form health survey (SF-36). I. Conceptual framework and item selection. Med Care. Jun. 1992;30(6):473-83.
Watcha, et al. Postoperative nausea and vomiting. Its etiology, treatment, and prevention. Anesthesiology. Jul. 1992;77(1):162-84.
Watcha, M. et al. Postoperative Nausea and Vomiting, Anesthesiology 77:162-184 (1992).
Weisburger, et al. Effect of acetanilide and p-hydroxyacetanilide on the carcinogenicity of N-2-fluorenylacetamide and N-hydroxy-N-2-fluorenylacetamide in mice, hamsters, and female rats. J Natl Cancer Inst. Jul. 1973;51(1):235-40.
Wesson, et al. The Clinical Opiate Withdrawal Scale (COWS). J Psychoactive Drugs. Apr.-Jun. 2003;35(2):253-9.
Whitcomb, et al. Association of acetaminophen hepatotoxicity with fasting and ethanol use. JAMA. Dec. 21, 1994;272(23):1845-50.
Whitfield, et al. Parsimonious and efficient assessment of health-related quality of life in osteoarthritis research: validation of the Assessment of Quality of Life (AQoL) instrument. Health Qual Life Outcomes. 2006; 4:19.
Wiger, et al. Effects of acetaminophen and hydroxyurea on spermatogenesis and sperm chromatin structure in laboratory mice. Reprod Toxicol. Jan.-Feb. 1995;9(1):21-33.
Wikipedia. Acetaminophen. en.wikipedia.org/wiki/Acetaminophen. Last Accessed Aug. 22, 2012.
Wikipedia. Hydrocodone. en.wikipedia.org/wiki/Hydrocodone Last Accessed Aug. 22, 2012.
Williams, et al. Inhibition by acetaminophen of intestinal cancer in rats induced by an aromatic amine similar to food mutagens. Eur J Cancer Prev. Aug. 1997;6(4):357-62.
Wirth, et al. Mechanism of N-hydroxyacetylarylamine mutagenicity in the Salmonella test system: metabolic activation of N-hydroxyphenacetin by liver and kidney fractions from rat, mouse, hamster, and man. Mol Pharmacol. Jul. 1980;18(1):117-27.
Wyeth Pharmaceuticals Inc. Phenergan® Label. 2005.
Wyeth Pharmaceuticals, Inc. Phenergan Tablets. United States Prescribing Information (NDA 007935; drugs@fda.gov, listed Pi update as of Nov. 2004) for Phenergan®-promethazine hydrochloride, tablet.
Wyeth Phenergan (promethazine HCl) Label (2004) pp. 1-10.
Yaghmour, et al. Multimodal Anesthesia and Analgesia Facilitates Ambulatory Discharge of Patients Undergoing Osseous Reconstructive Ankle Surgery (RAS). Anesthesiology 2003; 99: A19 URL:http://www.asaabstracts.com/strands/asaabstracts/abstract.htm;jsessionid=D8FB91F2211878C2D0D08A062AA48B1E?year=2003&index=1&absnum=1516.
Yoon, et al. Chemical mutagenesis testing in *Drosophila*. IV. Results of 45 coded compounds tested for the National Toxicology Program. Environ Mutagen. 1985;7(3):349-67.
York, et al. Developmental toxicity studies in rats and rabbits with orally administered hydrocodone bitartrate (HB), USP. Reprod Toxicol. 2003; 17: 507.

(56) References Cited

OTHER PUBLICATIONS

Yoshida, et al. Mutagenicity of p-aminophenol in *E. coli* WP2uvrA/pKM101 and its relevance to oxidative DNA damage. Mutat Res. Jul. 8, 1998;415(1-2):139-50.
Zacny, et al. Profiling the subjective, psychomotor, and physiological effects of a hydrocodone/acetaminophen product in recreational drug users. Drug Alcohol Depend. Jun. 1, 2005;78(3):243-52. Epub Jan. 12, 2005.
Zacny, et al. Subjective, psychomotor, and physiological effects profile of hydrocodone/acetaminophen and oxycodone/acetaminophen combination products. Pain Med. May-Jun. 2008;9(4):433-43. doi: 10.1111/j.1526-4637.2007.00359.x.
Zacny, et al. Within-subject comparison of the psychopharmacological profiles of oral hydrocodone and oxycodone combination products in non-drug-abusing volunteers. Drug Alcohol Depend. Apr. 1, 2009;101(1-2):107-14. doi: 10.1016/j.drugalcdep.2008.11.013. Epub Dec. 31, 2008.
Zaman, et al. Bioequivalency and dose proportionality of three tableted promethazine products. Biopharm Drug Dispos. May-Jun. 1986;7(3):281-91.
Zenser, et al. Enzyme systems involved in the formation of reactive metabolites in the renal medulla: cooxidation via prostaglandin H synthase. Fundam Appl Toxicol. Dec. 1984;4(6):922-9.
Zhelev, et al. Phenothiazines suppress proliferation and induce apoptosis in cultured leukemic cells without any influence on the viability of normal lymphocytes. Phenothiazines and leukemia. Cancer Chemother Pharmacol. Mar. 2004;53(3):267-75. Epub Dec. 9, 2003.
Zimmerman, et al. Acetaminophen (paracetamol) hepatotoxicity with regular intake of alcohol: analysis of instances of therapeutic misadventure. Hepatology. Sep. 1995;22(3):767-73.
Caldwell, Jacques R., et al. Treatment of Osteoarthritis Pain with Controlled Release Oxycodone or Fixed Combination Oxycodone Plus Acetaminophen Added to Nonsteroidal Antiinflammatory Drugs: A double Blind, Randomized, Multicenter, Placebo Controlled Trial. Journal of Rheumatology, 26(4):862-869 (Apr. 1, 1999).
Co-pending U.S. Appl. No. 15/679,460, filed Aug. 17, 2017.
Co-pending U.S. Appl. No. 15/683,643, filed Aug. 22, 2017.
Co-pending U.S. Appl. No. 15/683,646, filed Aug. 22, 2017.
Flake, Z.A. et al. Practical Selection of Antiemetics, Am. Fam. Physician, 69(5):1169-1176 (Mar. 1, 2004).
Kawahara, Y. et al. Headache medication / Dizziness treatment. The Journal of Practical Pharmacy (Yakkyoku), 2007, vol. 58, No. 4, pp. 605 - 616.
Khalil, S. et al. Ondansetron/Promethazine Combination or Promethazine Alone Reduces Nausea and Vomiting After Middle Ear Surgery, Journal of Clinical Anesthesia, 11:596-60 (Nov. 1999).
Promethazine HCl and Hydrocodone Bitartrate Syrup Proposed Labeling. Attachment C. WraSer Pharmaceuticals. Dated Mar. 7, 2007, pp. 1-8.
U.S. Appl. No. 14/683,886 Final Office Action dated May 10, 2017.
U.S. Appl. No. 14/789,883 Notice of Allowance dated Jul. 3, 2017.
U.S. Appl. No. 14/789,883 Supplemental Notice of Allowability dated Aug. 1, 2017.
U.S. Appl. No. 14/930,496 Notice of Allowability dated Aug. 4, 2017.
U.S. Appl. No. 14/930,496 Notice of Allowance dated Jun. 20, 2017.
U.S. Appl. No. 14/930,496 Supplemental Notice of Allowability dated Jul. 12, 2017.
U.S. Appl. No. 15/263,235 Final Office Action dated Jul. 3, 2017.
U.S. Appl. No. 15/346,541 Non-Final Office Action dated Aug. 23, 2017.
Anonymous, NCT01780428 on Jan. 30, 2013: ClinicalTrials.gov Archive, Retrieved from the internat: URL:https://clinicaltrials.gov/archive/NCT01780428/2013_01_30 [retieved on Oct. 23, 2017]. pp. 1-3 .
Anonymous: Strong Efficacy Data Promp Charleston Laboratories to Halt Phase 3 Study of CL-108 in Patients with Moderate to Severe Acute Pain, Oct. 29, 2013. {Retrieved from the internet: URL:http://Charlestonlabs.com/wp-content/uploads/CL-108-Ph3-Top-Line-Al.pdf [Retrieved on Oct. 23, 2017, pp. 1-2].
Chia, et al. (Abstract of Acta Anaesthesiol Scand. 2004:48(5):625-630) 2 pages (year: 2004).
IMS Institute for Healthcare Informatics. Medicines Use and Spending in the U.S.: A Review of 2015 and Outlook to 2020. Parsippany, NJ: IMS Institute for Healthcare Informatics; 2016.
Kottschade, L. et al. Chemotherapy-induced nausea and vomiting: incidence and characteristics of persistent symptoms and future directions NCCTG N08C3 (Alliance). Support Care Cancer. 2016;24(6):2661-2667.
National Institutes of Health. Fact Sheets: Pain Management. http://report.nih.gov/nihfactsheets/ViewFactSheet.aspx?csid=57. Accessed Jun. 8, 2017.
Nicholson BD. Economic and clinical burden of opioid-induced nausea and vomiting. Postgrad Med. 2017;129(1):111-117.
Schachtel, B. et al. Demonstration of the safety and efficacy of CL-108 for moderate-to-severe pain with reduction of opioid-induced nausea and vomiting, Journal of Pain, 15(4):581 (Apr. 2014) .
Smith HS, Smith EJ, Smith BR. Postoperative nausea and vomiting. Ann Palliat Med. 2012;1(2):94-102.
U.S. Appl. No. 14/683,886 Final Office Action dated Oct. 30, 2017.
U.S. Appl. No. 15/263,230 Final Office Action dated Oct. 23, 2017.
U.S. Appl. No. 15/263,243 Notice of Allowability dated Oct. 18, 2017.
U.S. Appl. No. 15/263,243 Notice of Allowance dated Oct. 4, 2017.
U.S. Appl. No. 15/683,643 Non-Final Office Action dated Oct. 5, 2017.
U.S. Appl. No. 15/263,235 Non-Final Office Action dated Feb. 23, 2018.
U.S. Appl. No. 15/679,460 Non-Final Office Action dated Feb. 9, 2018.
International Application No. PCT/US2016/056910, International Preliminary Report on Patentability dated Apr. 17, 2018.
U.S. Appl. No. 14/099,432 Final Office Action dated May 11, 2018.
U.S. Appl. No. 14/683,886 Final Office Action dated Jun. 6, 2018.
U.S. Appl. No. 15/263,230 Non-Final Office Action dated Jul. 2, 2018.
U.S. Appl. No. 15/346,541 Notice of Allowance dated Apr. 17, 2018.
U.S. Appl. No. 15/683,643 Final Office Action dated Jun. 1, 2018.
U.S. Appl. No. 15/683,646 Final Office Action dated Jul. 3, 2018.

\* cited by examiner

A.

B.

PHARMACEUTICAL COMPOSITIONS

CROSS-REFERENCE

This application is a continuation of U.S. application Ser. No. 14/930,496, filed on Nov. 2, 2015, which is a continuation of U.S. application Ser. No. 14/036,946, filed on Sep. 25, 2013, now U.S. Pat. No. 9,226,901, which is a continuation of U.S. application Ser. No. 13/347,552, filed on Jan. 10, 2012, now U.S. Pat. No. 9,198,867, which is a continuation of U.S. application Ser. No. 12/351,704 filed on Jan. 9, 2009, now U.S. Pat. No. 8,124,126, which claims the benefit of U.S. Provisional Application Nos. 61/020,139 filed Jan. 9, 2008, 61/043,037 filed Apr. 7, 2008, and 61/060,758 filed Jun. 11, 2008, each of which is incorporated by reference herein in its entirety.

BACKGROUND OF THE INVENTION

Available pain medications may have adverse effects, such as nausea, vomiting, and skin rashes and sedation. As a result of such adverse effects, many subjects are unable to tolerate recommended dosages needed for effective pain relief because of adverse effects. Accordingly, there remains a need for effective therapeutics with reduced adverse effects.

SUMMARY OF THE INVENTION

Figure 1:
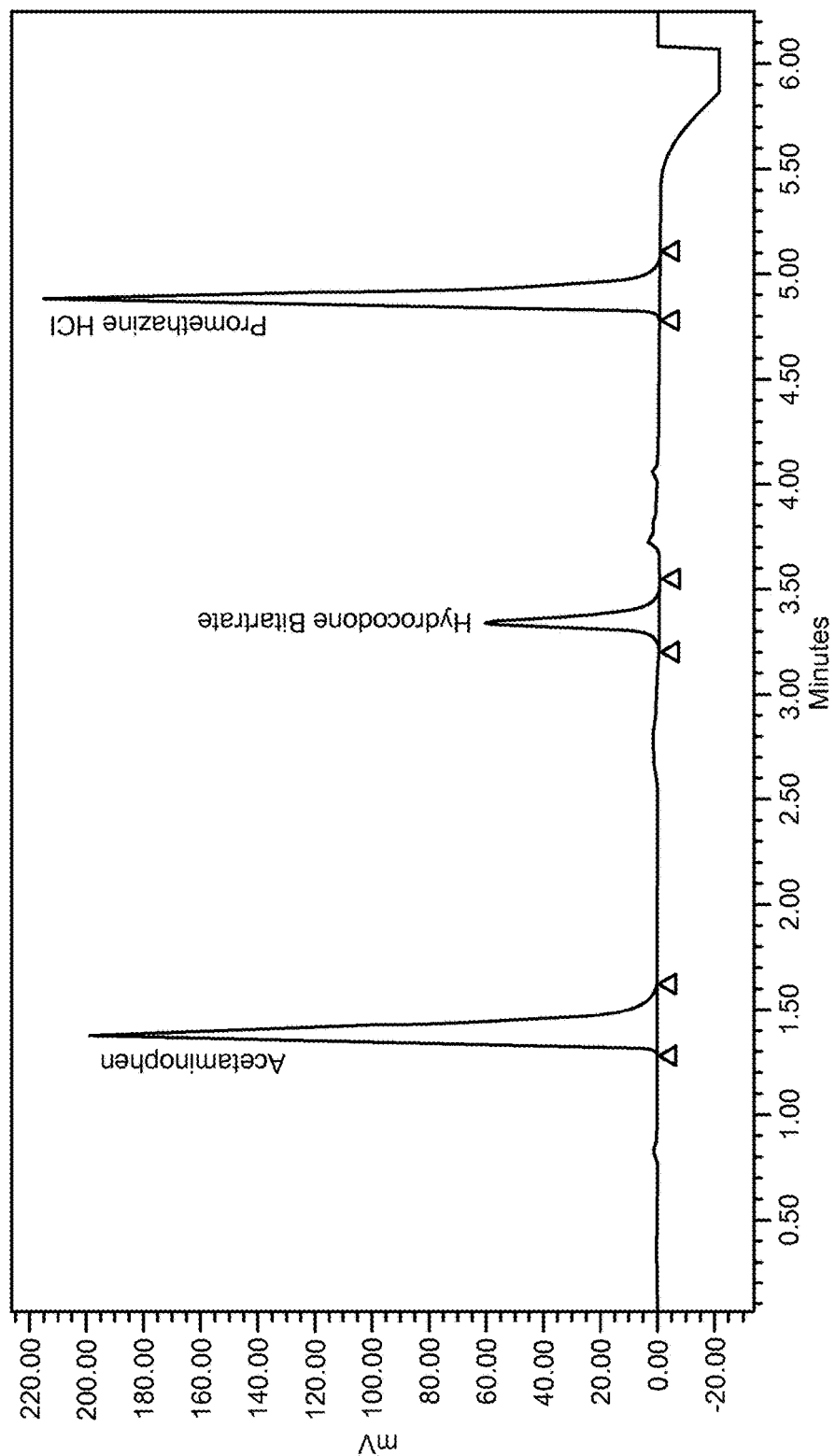
FIG. 1 illustrates a chromatograph for example of a standard solution.

In one embodiment this invention provides compositions comprising (1) an effective amount of: (a) an opioid analgesic; (b) a stimulant; (c) an antiemetic; and (2) a pharmaceutically acceptable carrier or vehicle.

In another embodiment this invention provides compositions comprising (1) an effective amount (a) oxycodone or a pharmaceutically acceptable salt thereof, (b) promethazine or a pharmaceutically acceptable salt thereof, (c) modafinil or a pharmaceutically acceptable salt thereof and (d) naltrexone or a pharmaceutically acceptable salt thereof; and (2) a pharmaceutically acceptable carrier or vehicle.

In another embodiment this invention provides compositions comprising (1) an effective amount of (a) morphine or a pharmaceutically acceptable salt thereof, (b) promethazine or a pharmaceutically acceptable salt thereof, and (c) modafinil or a pharmaceutically acceptable salt thereof; and (2) a pharmaceutically acceptable carrier or vehicle.

In another embodiment this invention provides compositions comprising an effective amount of butalbital or a pharmaceutically acceptable salt thereof, acetaminophen and promethazine or a pharmaceutically acceptable salt thereof; and a pharmaceutically acceptable carrier or vehicle.

In another embodiment this invention provides compositions comprising (1) an effective amount of (a) an opioid analgesic agent; (b) an anti-emetic agent and (c) a beta blocker, serotonin receptor agonist, vasoconstrictor, anti-platelet agent, anti-convulsant, triptan, ergot, or calcitonin-gene-related peptide receptor antagonist; and (2) a pharmaceutically acceptable carrier or vehicle.

In another embodiment this invention provides compositions comprising (1) an effective amount of (a) an opioid analgesic agent and (b) sumatriptan or a pharmaceutically acceptable salt thereof; and (2) a pharmaceutically acceptable carrier or vehicle.

In another embodiment this invention provides compositions consisting of (1) an effective amount of (a) sumatriptan or a pharmaceutically acceptable salt thereof and (b) promethazine or a pharmaceutically acceptable salt thereof; and (2) a pharmaceutically acceptable carrier or vehicle.

In another embodiment this invention provides compositions comprising (1) an effective amount of (a) an opioid analgesic agent, (b) a Cox-2 inhibitor agent, an anti-depressant agent, an anti-convulsant agent, an anti-cholinergic agent, an NMDA receptor antagonist agent, an anesthetic agent or an $\alpha_2$-adrenoreceptor agonist agent, (c) an opioid antagonist agent, (d) an agent that reduces or eliminates an adverse effect of the opioid agent; and (2) a pharmaceutically acceptable carrier or vehicle.

In another embodiment this invention provides compositions comprising (1) an effective amount of (a) an opioid analgesic agent, (b) a non-opioid analgesic agent, (c) cyclazacine or levallorphan; (d) an agent that reduces or eliminates an adverse effect of the opioid analgesic agent; and (2) a pharmaceutically acceptable carrier.

In another embodiment this invention provides a composition comprising (1) an effective amount of (a) an opioid analgesic agent, (b) a non-opioid analgesic agent, (c) an antiemetic; (d) an abuse deterrent agent; and (2) a pharmaceutically acceptable carrier. In one embodiment the abuse deterrent agent is niacin or a pharmaceutically acceptable salt thereof; zinc sulfate; or sodium lauryl sulfate.

In another embodiment this invention provides compositions comprising (1) an effective amount of (a) an opioid analgesic agent, (b) a non-opioid analgesic agent, (c) an opioid antagonist agent, (d) aprepitant, perphenazine, acetyl-leucine monoethanolamine, azasetron, benzquinamide, bietanautine, bromopride, clebopride, diphenidol, methallatal, metopimazine, oxyperndyl, pipamazine, sulpiride, thiethylperazine, thioproperazine, or a pharmaceutically acceptable salt thereof; and (2) a pharmaceutically acceptable carrier or vehicle.

In another embodiment this invention provides bi-layer tablets comprising: (1) a controlled-release layer comprising from about 6.5 mg to about 8.5 mg of hydrocodone or a pharmaceutically acceptable salt thereof; and from about 290 to about 360 mg of acetaminophen or a pharmaceutically salt; and (2) an immediate-release layer comprising from about 11 mg to about 14 mg of promethazine or a pharmaceutically salt thereof. In another embodiment this invention provides bilayer tablets comprising (1) an effective amount of (a) an opioid analgesic or a pharmaceutically acceptable salt thereof and (b) one or more antiemetic or a pharmaceutically acceptable salt thereof; and (2) a pharmaceutically acceptable carrier or vehicle.

In another embodiment this invention provides bilayer tablets comprising: (1) a controlled release layer comprising (a) from about 6.5 mg to about 8.5 mg of hydrocodone or a pharmaceutically acceptable salt thereof, (b) from about 290 to about 360 mg of acetaminophen or a pharmaceutically acceptable salt thereof, (c) from about 135 mg to about 170 mg of silicified microcrystalline cellulose, (d) from about 17 mg to about 23 mg of hydroxy methyl propyl cellulose, (e) from about 1 mg to about 4 mg of magnesium stearate, and (f) from about 1 mg to about 4 mg of stearic acid; and (2) an immediate release layer comprising (a) from about 11 mg to about 14 mg of promethazine or a pharmaceutically acceptable salt thereof, (b) from about 100 mg to about 140 mg of silicified microcrystalline cellulose, (c) from about 12 mg to about 18 mg of croscarmellose sodium and (d) from about 0.8 mg to about 1.5 mg of magnesium stearate.

In another embodiment this invention provides compositions comprising (1) an effective amount of (a) hydrocodone or a pharmaceutically acceptable salt thereof or oxycodone or a pharmaceutically acceptable salt thereof; (b) acetaminophen or a pharmaceutically acceptable salt thereof, (c) promethazine or a pharmaceutically acceptable salt thereof and (d) about 0.75 mg of naltrexone or a pharmaceutically acceptable salt thereof; and (2) a pharmaceutically acceptable carrier or vehicle.

In another embodiment this invention provides compositions consisting of (1) an effective amount of (a) oxycodone or a pharmaceutically acceptable salt thereof, (b) promethazine or a pharmaceutically acceptable salt thereof and (c) naltrexone or a pharmaceutically acceptable salt thereof; and (2) a pharmaceutically acceptable carrier or vehicle.

In another embodiment this invention provides compositions consisting of (1) an effective amount of (a) promethazine or a pharmaceutically acceptable salt thereof, (b) propoxyphene or a pharmaceutically acceptable salt thereof, (c) naproxen or a pharmaceutically acceptable salt thereof; and (2) a pharmaceutically acceptable carrier or vehicle.

In another embodiment this invention provides methods for treating or preventing pain, comprising administering to a subject in need thereof an effective amount of (a) an opioid analgesic agent, (b) an antiemetic agent or an antihistamine, and (c) a stimulant agent.

In another embodiment this invention provides methods for treating or preventing a migraine headache comprising administering to a subject in need thereof an effective amount of (a) an opioid analgesic agent; (b) an antiemetic agent; and (c) a stimulant agent.

In another embodiment this invention provides methods for treating or preventing a headache comprising administering to a subject in need thereof an effective amount of (a) an opioid analgesic agent; and (b) an antiemetic agent. In one embodiment the headache is a migraine headache, cluster headache or hemicrania continua headache. In another embodiment the headache is a chronic headache, tension headache or chronic tension headache.

In another embodiment this invention provides methods for treating pain, comprising administering to a subject in need thereof an effective amount of (a) an opioid analgesic agent, (b) an antiemetic agent; and (c) a non-opioid analgesic agent; wherein the subject is about 65 years of age or older.

In another embodiment this invention provides methods for treating or preventing photophobia comprising administering to a subject in need thereof an effective amount of (a) an opioid analgesic agent; and (b) an antiemetic agent. In one embodiment the photophobia is associated with migraine headache.

In another embodiment this invention provides methods for treating or preventing headache comprising: administering to a subject in need thereof (1) an effective amount of (a) triptan or a pharmaceutically acceptable salt thereof and (b) promethazine or a pharmaceutically acceptable salt thereof; and (2) a pharmaceutically acceptable carrier or vehicle. In one embodiment the triptan is sumatriptan. In another embodiment the headache is migraine headache.

In another embodiment this invention provides methods for treating or preventing pain comprising: administering to a subject in need thereof (1) an effective amount of (a) an opioid analgesic agent, (b) a Cox-2 inhibitor agent, an anti-depressant agent, an anti-convulsant agent, an anti-cholinergic agent, an NMDA receptor antagonist agent, an anesthetic agent or an $\alpha_2$-adrenoreceptor agonist agent, (c) an opioid antagonist agent, (d) an agent that reduces or eliminates an adverse effect of the opioid agent; and (2) a pharmaceutically acceptable carrier or vehicle.

In another embodiment this invention provides methods for treating or preventing pain comprising, administering to a subject in need thereof a bi-layer tablet comprising: (1) a controlled-release layer comprising from about 6.5 mg to about 8.5 mg of hydrocodone or a pharmaceutically acceptable salt thereof; and from about 290 to about 360 mg of acetaminophen or a pharmaceutically salt; and (2) an immediate-release layer comprising from about 11 mg to about 14 mg of promethazine or a pharmaceutically salt thereof.

In another embodiment this invention provides methods for treating or preventing pain comprising, administering to a subject in need thereof a bi-layer tablet comprising (1) an effective amount of (a) oxycodone or a pharmaceutically acceptable salt thereof and (b) promethazine or a pharmaceutically acceptable salt thereof; and (2) a pharmaceutically acceptable carrier or vehicle.

In another embodiment this invention provides methods for treating or preventing pain comprising, administering to a subject in need thereof a bi-layer tablet comprising: (1) a controlled release layer comprising (a) from about 6.5 mg to about 8.5 mg of hydrocodone or a pharmaceutically acceptable salt thereof, (b) from about 290 to about 360 mg of acetaminophen or a pharmaceutically acceptable salt thereof, (c) from about 135 mg to about 170 mg of silicified microcrystalline cellulose, (d) from about 17 mg to about 23 mg of hydroxy methyl propyl cellulose, (e) from about 1 mg to about 4 mg of magnesium stearate, and (f) from about 1 mg to about 4 mg of stearic acid; and (2) an immediate release layer comprising (a) from about 11 mg to about 14 mg of promethazine or a pharmaceutically acceptable salt thereof, (b) from about 100 mg to about 140 mg of silicified microcrystalline cellulose, (c) from about 12 mg to about 18 mg of croscarmellose sodium and (d) from about 0.8 mg to about 1.5 mg of magnesium stearate.

In another embodiment this invention provides methods for treating or preventing pain comprising, administering to a subject in need thereof composition consisting of (1) an effective amount of (a) promethazine or a pharmaceutically acceptable salt thereof, (b) propoxyphene or a pharmaceutically acceptable salt thereof, (c) naproxen or a pharmaceutically acceptable salt thereof; and (2) a pharmaceutically acceptable carrier or vehicle.

In one embodiment of the invention, a composition is in the form of a bilayer tablet, wherein the bilayer tablet comprises an immediate-release layer and a controlled-release layer, wherein each layer comprises one or more pharmaceutically active agents disclosed herein.

In yet another embodiment of the invention a bilayer tablet comprises an effective amount of an antiemetic and the antiemetic is capable of achieving from about 70% to about 80% dissolution in the stomach of a subject in about 5 to about 10 minutes following oral administration.

In another embodiment of the invention a bilayer tablet comprises an effective amount of an opioid analgesic, or a non-opioid analgesic, and the opioid analgesic or the non-opioid analgesic is capable of achieving from about 30% to about 60% dissolution in the stomach of a subject in about 5 to about 10 minutes following oral administration.

DETAILED DESCRIPTION OF THE INVENTION

All patents and publications and referred to herein are incorporated by reference in their entirety.

The invention is generally directed to compositions comprising multiple pharmaceutically active agents that are useful as therapeutics that alleviate, abate or eliminate one or more conditions in a subject in need thereof, as further described herein below.

An "effective amount" of when used in connection with composition of the invention is an amount sufficient to produce a therapeutic result in a subject in need thereof. For example a therapeutic result can include, but is not limited to, treating or preventing pain, nausea or vomiting by a subject.

An "effective amount" when used in connection with an opioid analgesic agent alone or in combination is an amount that is effective for treating or preventing pain, wherein the antagonist agent is provided in combination with one or more pharmaceutically active agents disclosed herein. In one embodiment, the one or more pharmaceutically active agent is an antiemetic.

An "effective amount" when used in connection with an antiemetic agent is an amount that is effective for preventing or reducing or eliminating one or more adverse effects associated with one or more pharmaceutically active agent disclosed herein. In various embodiments, the one or more pharmaceutically active agent includes but is not limited to an opioid analgesic and/or a non-opioid analgesic.

In further embodiments, such adverse effects which are reduced, prevented or eliminated include but are not limited to incidence of nausea or vomiting. Furthermore, an "effective amount" when used in connection with an antihistamine is an amount that is effective for preventing or reducing the incidence of nausea or vomiting, or preventing or reducing adverse effects associated with an opioid analgesic (e.g., opioid-induced nausea and vomiting).

An "effective amount" when used in connection with a stimulant agent is an amount that is effective to increase alertness, or lessen soporific effects of an opioid agent, wherein the stimulant agent is present in a dosage formulation alone or in combination with one or more pharmaceutically active agent disclosed herein. In various embodiments, the one or more pharmaceutically active agent includes but is not limited to an antiemetic agent, and a barbiturate.

An "effective amount" when used in connection with a barbiturate agent is an amount that is effective for treating or preventing pain, producing a sedative effect, anesthetic effect or calming effect when provided alone or in combination with one or more pharmaceutically active agent disclosed herein. In various embodiments, the one or more pharmaceutically active agent includes but is not limited to an opioid analgesic, a non-opioid analgesic, antiemetic or combination thereof.

An "effective amount" when used in connection with a opioid antagonist agent is an amount that is effective for preventing or inhibiting abuse of a dosage form comprising an opioid analgesic agent, wherein the antagonist agent is provided in combination with one or more pharmaceutically active agent disclosed herein. In various embodiments, the one or more pharmaceutically active agent includes but is not limited to an opioid agent, a non-opioid analgesic, a stimulant, a barbiturate, or a combination thereof.

An "effective amount" when in used in connection with one or more of the agents disclosed herein is the total amount of one or more of the agents that is useful for the treatment of pain.

The term "about" means the referenced numeric indication plus or minus 10% of that referenced numeric indication.

Pharmaceutically active agents disclosed herein are capable of use in a composition of the invention. A pharmaceutically active agent, such as an opioid analgesic agent, non-opioid analgesic agent, antitussive agent, antiemetic agent, antihistamine, a stimulant, or a barbiturate, can be in the form of a pharmaceutically acceptable salt thereof.

In some embodiments of the invention a composition comprises an analgesic agent (e.g., one analgesic or two, three or more analgesics) and agent (e.g., one, two or more of an antihistamine or antiemetic) that reduces or eliminates an adverse effect of an analgesic agent. In various embodiments, a composition of the invention comprises one or more pharmaceutically active agents provided in Table 1 or Table 2, or a pharmaceutically acceptable salt thereof.

In one embodiment, a composition comprise, an effective amount of an opioid analgesic agent, an effective amount of non-opioid analgesic agent, and an effective amount of an agent that reduces or eliminates an adverse effect of an analgesic agent.

In another embodiment of the invention a composition comprises an antiemetic and about 70 to about 80% of the antiemetic dissolves in the stomach of a subject after about 5 to about 10 minutes following oral administration. In one embodiment, about 100% of the antiemetic dissolves in the stomach of a subject about 40, about 50 or about 60 minutes following oral administration. In one embodiment, the antiemetic is promethazine or a pharmaceutically acceptable salt thereof. In another embodiment, the promethazine salt is promethazine HCl.

In another embodiment of the invention a composition comprises an opioid analgesic and from about 30% to about 40% of the opioid analgesic dissolves in the stomach of a subject after about 5 to about 10 minutes following oral administration. In one embodiment, about 100% of the opioid analgesic dissolves in the stomach of a subject about 40, about 50 or about 60 minutes following oral administration. In one embodiment, the opioid analgesic is hydrocodone, oxycodone or a pharmaceutically acceptable salt thereof. In another embodiment, the hydrocodone salt is hydrocodone bitartrate; or the oxycodone salt is oxycodone HCl.

In one embodiment, compositions of the invention are administered to a subject at about every 4 to about 6 hours, about every 12 hours, or about every 24 hours. In one embodiment, a composition of the invention is administered once daily.

In one embodiment, the agent that reduces or eliminates an adverse effect is an antiemetic agent or antihistamine. In further embodiments, the adverse effect reduced or eliminated is associated with an opioid analgesic. In an additional embodiment, the adverse effect is associated with a non-opioid analgesic.

In various embodiments, an agent that reduces or eliminates an adverse effect of an opioid analgesic agent or a non-opioid analgesic agent includes but is not limited to promethazine, dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, *cannabis*, dronabinol, nabilone, midazolam, lorazepam, hyoscine, dexamethasone, trimethobenzamide, emetrol, and propofol or a pharmaceutically acceptable salt thereof.

In one embodiment, a composition of the invention comprises a non-opioid analgesic agent which is acetaminophen, ibuprofen, naproxen or flurbiprofen, or a pharmaceutically acceptable salt thereof. In one embodiment the agent is naproxen sodium or magnesium.

In one embodiment, the opioid analgesic agent is hydrocodone or oxycodone, or a pharmaceutically acceptable salt thereof thiosemicarbazone, p-nitrophenylhydrazine, o-methyloxime, semicarbazone, or bis (methylcarbamate) derivative, (each of the foregoing being an opioid analgesic agent or derivative). In a further embodiment, the opioid analgesic agent is hydrocodone bitartrate or oxycodone hydrochloride.

In another embodiment the opioid analgesic agent is a naturally occurring opiate, such as an alkaloid occurring in the opium poppy. In one embodiment the naturally occurring opiate is morphine, codeine, narcotine, papaverine, narceine, thebaine; or a pharmaceutically acceptable salt thereof.

In one embodiment, a composition comprises an effective amount of each of an opioid analgesic, a non-opioid analgesic and an antiemetic or antihistamine, wherein the composition is capable of providing an effective plasma concentration of the antihistamine prior to an effective plasma concentrations of the opioid and the non-opioid analgesic, post oral administration. For example, a composition comprising an effective amount of each of an opioid analgesic, non-opioid analgesic, and an antihistamine or antiemetic—provides an effective plasma concentration of the latter antihistamine or antiemetic in about 1 to about 20 minutes, which is substantially earlier than effective plasma concentration of an analgesic, which can be from about 20 minutes to about 12 hours. In one embodiment of the invention, a composition comprises an effective amount of each of one or more pharmaceutically active agents disclosed herein. In one embodiment, the composition is a bilayer tablet comprising a controlled-release layer and an immediate-release layer.

In one embodiment about 70% to about 80% of a pharmaceutically active agent is capable of achieving dissolution from the immediate-release layer at about 5 to about 10 minutes following oral administration. In another embodiment about 70% to about 80% of a pharmaceutically active agent is capable of achieving dissolution from the immediate-release layer at about 5 to about 10 minutes following contact with a dissolution fluid, such as the dissolution fluid described in Example 15.

In another embodiment about 100% of a pharmaceutically active agent is capable of achieving dissolution from the immediate-release layer at about 40 minutes following oral administration. In another embodiment about 100% to of a pharmaceutically active agent is capable of achieving dissolution from the immediate-release layer at about 40 minutes following contact with a dissolution fluid, such as the dissolution fluid described in Example 15.

In another embodiment about 30% to about 40% of a pharmaceutically active agent is capable of achieving dissolution from the controlled-release layer at about 5 to about 10 minutes following oral administration. In another embodiment about 30% to about 40% of a pharmaceutically active agent is capable of achieving dissolution from the controlled-release layer at about 5 to about 10 minutes following contact with a dissolution fluid, such as the dissolution fluid described in Example 15.

In another embodiment about 90% of a pharmaceutically active agent is capable of achieving dissolution from the controlled-release layer at about 60 minutes following oral administration. In another embodiment about 90% of a pharmaceutically active agent is capable of achieving dissolution from the controlled-release layer at about 60 minutes following contact with a dissolution fluid, such as the dissolution fluid described in Example 15.

In yet another embodiment, from about 90 to about 100% of a pharmaceutically active agent is capable of achieving dissolution from the immediate-release layer at about 40, about 50 or about 60 minutes following oral administration. In yet another embodiment, from about 90 to about 100% of a pharmaceutically active agent is capable of achieving dissolution from the immediate-release layer at about 40, about 50 or about 60 minutes following contact with a dissolution fluid, such as the dissolution fluid described in Example 15.

Figure 5:
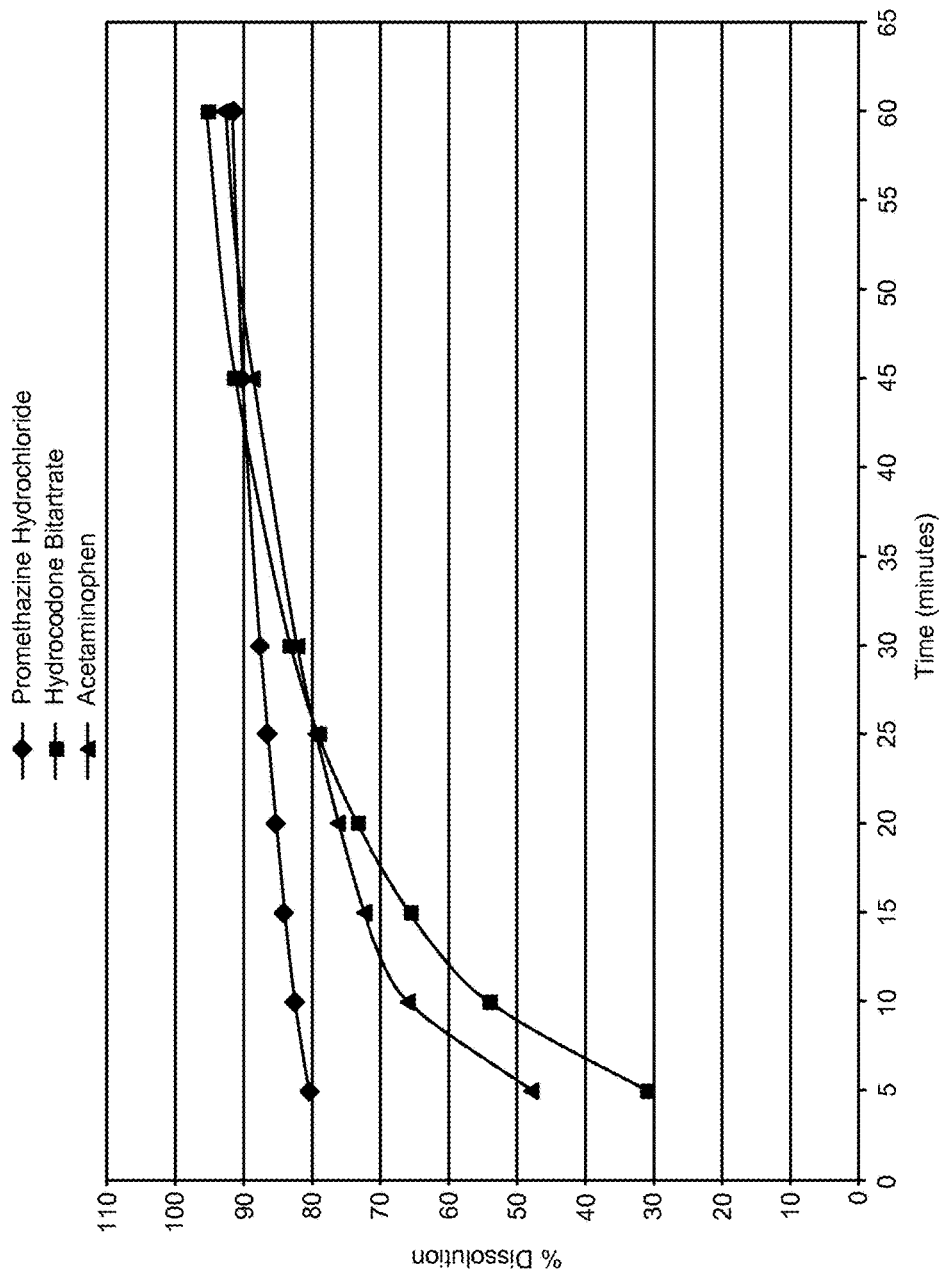
FIG. 5 illustrates an example of dissolution release profile for a composition of the invention.

In yet another embodiment, from about 90 to about 100% of a pharmaceutically active agent is capable of achieving dissolution from the controlled-release layer at about 40, about 50 or about 60 minutes following oral administration. In yet another embodiment, from about 90 to about 100% of a pharmaceutically active agent is capable of achieving dissolution from the controlled-release layer at about 40, about 50 or about 60 minutes following contact with a dissolution fluid, such as the dissolution fluid described in Example 15. An illustrative dissolution profile for a composition of the invention is depicted in FIG. 5.

In various embodiments, the composition is in the form of any oral dosage form disclosed herein, including but not limited to a pill, tablet, or capsule. In one embodiment, the composition is in the form of a bilayer tablet having an immediate-release layer and a controlled-release layer, wherein one or more pharmaceutically active agents are present in the immediate-release layer and one or more pharmaceutically active agents are present in the controlled release layer. In another embodiment, the immediate-release layer comprises one or more antiemetic, and the controlled-release layer comprises one or more pharmaceutically active agents disclosed herein, but which are not an antiemetic or antihistamine. In a further embodiment, an antiemetic or antihistamine is present in both the immediate-release and controlled-release layer. In another embodiment, the immediate release layer comprises promethazine or a pharmaceutically acceptable salt thereof. In another embodiment, the promethazine salt is promethazine HCl. In another embodiment, the controlled-release layer comprises an opioid analgesic. In a further embodiment, the opioid analgesic is hydrocodone or oxycodone, or a pharmaceutically acceptable salt thereof. In one embodiment the hydrocodone salt is hydrocodone bitartrate. In another embodiment, the oxycodone salt is oxycodone HCl. In a further embodiment, the controlled-release layer further comprises one or more non-opioid analgesic. In one embodiment, the non-opioid analgesic is acetaminophen or a pharmaceutically acceptable salt thereof. In one embodiment, the composition is in a form that achieves a hardness of from about 5 to about 15 kiloponds and has a thickness of about 5, about 5.5, about 6, about 6.5, about 7, about 7.5, about 8, about 8.5, about 9, about 9.5 or 10 mm. In one embodiment, the tablet has a hardness of about 9.5 kiloponds. In another embodiment, the tablet has a hardness of about 12.5 kiloponds. It will be understood that as to the kilopond and thickness measurements, increments of 0.1 decimal points are within the scope of the invention.

In one embodiment, the composition is capable of providing an effective plasma concentration of an antiemetic in about 1 minute to about 20 minutes after administration to a subject. In another embodiment, the antiemetic is promethazine or a pharmaceutically acceptable salt thereof. In a further embodiment the salt is promethazine HCl.

In various embodiments, a composition comprises from about 1% to about 20% by weight of an antihistamine; from about 10% to about 80% by weight a non-opioid analgesic; and from about 1% to about 20% by weight of an opioid analgesic. In some embodiments, the antihistamine is promethazine, dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, *cannabis*, dronabinol, nabilone, midazolam, lorazepam, hyoscine, dexamethasone, trimethobenzamide, emetrol, or propofol, or pharmaceutically acceptable salt thereof.

In one embodiment, the composition is capable providing an effective plasma concentration of promethazine or a pharmaceutically acceptable salt thereof in about 1 minute to about 20 minutes after administration to a subject.

In one embodiment, a method is provided for reducing or eliminating an adverse effect of an analgesic agent, comprising administering to a subject in need thereof a composition comprising an effective amount of each of an opioid analgesic agent, a non-opioid analgesic agent and an agent which reduces or eliminates a adverse effect of the analgesic agents.

In one embodiment, a method is provided for treating or preventing pain, comprising administering to a subject in need thereof an effective amount of a composition comprising an effective amount of each of an opioid analgesic, or a pharmaceutically acceptable salt thereof, a non-opioid analgesic, or a pharmaceutically acceptable salt thereof, and an agent which reduces a adverse effect associated with the opioid or non-opioid analgesic agent. In one embodiment, the agent that reduces an adverse effect is an antiemetic or an antihistamine.

In another embodiment the pain is associated with cancer, chronic or acute pain, a headache, chronic headache, a migraine headache, a surgical procedure, acute or chronic physical injury, bone fracture or a crush injury, spinal cord injury, an inflammatory disease (e.g., pancreatitis), a non-inflammatory neuropathic or dysfunctional pain condition, or a combination thereof. In one embodiment the subject is a mammal, e.g., a human, mouse, rat, guinea pig, dog, cat, horse, cow, pig, or non-human primate, such as a monkey, chimpanzee or baboon. In one embodiment, the subject is a human. In one embodiment a stimulant that has anti-sedative properties, which can bring pain relief to the subject with reduced sedative effects common to some opioid analgesic formulations.

In some embodiments, the agent useful for reducing or eliminating an adverse effect associated with administration of an opioid or non-opioid analgesic agent, is promethazine, dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, *cannabis*, dronabinol, nabilone, midazolam, lorazepam, hyoscine, dexamethasone, trimethobenzamide, emetrol, or propofol, or pharmaceutically acceptable salt thereof.

A composition can be in any form disclosed herein, such as a multi-layer tablet (e.g., a bi-layer tablet). In one embodiment, the multi-layer tablet is a bi-layer tablet that comprises: (a) an immediate-release layer that comprises an effective amount of an agent which reduces or eliminates an adverse effect of an opioid analgesic; and (b) a controlled-release layer that comprises an effective amount of each of an opioid analgesic agent and a non-opioid analgesic agent.

In one embodiment, the agent that reduces or eliminates an adverse effect associated with administration of an opioid or non-opioid analgesic agent is released in a subject at a substantially faster rate than an opioid or non-opioid analgesic in a composition of the invention. For example, in one embodiment, a plasma concentration of the agent that reduces or eliminates an adverse effect of an opioid analgesic is achieved in about 1 minute to about 20 minutes following oral administration, as compared with a plasma concentration of an analgesic agent, which can be achieved in about 30 minutes to about 8 hours following oral administration. In various embodiments, the compositions of the invention comprise an agent that reduces or eliminates an adverse effect associated with administration of an opioid analgesic or non-opioid analgesic, where the agent provides an effective plasma concentration in about 1 minute to about 20 minutes following oral administration.

In one embodiment, the agent that reduces or eliminates an adverse effect associated with an opioid or a non-opioid analgesic is an antihistamine or antiemetic. In various embodiments, As indicated above, compositions can comprise an antiemetic agent including, for example, aprepitant, dronabinol, perphenazine, palonosetron, trimethobenzamide, metoclopramide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, *cannabis*, midazolam, lorazepam, hyoscine, dexamethasone, emetrol, propofol and a pharmaceutically acceptable salt or mixtures thereof.

In one embodiment, a composition comprises an effective amount of an opioid analgesic agent, a non-opioid analgesic agent, and an agent that reduces or eliminates an adverse effect associated with administration of the opioid or non-opioid analgesic. An adverse effect of opioid or non-opioid analgesic agents includes but is not limited to nausea, vomiting, other gastric upset, skin rash, an allergic reaction such as swelling, difficulty breathing, closing of throat, abdominal pain, unusual bleeding or bruising, sedation, CNS depression, or respiratory depression. In one embodiment, the adverse effect that is reduced or eliminated is nausea, vomiting, constipation, or a combination thereof.

In a further embodiment, the opioid analgesic agent is, for example, hydrocodone, oxycodone propoxyphene, or fentanyl, or a pharmaceutically acceptable salt thereof; the non-opioid analgesic agent is, for example, acetaminophen, ibuprofen, ketoprofen, naproxen, or aspirin or a pharmaceutically acceptable salt thereof; and the agent useful for preventing and/or suppressing an adverse effect is, for example, an antihistamine such as promethazine or a pharmaceutically acceptable salt thereof. In one embodiment of the invention, the pharmaceutically acceptable salt of naproxen is naproxen sodium.

In one embodiment an opioid analgesic agent, a non-opioid analgesic agent and an agent that reduces or eliminates an adverse effect are formulated in a bi-layer tablet.

Figure 2:
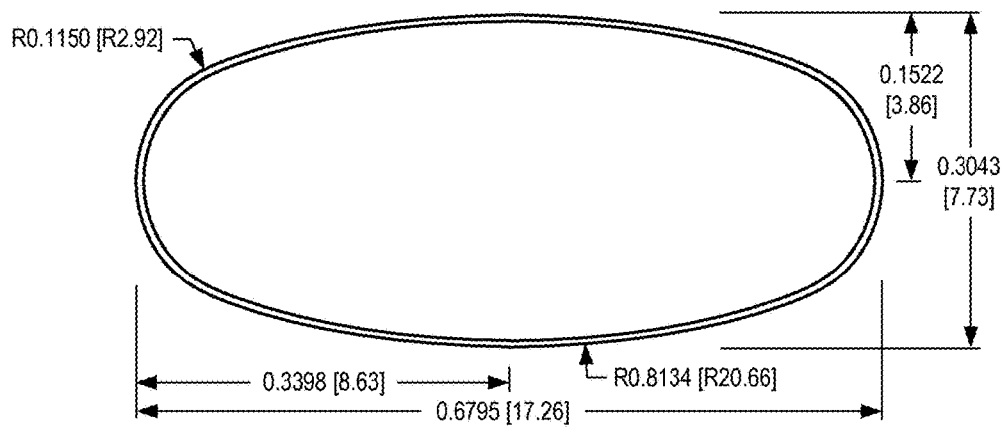
FIG. 2 illustrates one embodiment of a tablet of the invention. A. Illustrates a top view of the tablet (numerals in square brackets refer to measurements in millimeters and numerals not in square brackets are in inches); B. illustrates a side view of the tablet (numerals in square brackets refer to measurements in millimeters and numerals not in square brackets are in inches).
Figure 2:
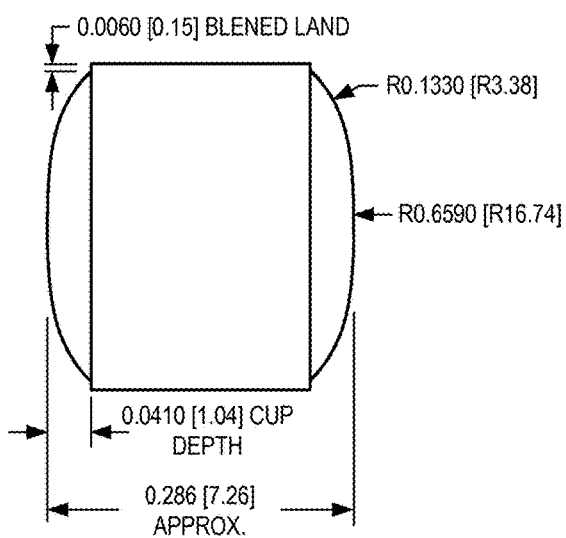

In one embodiment the bi-layer tablet comprises an immediate-release layer and a controlled-release layer. In another embodiment, the immediate-release layer comprises one or more pharmaceutically active agent disclosed in Table 1 or Table 2 and the control release layer comprise one or more pharmaceutically active agents disclosed in Table 1 or Table 2. In a further embodiment, the immediate-release layer comprises an antiemetic or antihistamine and the controlled-release layer comprises an opioid analgesic, a barbiturate, a stimulant, a triptan or a combination thereof. An illustrative bilayer tablet is depicted in FIG. 2. In one embodiment, a bilayer tablet of the invention has the dimensions as depicted in FIG. 2.

In another embodiment the compositions comprise an effective amount of each of an analgesic agent, an antitussive agent, and an agent that reduces or eliminates an adverse effect of the analgesic agent or the antitussive agent. Under some embodiments the antitussive is also an analgesic.

In some embodiments the compositions comprise acetaminophen, hydrocodone or oxycodone, or a pharmaceutically acceptable salt thereof; and an antitussive agent such as dolasetron, domperidone, meclizine, dronabinol, a benzodiazepine, an anticholinergic, hydrocodone or oxycodone, or a pharmaceutically acceptable salt thereof.

In a further embodiment of this invention, the opioid analgesic agent is, for example, hydrocodone, or oxycodone or a pharmaceutically acceptable salt thereof; the non-opioid analgesic agent is, for example, acetaminophen, ibuprofen, ketoprofen, naproxen, lidocaine, or aspirin or a pharmaceutically acceptable salt thereof; the antiemetic agent is, for example 5-$HT_3$ receptor antagonist, a dopamine antagonist, an antihistamine, a cannabinoid, benzodiazepines, an anticholinergic, wherein all or less than all of the total amount of the antiemetic agent is formulated for immediate-release.

Another embodiment of this invention is directed to methods for the treatment of pain, comprising administering an effective amount of each of an opioid analgesic agent, a non-opioid analgesic agent and an agent that reduces or eliminates an adverse effect of the opioid analgesic agent to a subject in need thereof.

The methods allow for use of analgesics in populations at risk of adverse effect such as nausea, vomiting, other gastric upsets, skin rashes, allergic reactions such as swelling, difficulty breathing, closing of throat, abdominal pain, unusual bleeding or bruising, skin rashes, sedation, CNS depression, or respiratory depression.

In one embodiment, the compositions comprise an effective amount of each of an opioid analgesic, an antiemetic, and an opioid antagonist, the composition is capable of providing protection from a metabolic consequence of vomiting, particularly severe vomiting, in a subject particularly prone to adverse effects associated with an opioid analgesic. An example of metabolic consequence of vomiting is dehydration. In a further embodiment, the subject administered a composition of the invention is about 55 years of age or older, about 60 years of age or older, about 65 years of age or older, or about 70 years of age or older. In one embodiment, the composition administered to such a subject comprises an opioid analgesic and one or more antiemetic agent.

In one embodiment, the composition comprises oxycodone, promethazine, and naltrexone, or a pharmaceutically acceptable salt thereof.

In various embodiments, a dosage form of the invention provides an effective plasma concentration of an antiemetic or antihistamine at from about 1 minute to about 20 minutes after administration, such as about 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min. In some embodiments, the release rate occurs at substantially faster as compared with release rates for the analgesic agents. Therefore, in one embodiment, after administration to a subject, the antihistamine (e.g., promethazine dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, *cannabis*, dronabinol, nabilone, midazolam, lorazepam, hyoscine, dexamethasone, trimethobenzamide, emetrol or propofol, or a pharmaceutically acceptable salt thereof) is released or an effective plasma concentration of an antihistamine or antiemetic is achieved before release of the opioid or non-opioid analgesic.

In some embodiments, a dosage form of the invention provides an effective plasma concentration of said opioid analgesic or said non-opioid analgesic at from about 20 minutes to about 24 hours after administration, such as about 20 minutes, 30 minutes, 40 minutes, 50 minutes, 1 hr, 1.2 hrs, 1.4 hrs, 1.6 hrs, 1.8 hrs, 2 hrs, 2.2 hrs, 2.4 hrs, 2.6 hrs, 2.8 hrs, 3 hrs, 3.2 hrs, 3.4 hrs, 3.6 hrs, 3.8 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 23 hrs, or 24 hrs following administration.

In further embodiments, the opioid or non-opioid analgesic is present in an effective plasma concentration in a subject from about 1 hour to 24 hour or 1 day to 30 days, including but not limited to 1, 2, 3, 4, 5, 6, 7, 8, 9, 10, 12, 12, 13, 14, 15, 16, 17, 18, 19, 20, 21, 22, 23, 24, 25, 26, 27, 28, 29 or 30 days. In addition, administration of dosage compositions can be effected through patch delivery systems which are known in the art.

In one embodiment compositions comprise an effective amount of each of an opioid analgesics, a non-opioid analgesic agent, an antihistamine, anti-psychotic, anti-anxiety agent, or other CNS depressant is administered a reduced dosage of one or lessen and adverse effect (e.g. CNS depression). In another embodiment the dosage of one or more of pharmaceutically active agents is adjusted according to the severity of the pain and the response of the subject.

In subjects having a terminal disease or chronic condition, pain management can be of a primary concern to the subject's quality of life.

In some of these subjects tolerance to opioid analgesics can develop with continued use. In one embodiment, adjustments are made to the amounts or time-release characteristics of the component of a composition, such as a composition comprising an effective amount of each of an opioid analgesic, a non-opioid analgesic and an antihistamine. In this embodiment the adjustments can provide pain relief to a subject with tolerance to opioid analgesics. In one embodiment the amount of the opioid analgesic may be increased in the composition. In another embodiment the time release characteristics of the opioid analgesic may be adjusted so as to change the ratio of immediate-release opioid analgesic to controlled-release opioid analgesic.

In one embodiment, the compositions comprise: hydrocodone, oxycodone, or a pharmaceutically acceptable salt thereof, in a dosage range of from about 1.0 mg to about 200 mg; acetaminophen or a pharmaceutically acceptable salt thereof in a dosage range of from about 200 mg to about 1000 mg; and, promethazine or a pharmaceutically acceptable salt thereof in a dosage range of from about 0.5 mg to about 100 mg.

In another embodiment, a compositions comprises: oxycodone or a pharmaceutically acceptable salt thereof in a dosage range of from about 10 mg to about 80 mg; Naltrexone or a pharmaceutically acceptable salt thereof in a dosage range of from about 0.5 mg to about 0.75 mg; and, promethazine or a pharmaceutically acceptable salt thereof in a dosage range of from about 12.5 mg to about 50 mg.

In yet another embodiment, the compositions comprises: oxycodone or a pharmaceutically acceptable salt thereof in a dosage range of from about 10 mg to about 80 mg; and promethazine or a pharmaceutically acceptable salt thereof in a dosage range of from about 12.5 mg to about 50 mg. These compositions can be formulated using conventional technologies to provide for an extended time release over a desired dosage interval, such as 4 hours, 6 hours, 9 hours, 12 hours, or 24 hours. In another embodiment, the compositions comprise about 7.5 mg of hydrocodone, about 325 mg of acetaminophen or a pharmaceutically acceptable salt thereof, and about 12.5 mg of promethazine or a pharmaceutically acceptable salt thereof.

In another embodiment, the compositions comprise about 7.5 mg of oxycodone or a pharmaceutically acceptable salt thereof, about 325 mg of acetaminophen or a pharmaceutically acceptable salt thereof, and about 12.5 mg of promethazine or a pharmaceutically acceptable salt thereof.

In another embodiment compositions comprise an effective amount of hydrocodone or oxycodone, or a pharmaceutically acceptable salt thereof; an effective amount of acetaminophen or a pharmaceutically acceptable salt thereof; and an effective amount of promethazine or a pharmaceutically acceptable salt thereof, combined in a single, oral pill, tablet or lollipop, form having dosage levels that can be safely doubled for combating severe pain.

In a further embodiment all or less than the entire total amount of the promethazine or a pharmaceutically acceptable salt thereof is formulated for immediate-release into the subject's blood stream.

In a further embodiment all or less than the entire amount of the hydrocodone or oxycodone, or a pharmaceutically acceptable salt thereof is formulated for controlled-release into the subject's body.

In various embodiments, the agents are formulated as a dosage form (e.g., tablet, capsule, gel, lollipop), parenteral, intraspinal infusion, inhalation, nasal spray, transdermal patch, iontophoresis transport, absorbing gel, liquid, liquid tannate, suppositories, injection, I.V. drip, other formulation, or a combination thereof to treat subjects.

In another embodiment, the agents are formulated as single oral dosage form such as a tablet, capsule, cachet, soft gelatin capsule, hard gelatin capsule, extended release capsule, tannate tablet, oral disintegrating tablet, multi-layer tablet, effervescent tablet, bead, liquid, oral suspension, chewable lozenge, oral solution, lozenge, lollipop, oral syrup, sterile packaged powder including pharmaceutically-acceptable excipients, other oral dosage forms, or a combination thereof.

In another embodiment a composition of the invention comprises an agent in immediate-release, quick release, controlled-release, extended release, other release formulations or patterns, or a combination thereof.

In one embodiment, a composition of the invention comprises three active agents, such as a decongestant, an antitussive, an expectorant, a mucus-thinning drug, an analgesic or an antihistamine. For example, in one embodiment one of the agents is an antitussive such as, e.g., codeine, dihydrocodeine, hydrocodone, dextromethorphan, dextrorphan, or a pharmaceutically acceptable salt thereof; the other agent is a decongestant such as, e.g., phenylephrine, pseudoephedrine, or a pharmaceutically acceptable salt thereof; and the other agent is an expectorant. One will recognize that an active agent may fit into more than one category (e.g., hydrocodone is an antitussive and opioid analgesic).

In any of the embodiments disclosed herein, a composition of the invention can be administered using one or more different dosage forms which are further described herein. For example, a composition comprising multiple active agents can be administered in solid, semi-solid, microemulsion, gel, patch or liquid form. Such dosage forms are further described herein. Examples of such dosage forms are known, such as tablet forms disclosed in U.S. Pat. Nos. 3,048,526, 3,108,046, 4,786,505, 4,919,939, 4,950,484; gel forms disclosed in U.S. Pat. Nos. 4,904,479, 6,482,435, 6,572,871, 5,013,726; patches for delivery of pharmaceutical compositions such as those disclosed in U.S. Pat. Nos. 5,741,510, 4,624,665, 4,626,539, 4,834,978, 6,469,227, 5,919,479, 6,261,595, 6,303,142, 6,341,387, 6,465,006, 6,613,350, 6,780,426, 7,094,228, 6,756,053; capsule forms disclosed in U.S. Pat. Nos. 4,800,083, 4,532,126, 4,935,243, 6,258,380; liquid forms disclosed in U.S. Pat. Nos. 4,625, 494, 4,478,822, 5,610,184; or I.V. forms disclosed in U.S. Pat. Nos. 4,871,353, 4,925,444, 5,484,406; each of which is incorporated herein by reference in its entirety.

Immediate-release refers to the release of an active agent substantially immediately upon administration. In one embodiment, immediate-release results in dissolution of an agent within 1-20 minutes after entering the stomach. Dissolution can be of all or less than the entire amount of the active agent. For example, dissolution of 100% of an agent (antihistamine or antiemetic) can occur in the prescribed time. Alternatively, dissolution of less than all of the agent can occur in about 1 minute to about 20 minutes (e.g., dissolution of about 70%, about 75%, about 80%, about 85%, about 90%, about 91%, about 92%, about 93%, about 94%, about 95%, about 96%, about 97%, about 98%, about 99%, about 99.5% or 99.9% of an agent).

In one embodiment, the compositions comprise an antiemetic in an amount capable of achieving a serum level Cmax of from about 0.2 ng/mL to about 1 ng/mL at a Tmax of from about 1 to about 6 hours following oral administration. In one embodiment the antiemetic is promethazine or a pharmaceutically acceptable salt thereof. In another embodiment, the pharmaceutically acceptable salt is promethazine HCl. In a further embodiment, the composition is a bilayer tablet that has an immediate release layer and a controlled-release layer. In yet a further embodiment, the controlled release layer comprises an opioid analgesic agent or a non-opioid analgesic agent. In a further embodiment the immediate-release layer comprises promethazine or a pharmaceutically acceptable salt thereof.

In another embodiment, the compositions comprise promethazine or a pharmaceutically acceptable salt thereof in an amount capable of achieving a serum level Cmax of about 0.46 ng/mL at a Tmax of about 2 to about 3 hours following oral administration. In one embodiment, the promethazine or a pharmaceutically acceptable salt is at a dose by weight in the composition of about 10 mg to about 15 mg. In another embodiment, the promethazine or pharmaceutically acceptable salt is at a dose (by weight in the composition) of about 12.5 mg. In a further embodiment, the composition is in the form of a bilayer tablet that has an immediate release layer and a controlled-release layer. In yet another embodiment, the promethazine or a pharmaceutically acceptable salt is the only pharmaceutically active agent in the immediate release layer of a bilayer tablet of the invention. In one embodiment, the promethazine is promethazine HCl. In yet a further embodiment, the controlled release layer comprises an opioid analgesic agent or a non-opioid analgesic agent. In a further embodiment, the opioid analgesic is the only pharmaceutically active agent in the controlled-release layer of a bilayer tablet, non-opioid analgesic is the only pharmaceutically active agent in the controlled-release layer of a bilayer tablet or both the opioid analgesic and non-opioid analgesic are the only pharmaceutically active agents of the composition.

In another embodiment, immediate-release occurs when there is dissolution of an agent within 1-20 minutes after oral administration. In another embodiment, immediate-release results in substantially complete dissolution within about 1 hour following oral administration. In one embodiment, a composition of the invention is capable of providing about 80% dissolution of an antiemetic in about 5 minutes (e.g., FIG. 5).

In various embodiments, immediate-release occurs when there is dissolution of an agent within 1-20 minutes after administration. Dissolution can occur in a subject's stomach and/or intestine. In another embodiment, immediate-release results in complete or less than complete dissolution within about 1 hour following administration to a subject. In another embodiment, immediate-release results in complete or less than complete dissolution within about 1 hour following rectal administration. When used in association with the dissolution profiles discussed herein, the term "immediate-release" refers to wherein all or less than the entire amount of a dosage form is dissolved.

In some embodiments, immediate-release is through inhalation, such that dissolution occurs in a subject's lungs, as further described herein. Dissolution of less than all of an active includes but is not limited to dissolution of about 50%, 60%, 70%, 80%, 85%, 90%, 95%, 97%, 98%, 99%, 99.1%, 99.2%, 99.35, 99.4%, 99.5%, 99.6%, 99.7%, 99.8% or 99.99% of the active agent. Methods for measuring dissolution profiles are known (e.g., Example 15, infra).

In terms of a composition of the invention, "controlled-release" refers to the release of at least one pharmaceutically active agent from a dosage form at a particular desired point in time after the dosage form has is administered to a subject. Generally, controlled-release includes sustained but otherwise complete release. A sudden and total release in the stomach at a desired and appointed time or a release in the intestines such as through the use of an enteric coating, are both considered controlled-release. Controlled-release can occur at a predetermined time or in a predetermined place within the digestive tract. It is not meant to be a passive, uncontrolled process as in swallowing a normal tablet. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,556; 5,871,776; 5,902,632; and 5,837,284 each of which is incorporated herein by reference in its entirety.

A control release dosage form begins its release and continues that release over an extended period of time. Release can occur beginning almost immediately or can be sustained. Release can be constant, can increase or decrease over time, can be pulsed, can be continuous or intermittent, and the like. Generally, however, the release of at least one pharmaceutically active agent from a controlled-release dosage form will exceed the amount of time of release of the drug taken as a normal, passive release tablet. Thus, for example, while all of at least one pharmaceutically active agent of an uncoated aspirin tablet should be released within, for example, four hours, a controlled-release dosage form could release a smaller amount of aspirin over a period of six hours, 12 hours, or even longer. Controlled-release in accordance with the compositions and methods described herein generally means that the release occurs for a period of six hours or more, such as 12 hours or more.

Extended-release, or sustained-release, refers to the release of an agent, from a composition or dosage form in which the agent is released according to a desired profile over an extended period of time. In one embodiment, controlled-release results in dissolution of an agent within 20-720 minutes after entering the stomach. In another embodiment, controlled-release occurs when there is dissolution of an agent within 20-720 minutes after being swallowed. In another embodiment, controlled-release occurs when there is dissolution of an agent within 20-720 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. For example, controlled-release compositions allow delivery of an agent to a subject over an extended period of time according to a predetermined profile. Such release rates can provide therapeutically effective levels of agent for an extended period of time and thereby provide a longer period of pharmacologic or diagnostic response as compared with conventional rapid release dosage forms. Such longer periods of response provide for many inherent benefits that are not achieved with immediate-release dosages. In using analgesics for treatments of chronic pain, controlled-release formulations can be used instead of conventional short-acting formulations. When used in connection with the dissolution profiles discussed herein, the term "controlled-release" refers to wherein all or less than all of the total amount of a dosage form, made according to methods and compositions described herein, delivers an active agent over a period of time greater than 1 hour.

In one embodiment, controlled-release refers to delayed release of an agent, from a composition or dosage form in which the agent is released according to a desired profile in which the release occurs after a period of time.

When present in a controlled-release oral dosage form, the compositions described herein can be administered at a substantially lower daily dosage level than immediate-release forms. At comparable daily dosage levels, the controlled-release oral solid dosage forms can provide greater in pain relief than immediate-release forms.

Bilayer Tablet

In one embodiment of the invention, the invention relates to multi-layer tablets, such as bi-layer tablets. In one embodiment, the bi-layer tablet comprises: (a) an immediate-release layer; and (b) a controlled-release layer. In various embodiments, the immediate-release layer or the controlled-released layer comprises one or more pharmaceutically active agents. In one embodiment, a bilayer tablet of the invention has a hardness of about 7, 7.5, 8, 8.5, 9, 9.5, 10, 10.5, 11, 11.5, 12, 12.5, 13, 13.5, 14, 14.5 or 15 kiloponds (kp). In one embodiment, the bilayer tablet has a hardness of about 9.5 kp. In a further embodiment, a bilayer tablet of the invention has a thickness of about 5, 5.5, 6, 6.5, 7, 7.5, 8, 8.5, 9, 9.5 or 10 mm. It will be understood that as to the kilopond and thickness measurements, increments of 0.1 decimal points are within the scope of the invention. A nonlimiting example of a bilayer tablet of the invention is depicted in FIG. 2. In various embodiments, the tablet can be rectangular, tubular, oblong (e.g., FIG. 2), circular, oval or in a capsule form.

In various embodiments, a bilayer tablet of the invention provides an effective amount of one or more pharmaceutically active agents for about 4 to about 6 hours following oral administration, about 12 hours following oral administration, about 24 hours following oral administration, or 48 hours following administration. In various embodiments, the one or more pharmaceutically active agents provided in 4-6 hour, 12 hour, 24 hour or 48 hour dosing intervals. Therefore, a bilayer tablet of the invention is capable of providing any of the one or more pharmaceutically active agents disclosed herein in the foregoing dosing intervals.

In one embodiment, a composition comprises promethazine or a pharmaceutically acceptable salt thereof and about 70 to about 80% of the promethazine or pharmaceutically acceptable salt thereof dissolves in the stomach of a subject after about 5 to about 10 minutes following oral administration. In one embodiment, the promethazine is promethazine HCl.

In one embodiment, a composition comprises hydrocodone or a pharmaceutically acceptable salt thereof and about 30 to about 60% of the hydrocodone or pharmaceutically acceptable salt thereof dissolves in the stomach of a subject after about 5 to about 10 minutes following oral administration.

In one embodiment, the hydrocodone salt is hydrocodone bitartrate. In one embodiment, a composition comprises acetaminophen or a pharmaceutically acceptable salt thereof and 50% to about 70% of the acetaminophen or pharmaceutically acceptable salt thereof dissolves in the stomach of a subject after about 5 to about 10 minutes following oral administration.

In one embodiment, the composition comprises promethazine or a pharmaceutically acceptable salt thereof, hydrocodone or a pharmaceutically acceptable salt thereof and acetaminophen or a pharmaceutically acceptable salt thereof, and at least 90% of the pharmaceutically active agents in the composition dissolve in the stomach of a subject after about 45 minutes following oral administration. In one embodiment, the composition is a bilayer tablet comprising an immediate-release layer and a controlled-release layer.

In one embodiment, the immediate release layer comprises promethazine or a pharmaceutically acceptable salt as the only pharmaceutically active agent. In another embodiment, the controlled-release layer comprises hydrocodone or a pharmaceutically acceptable salt and acetaminophen or a pharmaceutically acceptable salt as the only pharmaceutical ingredients.

In yet another embodiment, the controlled release layer comprises an opioid analgesic or a non-opioid analgesic as the only pharmaceutically active agent. In another embodiment, the controlled release layer comprises an opioid analgesic and a non-opioid analgesic as the only pharmaceutically active agents. In another embodiment the immediate release layer comprises an antiemetic or a stimulant as the only pharmaceutically active agent. In another embodiment the immediate release layer comprises an antiemetic and a stimulant as the only pharmaceutically active agents.

Immediate-Release Layer

In one embodiment, the immediate-release layer is capable of releasing about 70 to about 80% of the one or more pharmaceutically active agent contained therein in the stomach of a subject in about 5 to about 10 minutes following oral administration. In one embodiment, the immediate-release layer is capable of releasing about 90 to about 100% of one or more pharmaceutically active agent contained therein in the stomach of a subject in about 40 minutes.

In one embodiment, the one or more pharmaceutically active agent in the immediate-release layer is an antiemetic. In one embodiment, the antiemetic is promethazine or a pharmaceutically acceptable salt thereof. In another embodiment, the antiemetic is promethazine HCl.

In one embodiment, an immediate-release layer comprises two or more agents, including an anti-emetic and a stimulant.

In some embodiments, the immediate-release layer comprises one or more excipients, including but not limited to silicified microcrystalline cellulose (e.g., HD90), croscarmellose sodium (AC-Di-Sol), magnesium stearate. In one embodiment, the total layer weight of the immediate-release layer is from about 100 to about 300 mg, such as about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg.

In one embodiment, the immediate-release layer comprises from about 75 mg to about 150 mg of silicified microcrystalline cellulose, from about 10 mg to about 20 mg croscarmellose sodium, from about 0.5 mg to 2 mg magnesium stearate. In yet a further embodiment, the immediate-release layer comprises from about 10 to about 15 mg promethazine, or a pharmaceutically acceptable salt thereof. In another embodiment, the immediate-release layer comprises about 12.5 mg promethazine or a pharmaceutically acceptable salt thereof. In another embodiment, the pharmaceutically acceptable salt is promethazine HCl.

In one embodiment, the immediate-release layer comprise about 12.5 mg promethazine HCl, about 121.5 mg silicified microcrystalline cellulose, about 15 mg croscarmellose sodium, and about 1 mg magnesium stearate.

In one embodiment, a composition comprising an effective amount of each of hydrocodone bitartrate, acetaminophen and promethazine HCl is capable of dissolving in the stomach of a subject so that an effective plasma concentration of each of pharmaceutically active ingredient is present in a subject in from about 5 minutes to about 30 minutes.

Controlled-release Layer

In one embodiment, the controlled-release layer is capable of releasing about 30 to about 40% of the one or more pharmaceutically active agent contained therein in the stomach of a subject in about 5 to about 10 minutes following oral administration. In another embodiment, the controlled-release layer is capable of releasing about 90% of the one or more pharmaceutically active agents are released in about 40 minutes after oral administration.

In some embodiment, the controlled-release layer comprises one or more excipients, including but not limited to silicified microcrystalline cellulose (e.g., HD90), croscarmellose sodium (AC-Di-Sol), magnesium stearate. In one embodiment, the total layer weight of the controlled-release layer is from about 100 to about 300 mg, such as about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg.

In one embodiment, a controlled-release layer comprises from about 75 mg to about 250 mg of silicified microcrystalline cellulose, from about 10 mg to about 40 mg hydroxyl methyl propyl cellulose, from about 0.5 mg to 5 mg magnesium stearate, and from about 0.5 mg to about 5 mg stearic acid.

In one embodiment, the controlled-release layer comprises about 152 mg silicified microcrystalline cellulose, about 20 mg hydroxyl methyl propyl cellulose, about 2.75 mg magnesium stearate, about 2.75 stearic acid, about 7.5 mg hydrocodone, or a pharmaceutically acceptable salt thereof and about 325 mg acetaminophen or a pharmaceutically acceptable salt thereof. In yet a further embodiment, the controlled-release layer comprises from about 5 mg to about 12.5 mg hydrocodone or a pharmaceutically acceptable salt thereof. In one embodiment, the controlled-release layer comprises about 7.5 mg hydrocodone or a pharmaceutically acceptable salt thereof. In another embodiment, the opioid analgesic is oxycodone or a pharmaceutically acceptable salt thereof. In one embodiment, the pharmaceutically acceptable salt is oxycodone HCl. In another embodiment, the pharmaceutically acceptable salt for hydrocodone is hydrocodone bitartrate.

In yet a further embodiment, the controlled-release layer further comprises from about 290 mg to about 360 mg acetaminophen or a pharmaceutically acceptable salt thereof. In one embodiment the controlled-release layer comprises about 325 mg acetaminophen or a pharmaceutically acceptable salt thereof.

In one embodiment, the immediate-release layer comprises promethazine HCl and the controlled-release layer comprises hydrocodone bitartrate. In another embodiment, the controlled-release layer further comprises a non-opioid analgesic (e.g., acetaminophen).

In one embodiment, the one or more pharmaceutically active agents of the controlled-release layer is an opioid analgesic. In one embodiment, the opioid analgesic is hydrocodone or oxycodone; or a pharmaceutically acceptable salt thereof. In one embodiment, the immediate-release layer is about 150 mg in total layer weight and the controlled-release layer is about 550 mg total weight.

Furthermore, in one embodiment, the controlled-release layer comprises about 325 mg acetaminophen, about 7.5 mg hydrocodone bitartrate, about 152 mg silicified microcrystalline cellulose, about 20 mg hydroxyl methyl propyl cellulose (HPMC), about 2.75 mg magnesium stearate, and about 2.75 mg stearic acid; and the immediate-release layer comprises about 12.5 mg promethazine HCl, about 121 mg silicified microcrystalline cellulose, about 15 mg croscarmellose sodium, and about 1 mg magnesium stearate.

In various embodiments, a bilayer tablet of the invention can comprise the combinations of pharmaceutically active agents in Table 1 or Table 2, wherein the controlled-release layer comprises one or more opioid analgesic agents, triptan agents, non-analgesic agents, barbiturates or stimulants, and the immediate-release layer comprises one or more stimulants.

In one embodiment, a stimulant is present in the immediate-release layer, controlled-release layer or both layers; the immediate-release layer comprises one or more anti-emetic or antihistamines; and the controlled-release layer comprises one or more non-opioid analgesics. In addition, either layer of the bilayered tablet can comprise one or more anti-abuse agents disclosed herein.

In one embodiment, a bilayer tablet of the invention comprises a controlled-release layer comprising one or more analgesic agents as the only pharmaceutically active agents in the controlled-release layer. In another embodiment, a bilayer tablet of the invention comprises an immediate-release layer comprising an antiemetic agent as the only pharmaceutically active agent in the immediate-release layer.

In another embodiment the controlled release layer further comprises one or more of: silicified microcrystalline cellulose, hydroxy methyl propyl cellulose, magnesium stearate, and stearic acid. In another embodiment the immediate-release layer further comprises one or more of: silicified microcrystalline cellulose, croscarmellose sodium and magnesium stearate. In another embodiment the tablet has a hardness of about 9.5 kilopond and thickness from about 6.9 to about 7.0 mm. In another embodiment the hydrocodone salt is hydrocodone bitartrate. In another embodiment the promethazine salt is promethazine HCL. In another embodiment the controlled release layer is an inner layer and wherein the immediate-release layer is an outer layer.

In one embodiment the opioid analgesic is oxycodone or pharmaceutically acceptable salt thereof; and the one or more antiemetic is promethazine or a pharmaceutically acceptable salt thereof. In another embodiment the effective amount is an amount effective for treating or preventing pain for a period of about 12 hours immediately following administration to a subject. In another embodiment the bi-layer tablet comprises an immediate release layer and a controlled release layer. In another embodiment the immediate release layer comprises the promethazine or pharmaceutically acceptable salt thereof, and wherein the controlled release layer comprises the oxycodone, or a pharmaceutically acceptable salt thereof. In another embodiment about 70% of the promethazine or pharmaceutically acceptable salt thereof is capable of dissolving in a liquid solution in about 5 minutes after contact with the solution, and wherein about 30% of the oxycodone or pharmaceutically acceptable salt is capable of dissolving in a liquid solution in about 10 minutes after contact with the solution. In another embodiment the controlled release layer further comprises an antiemetic agent.

In one embodiment the effective amount of the hydrocodone or pharmaceutically acceptable salt thereof is an amount effective for treating or preventing pain for a period of about 12 hours immediately following administration to a subject. In another embodiment the controlled release layer comprises about 7.5 mg of hydrocodone or a pharmaceutically acceptable salt thereof, about 325 mg of acetaminophen or a pharmaceutically acceptable salt thereof, about 152 mg of silicified microcrystalline cellulose, about 20 mg of hydroxy methyl propyl cellulose, about 2.7 mg of magnesium stearate, and about 2.7 mg of stearic acid; and the immediate release layer comprises about 12.5 mg of promethazine or a pharmaceutically acceptable salt thereof, about 121.5 mg of silicified microcrystalline cellulose, about 15 mg of croscarmellose sodium and about 1 mg of magnesium stearate.

In another embodiment the composition further comprises an effective amount of naltrexone or a pharmaceutically acceptable salt thereof. In another embodiment the composition is in the form of a bi-layer tablet. In another embodiment the effective amount of the morphine or pharmaceutically acceptable salt thereof is an amount effective for treating or preventing pain for a period of about 12 hours immediately following administration to a subject.

In one embodiment the controlled release layer comprises about 7.5 mg of hydrocodone or a pharmaceutically acceptable salt thereof, and about 325 mg of acetaminophen or a pharmaceutically acceptable salt thereof; and further wherein the immediate-release layer comprises about 12 mg of promethazine or a pharmaceutically acceptable salt thereof.

In one embodiment the effective amount is an amount effective for treating or preventing pain for a period of about 12 hours immediately following administration to a subject.

In one embodiment the effective amount of the oxycodone or pharmaceutically acceptable salt thereof is an amount effective for treating or preventing pain for a period of about 12 hours immediately following administration to a subject.

Combination Formulations

Various embodiments of the invention are directed to compositions comprising an effective amount of each of an analgesic and an active agent that is useful for reducing an adverse effect associated with such one or more opioid analgesics, or one or more non-opioid analgesic. Various embodiments for compositions of the invention are provided in Table 1 or Table 2.

Such additional active agents include antiemetics and antihistamines. In some embodiments, the analgesics are opioid or non-opioid analgesics (e.g., hydrocodone or oxycodone, or a pharmaceutically acceptable salt thereof and acetaminophen or a pharmaceutically acceptable salt thereof). In a further embodiment, the active agent which reduces adverse effects of such analgesics is promethazine or a pharmaceutically acceptable salt thereof.

In one embodiment, a composition of the invention allows for higher dosages for said analgesics in the composition, by reducing adverse effects associated with an opioid or non-opioid analgesic. For example, in a subject who could not otherwise tolerate a particular dosage of an opioid analgesic, it is believed that a composition of the invention comprising an effective amount of each of an opioid analgesic, a non-opioid analgesic and promethazine or a pharmaceutically acceptable salt thereof, will reduce an adverse effects (e.g. nausea or vomiting) associated with an opioid analgesic, thus allowing for increased dosages to be administered. Furthermore, administration can be through a single composition.

In various embodiments, the analgesic agent of the composition is an opioid analgesic agent such as hydrocodone, oxycodone, acetyldihydrocodeinone, diamorphine, codeine, pethidine, alfentanil, buprenorphine, butorphanol, codeine, dezocine, fentanyl, hydromorphone, levomethadyl acetate, levorphanol, meperidine, methadone, morphine sulfate, nalbuphine, oxymorphone, pentazocine, propoxyphene, remifentanil, sufentanil, tramadol, or a pharmaceutically acceptable salt thereof. In one embodiment, the opioid analgesic agent is hydrocodone, oxycodone, propoxyphene, or fentanyl or a pharmaceutically acceptable salt thereof.

In another embodiment, a dosage form comprises an opioid analgesic and one or more antiemetic. In another embodiment, a dosage form comprises hydrocodone or oxycodone or a pharmaceutically acceptable salt thereof and one or more antiemetic, which are disclosed herein.

In some embodiments, a composition of the invention comprises an opioid antagonist agent or abuse deterrent agent such as nalmefene, naloxone, niacin, naltrexone or a pharmaceutically acceptable salt thereof. The composition can further comprise an antitussive such as codeine or dextromethorphan, dextrorphan, or a pharmaceutically acceptable salt thereof.

As stated above, a pharmaceutically active agent can be in the form of a pharmaceutically acceptable salt. Each agent disclosed herein can be used in a composition of the invention as its free base or its pharmaceutically acceptable salt, prodrug, analog and complex. In various embodiments of the invention, with respect to a pharmaceutically active agent in a composition, a pharmaceutically acceptable salt includes, but is not limited to, metal salts, such as sodium salts, potassium salts, and lithium salts; alkaline earth metals, such as calcium salts, magnesium salts, and the like; organic amine salts, such as triethylamine salts, pyridine salts, picoline salts, ethanolamine salts, triethanolamine salts, dicyclohexylamine salts, N,N'-dibenzylethylenediamine salts, and the like; inorganic acid salts such as hydrochloride salts, hydrobromide salts, sulfate salts, phosphate salts, and the like; organic acid salts such as formate salts, acetate salts, trifluoroacetate salts, maleate salts, tartrate salts, and the like; sulfonate salts such as methanesulfonate salts, benzenesulfonate salts, p-toluenesulfonate salts, and the like; and amino acid salts, such as arginate salts, asparginate salts, glutamate salts, and the like.

In addition, pharmaceutically acceptable salts include bitartrate, bitartrate hydrate, hydrochloride, p-toluenesulfonate, phosphate, sulfate, trifluoroacetate, bitartrate hemipentahydrate, pentafluoropropionate, hydrobromide, mucate, oleate, phosphate dibasic, phosphate monobasic, acetate trihydrate, bis(heptafuorobutyrate), bis(pentafluoropropionate), bis(pyridine carboxylate), bis(trifluoroacetate), chlorhydrate, and sulfate pentahydrate. In one embodiment the agent is hydrocodone, a pharmaceutically acceptable salt or its thiosemicarbazone, p-nitrophenylhydrazone, o-methyloxime, semicarbazone, or bis (methylcarbamate). In another embodiment the agent is oxycodone, a pharmaceutically acceptable salt or its thiosemicarbazone, p-nitrophenylhydrazone, o-methyloxime, semicarbazone, or bis (methylcarbamate). In a further embodiment the agent is acetaminophen, a pharmaceutically acceptable salt or its thiosemicarbazone, p-nitrophenylhydrazone, o-methyloxime, semicarbazone, or bis (methylcarbamate). In another embodiment an agent is promethazine, a pharmaceutically acceptable salt or its thiosemicarbazone, p-nitrophenylhydrazone, o-methyloxime, semicarbazone, or bis (methylcarbamate). Other representative pharmaceutically acceptable salts include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, butyrate, calcium edetate, camphorsulfonate, camsylate, carbonate, citrate, clavulariate, dihydrochloride, edetate, edisylate, estolate, esylate, fiunarate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A hydrate is another example of a pharmaceutically acceptable salt.

In some embodiments, a composition of the invention comprises an effective amount of each of an opioid analgesic agent and a non-opioid analgesic agent, where the opioid analgesic agent/non-opioid analgesic agent is codeine/acetaminophen, codeine/aspirin, codeine/naproxen, codeine/ibuprofen, hydrocodone/acetaminophen, hydrocodone/ibuprofen, hydrocodone/naproxen, hydrocodone/aspirin, oxycodone/acetaminophen, oxycodone/aspirin, oxycodone/naproxen, oxycodone/ibuprofen, propoxyphene/aspirin, propoxyphene/ibuprofen, propoxyphene/acetaminophen, or propoxyphene/naproxen, wherein the opioid analgesic agent or non-opioid analgesic agent is optionally in the form of a or a pharmaceutically acceptable salt thereof. In one embodiment, the hydrocodone salt is hydrocodone bitartrate, the oxycodone salt is oxycodone HCl, and the naproxen salt is naproxen Na or Mg.

In some embodiments the compositions disclosed herein may further comprise one or more of an opioid antagonist agent, abuse deterrent agent, a barbiturate agent, a stimulant agent, or an antiemetic agent.

Therefore, in some embodiments, a composition comprises an effective amount of an opioid analgesic agent (such as hydrocodone or oxycodone or a pharmaceutically acceptable salt thereof), a non-opioid analgesic agent (such as acetaminophen or naproxen or a pharmaceutically acceptable salt thereof) and an active agent useful for reducing or eliminating adverse effects, such as an antihistamine (e.g., promethazine or a pharmaceutically acceptable salt thereof) or an antiemetic, as described herein. In one embodiment the composition is in the form of a bi-layer tablet that comprises an immediate-release layer and a controlled-release layer. In a further embodiment the immediate-release layer comprises one or more of an opioid agent, a non-opioid analgesic agent and an active agent useful for reducing or eliminating adverse effects. In a further embodiment a controlled-release layer comprises an effective amount of one or more of an opioid agent, a non-opioid analgesic agent and an active agent useful for reducing or eliminating adverse effects associated with administration of an opioid analgesic agent or non-opioid analgesic agent. In some embodiments a composition further comprises an effective amount of an opioid antagonist agent or abuse deterrent agent. In a specific embodiment the composition comprises hydrocodone or oxycodone, or a pharmaceutically acceptable salt thereof, acetaminophen or a pharmaceutically acceptable salt thereof, or naproxen or a pharmaceutically acceptable salt thereof, and promethazine or a pharmaceutically acceptable salt thereof.

Examples of non-opioid analgesic agents useful in the compositions of the invention include but are not limited to acetaminophen; a non-steroidal anti-inflammatory drug (NSAID) such as a salicylate (including, for example, amoxiprin, benorilate, choline magnesium salicylate, diflunisal, faislamine, methyl salicylate, magnesium salicylate), an arylalkanoic acid (including, for example, diclofenac, aceclofenac, acemetacin, bromfenac, etodolac, indometacin, nabumetone, sulindac, tolmetin), a profen (including, for example, ibuprofen, carprofen, fenbuprofen, flubiprofen, ketaprofen, ketorolac, loxoprofen, naproxen, suprofen), a fenamic acid (including, for example mefenamic acid, meclofenamic acid), an oxicam (including, for example, piroxicam, lomoxicam, meloxicam, tenoxicam), a pyrazolidine derivative (including, for example, phenylbutazone, azapropazone, metamizole, oxyphenbutazone, sulfinprazone) or a pharmaceutically acceptable salt thereof; a Cox-2 inhibitor (such as valdecoxib, celecoxib, rofecoxib or a pharmaceutically acceptable salt thereof), a local analgesic (such as lidocaine, mexiletine or a pharmaceutically acceptable salt thereof); an anti-depressant (such as amitriptyline, carbamazepine, gabapentin, pregabalin, amoxapine, clomipramine, desipramine, dosulepin, doxepin, imipramine, iprindole, lofepramine, nortriptyline, opipramol, protryptyline, trimipramine or a pharmaceutically acceptable salt thereof) an atypical analgesic (such as orphenadrine, cyclobenzaprine, scopolamine, atropine, gabapentin or a pharmaceutically acceptable salt thereof), a psychotropic agent (such as tetrahydrocannabinol or a pharmaceutically acceptable salt thereof), an NMDA receptor antagonist (such as ketamine, amantadine, dextromethorphan, dextrorphan, ibogaine, phencyclidine, riluzole, tiletamine, memantine, dizocilpine, patiganel, remacimide, or a pharmaceutically acceptable salt thereof), an $\alpha_2$-adrenoreceptor agonists (such as clonidine or a pharmaceutically acceptable salt thereof) and a synthetic drug having narcotic properties such as tramadol. In one embodiment the non-opioid analgesic agent is acetaminophen, naproxen or a pharmaceutically acceptable salt thereof.

The agent useful for preventing or alleviating an adverse effect associated with administration of an opioid analgesic or a non-opioid analgesic, a triptan, barbiturate or morphine narcotic, includes, for example, an antihistamine including a histamine agonist and an antagonist which is classified according to receptor subtype.

Such antihistamines include H1 agonists and H1 antagonists. H1 agonists or partial agonists include 2-(m-fluorophenyl)-histamine and H1 antagonists include chlorpheniramine, scopolamine, mepyramine, terfenadine, astemizole, and triprolidine. Further antagonists (which may be further classified by their chemical structures) include the ethanolamines carbinoxamine, dimenhydrinate, diphenhydramine, and doxylamine; the ethylaminediamines pyrilamine and tripelennamine; the piperazine derivatives dydroxyzine, cyclizine, fexofenadine and meclizine; the alkylamines brompheniramine and chlorpheniramine; and miscellaneous antagonists cyproheptadine, loratadine, cetrizine. H2 agonists include dimaprit, impromidine, and amthamine; and H2 antagonists (useful in the treatment of gastric acid secretion) include cimetidine, ranitidine, nizatidine, and famotidine; H3 agonists include R-alpha-methylhistamine, imetit, and immepip and H3 antagonists include thioperamide, iodophenpropit, and clobenpropit; and H4 agonists include clobenpropit, imetit, and clozapine and H4 antagonists include thioperamide.

The agent useful for preventing or suppressing a adverse effect can also include an H1 blocker, such as azelastine, brompheniramine, buclizine, carbinoxamine, cetrizine, chlorpheniramine, clemastine, cyclizine, cyproheptadine, desloratidine, dimenhydrinate, diphenhydramine, emedastine, fexofenadine, hydroxyzine, ketotifen, levocabastine, loratadine, meclizine, olopatadine, phenindamine, and promoathazine.

In various embodiments compositions comprise two, three, four, five, six or more active agents. In one embodiment at least one of the active agents is an antiemetic or antihistamine. In other embodiment, a composition does not comprise promethazine or a pharmaceutically acceptable salt. As indicated herein, a composition can comprise pharmaceutically active agents in the combinations provided in Table 1 or Table 2.

As indicated above, compositions can comprise an antiemetic agent including, for example, aprepitant, dronabinol, perphenazine, palonosetron, trimethyobenzamide, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, *cannabis*, midazolam, lorazepam, hyoscine, dexamethasone, emetrol, propofol and a pharmaceutically acceptable salt or mixtures thereof.

In another embodiment the composition can comprise an antitussive agent including, for example, dextromethorphan, dextrorphan, noscapine, ethyl morphine, codeine, camphor, menthol, theobromine, guaifenesin, or the like.

In various embodiments of the invention, a composition comprises at least two analgesics; and one or more additional pharmaceutically active agents disclosed in Table 1 or Table 2. In one embodiment, the composition further comprises one antihistamine or antiemetic.

In some embodiments a composition comprises a stimulant agent. Stimulant agents useful in the methods and compositions of the invention include, but are not limited to, aminophylline, caffeine, dyphlline, oxitriphylline, theophhylline, amphetamine, benzphetamine, dextroamphetamine, diethylpropion, mazindol, methamphetamine, methylphenidate, dexmethylphenidate, pemoline, sibutramine, modafinil, atomoxetine, phendimetrizine, phenteramine, adrafinil, phenylpropanolamine, psuedoephedrine, Synephrine, amphetaminil, furfenorex, or a combination thereof. In some embodiments, compositions comprise a stimulant agent that provides an anti-sedative effect.

A stimulant agent can be an amphetamine, examples of which include but are not limited to methamphetamine, levoamphetamine, dextroamphetamine, 3,5-methyloxy amphetamine, 2,5-dimethoxy-4-methylthioamphetamine, 2,5-dimethoxy-4-ethylthioamphetamine, 2,5-dimethoxy-4-(i)-propylthioamphetamine, 2,5-dimethoxy-4-phenylthioamphetamine, 2,5-dimethoxy-4-(n)-propylthioamphetamine, Brolamfetamine, 2,5-dimethoxy-4-iodoamphetamine, 2,5-Dimethoxy-4-methylamphetamine, 2,5-Dimethoxy-4-butyl-amphetamine, 3,4-Dimethyl-2,5-dimethoxyamphetamine, 2-Phenylethylamine, propylamphetamine, methylphenidate, lisdexamfetamine, ethylamphetamine, MDMA (3,4-methylenedioxy-N-methylamphetamine), MDEA (3,4-methylenedioxy-N-ethylamphetamine), PMA (p-methoxyamphetamine), DMA (2-(2,4-Dimethoxy-phenyl)-1-methyl-ethylamine), benzphetamine, 4-FMP (para-fluoroamphetamine), or 4-MTA (4-Methylthioamphetamine), or a pharmaceutically acceptable salt thereof.

In one embodiment, a composition is provided that comprises an effective amount of an opioid (such as hydrocodone, propoxyphene, fentanyl or oxycodone, or a pharmaceutically acceptable salt thereof) and a stimulant (such as modafinil or caffeine, or a pharmaceutically acceptable salt thereof). In some embodiments a composition further comprises an antiemetic. In one embodiment, the antiemetic is promethazine or a pharmaceutically acceptable salt thereof. In yet another embodiment, the composition further comprises a non-analgesic agent disclosed herein. In one embodiment, the non-opioid analgesic is acetaminophen or a pharmaceutically acceptable salt thereof, or naproxen or a pharmaceutically acceptable salt thereof.

In a further a composition is in the form of a bilayer tablet comprising an immediate-release layer and a controlled-release layer, wherein the immediate-release layer comprises and/or the chronic-release layer comprise a stimulant agent. In one embodiment, the controlled-release layer comprises an opioid agent. In yet a further embodiment, the controlled-release layer further comprises an effective amount of a second or same stimulant agent as compared to the immediate-release layer. In yet another embodiment, the immediate-release layer and/or the controlled-release layer further comprises an antiemetic agent. In a further embodiment the immediate-release layer comprises an effective amount of one or more of an opioid agent, a stimulant agent and an antiemetic agent. In another further embodiment a controlled-release layer comprises an effective amount of one or more of an opioid agent, a stimulant agent, and an antiemetic agent. In some embodiments the composition further comprises an effective amount of an opioid antagonist agent or abuse deterrent agent.

In a specific embodiment a composition is provided that comprises hydrocodone or oxycodone, or a pharmaceutically acceptable salt thereof, modafinil or caffeine or a pharmaceutically acceptable salt thereof and optionally promethazine or a pharmaceutically acceptable salt thereof.

In some embodiments compositions comprise a barbiturate active agent. Barbiturate agents useful in the methods and compositions include, but are not limited to, Allobarbital, Alphenal, Amobarbital, Aprobarbital, Barbexaclone, Barbital, Brallobarbital, Butabarbital, Butalbital, Butobarbital, Butallylonal, Crotylbarbital, Cyclobarbital, Cyclopal, Ethallobarbital, Febarbamate, Heptabarbital, Hexethal, Hexobarbital, Mephobarbital, Metharbital, Methohexital, Methylphenobarbital, Narcobarbital, Nealbarbital, Pentobarbital, Primidone, Probarbital, Propallylonal, Proxibarbal, Proxibarbital, Reposal, Secbutabarbital, Secobarbital, Sigmodal, Talbutal, Thialbarbital, Thiamylal, Thiobarbital, Thiobutabarbital, Thiopental, Valofane, Vinbarbital, Vinylbital, 1,3-dimethoxymethyl 5,5-diphenyl-barbituric acid (DMMDPB), 1-monomethoxymethyl 5,5-diphenylbarbituric acid (MMMDPB), a diphenyl-barbituric acid (DPB) and their precursors, derivatives and analogs or a combination thereof and a pharmaceutically acceptable salt thereof.

In another embodiment, a composition is provided that comprises an effective amount of an opioid agent (such as hydrocodone, propoxyphene, fentanyl or oxycodone, or a pharmaceutically acceptable salt thereof); a non-opioid agent (such as acetaminophen or naproxen, or a pharmaceutically acceptable salt thereof); a barbiturate agent (such as butalbital, or a pharmaceutically acceptable salt thereof) and optionally an antiemetic (such as promethazine, or a pharmaceutically acceptable salt thereof).

In a further embodiment a composition is in the form of a bilayer tablet, wherein the composition comprises an effective amount of each of an opioid agent, a non-opioid analgesic agent, a barbiturate agent and an antiemetic agent. In one embodiment the bi-layer tablet comprises an immediate-release layer and a controlled-release layer. In a further embodiment the immediate-release layer comprises an effective amount of one or more of an opioid agent, a non-opioid analgesic agent, a barbiturate agent and an antiemetic agent. In another further embodiment a controlled-release layer comprises an effective amount of one or more of an opioid agent, a barbiturate agent, a non-opioid analgesic agent, and an antiemetic agent. In some embodiments a composition further comprises an effective amount of an opioid antagonist agent or abuse deterrent agent. In a specific embodiment a composition comprises hydrocodone or oxycodone, or a pharmaceutically acceptable salt thereof acetaminophen, or a pharmaceutically acceptable salt thereof, butalbital or a pharmaceutically acceptable salt thereof and optionally promethazine or a pharmaceutically acceptable salt thereof.

In another embodiment an a composition comprises an effective amount of each of an opioid agent (such as hydrocodone, propoxyphene, fentanyl or oxycodone or a pharmaceutically acceptable salt thereof); a barbiturate agent (such as butalbital or a pharmaceutically acceptable salt thereof); a stimulant agent (such as modafinil or caffeine or a pharmaceutically acceptable salt thereof); and optionally a non-opioid agent (such as acetaminophen or naproxen or a pharmaceutically acceptable salt thereof). In some embodiments the composition further comprises an antiemetic (such as promethazine or a pharmaceutically acceptable salt thereof).

In one embodiment, such a composition is in the form of a bi-layer tablet, wherein the composition comprises an effective amount of an opioid agent, a non-opioid analgesic agent, a barbiturate agent, a stimulant agent and optionally an antiemetic agent. In one embodiment the bi-layer tablet comprises an immediate-release layer and a controlled-release layer. In a further embodiment the immediate-release layer comprises an effective amount of one or more of an opioid agent, a non-opioid analgesic agent, a barbiturate agent, a stimulant agent and an antiemetic agent. In another a further embodiment a controlled-release layer comprises an effective amount of one or more of an opioid agent, a non-opioid analgesic agent, a barbiturate agent, a stimulant agent and an antiemetic agent. In some embodiments a composition further comprises an effective amount of an opioid antagonist agent or abuse deterrent agent. In a specific embodiment a composition comprises hydrocodone, propoxyphene or oxycodone, or a pharmaceutically acceptable salt thereof; butalbital, naproxen, caffeine or a pharmaceutically acceptable salt thereof; and optionally promethazine or a pharmaceutically acceptable salt thereof.

In another embodiment a composition comprises an effective amount of an opioid agent (hydrocodone or oxycodone or a pharmaceutically acceptable salt thereof); and a barbiturate agent (such as butalbital or a pharmaceutically acceptable salt thereof). In some embodiments a composition further comprises an antiemetic (such as promethazine or a pharmaceutically acceptable salt thereof). In a further the composition is in the form of a bi-layer tablet, wherein the composition comprises an effective amount of each of an opioid analgesic agent, a barbiturate agent, and optionally an antiemetic agent. In one embodiment the bi-layer tablet comprises an immediate-release layer and a controlled-release layer. In a further embodiment the immediate-release layer comprises an effective amount of each of one or more of an opioid analgesic agent, a barbiturate agent, or an antiemetic agent. In another a further embodiment a controlled-release layer comprises an effective amount of each of one or more of an opioid analgesic agent, a barbiturate agent, or an antiemetic agent. In some the composition further comprises an effective amount of an opioid antagonist agent or abuse deterrent agent. In a specific embodiment a composition comprises butalbital, hydrocodone or oxycodone, or a pharmaceutically acceptable salt thereof and optionally promethazine or a pharmaceutically acceptable salt thereof.

In another embodiment a composition comprises an effective amount of a non-opioid agent (such as acetaminophen, naproxen or ibuprofen or a pharmaceutically acceptable salt thereof); a barbiturate agent (such as butalbital or a pharmaceutically acceptable salt thereof); and an antiemetic (such as promethazine or a pharmaceutically acceptable salt thereof). In one embodiment, the composition comprises about 50 mg butalbital or a pharmaceutically acceptable salt thereof, about 325 mg N-Acetyl-p-Aminophenol or a pharmaceutically acceptable salt thereof, and about 12.5 mg promethazine or a pharmaceutically acceptable salt thereof. In one embodiment, the promethazine salt is promethazine HCl.

In another embodiment a composition comprises an effective amount of each of a non-opioid agent (such as acetaminophen, naproxen or ibuprofen or a pharmaceutically acceptable salt thereof); a barbiturate agent (such as butalbital or a pharmaceutically acceptable salt thereof); and a stimulant agent (such as modafinil or caffeine or a pharmaceutically acceptable salt thereof). In some embodiments the composition further comprises an antiemetic (such as promethazine or a pharmaceutically acceptable salt thereof). In a further embodiment an effective amount of a composition is in the form of a bi-layer tablet, wherein the composition comprises an effective amount of each of a non-opioid analgesic agent, a barbiturate agent, a stimulant agent and optionally an antiemetic agent. In one embodiment the bi-layer tablet comprises an immediate-release layer and a controlled-release layer. In a further embodiment the immediate-release layer comprises an effective amount of one or more of a non-opioid analgesic agent, a barbiturate agent, a stimulant agent or an antiemetic agent. In another a further embodiment a controlled-release layer comprises one or more of a non-opioid analgesic agent, a barbiturate agent, stimulant agent or an antiemetic agent. In a specific embodiment a composition comprises butalbital, naproxen, caffeine, or a pharmaceutically acceptable salt thereof and optionally promethazine or a pharmaceutically acceptable salt thereof.

In another embodiment a composition comprises an effective amount of a barbiturate agent (such as butalbital or a pharmaceutically acceptable salt thereof) and a stimulant agent (such as modafinil or caffeine or a pharmaceutically acceptable salt thereof). In some embodiments the composition further comprises an antiemetic (such as promethazine or a pharmaceutically acceptable salt thereof). In another embodiment, a composition is in the form of a bi-layer tablet, wherein the composition comprises an effective amount of each of a barbiturate agent, a stimulant agent and optionally an antiemetic agent. In one embodiment the bi-layer tablet comprises an immediate-release layer and a controlled-release layer. In a further embodiment the immediate-release layer comprises an effective amount of each of one or more of a barbiturate agent, a stimulant agent or an antiemetic agent. In another a further embodiment a controlled-release layer comprises an effective amount of each of one or more of a barbiturate agent, stimulant agent or an antiemetic agent. In a specific embodiment a composition comprises butalbital or a pharmaceutically acceptable salt thereof, caffeine or a pharmaceutically acceptable salt thereof and optionally promethazine or a pharmaceutically acceptable salt thereof.

In another embodiment a composition comprises an effective amount of a non-opioid agent (such as ibuprofen or naproxen or a pharmaceutically acceptable salt thereof) and a stimulant agent (such as modafinil or caffeine or a pharmaceutically acceptable salt thereof). In some embodiments the composition further comprises an antiemetic (such as promethazine or a pharmaceutically acceptable salt thereof). In one embodiment, the composition is in the form of a bi-layer tablet, wherein the composition comprises an effective amount of each of a non-opioid agent, a stimulant agent and optionally an antiemetic agent. In one embodiment the bi-layer tablet comprises an immediate-release layer and a controlled-release layer. In a further embodiment the immediate-release layer comprises an effective amount of each of one or more of a non-opioid agent, a stimulant agent or an antiemetic agent. In another further embodiment the controlled-release layer comprises an effective amount of each of one or more of a non-opioid agent, stimulant agent or an antiemetic agent. In a specific embodiment a composition comprises naproxen or a pharmaceutically acceptable salt thereof and caffeine or a pharmaceutically acceptable salt thereof and optionally promethazine or a pharmaceutically acceptable salt thereof.

The present compositions can comprise one or more beta blockers, serotonin receptor agonists, vasoconstrictors, anti-platelet agents, anti-convulsants, triptans, ergots, or calcitonin-gene-related peptide (CGRP) receptor antagonists.

Non-limiting examples of beta blockers are acebutolol, arotinolol, atenolol, betaxolol, bisoprolol, butoxamine, carvedilol, carteolol, esmolol, carteolol, carvedilol, labetalol, levobunolol, mepindolol, metoprolol, nebivolol, nadolol, oxprenolol, penbutolol, propranolol, pindolol, sotalol, and timolol. In one embodiment, the beta blocker is propanolol.

Non-limiting examples of serotonin receptor agonists are buspirone, mescaline, psilocybin, cisapride, triptans, or lysergic acid diethylamide. Non-limiting examples of vasoconstrictors are isometheptene mucate, amphetamines, antihistamines, cocaine, caffeine, pseudoephedrine, ergine, methylphenidate, psilocybin, or stimulants such as amphakines (e.g., drugs effective to glutagatergic AMPA receptors and benzoylpiperidine derivatives). Non-limiting examples of amphetamines and antihistamines are disclosed herein above.

Non-limiting examples of anti-platelet agents are acetylsalycyclic acid, clopidogrel, ticlopidine, cilostazol, abciximab, eptifibatide, tirofiban defibrotide and dipyridamole.

Non-limiting examples of anti-convulsants are topiramate, divaprex, pehnobarbital, methlyphenobarbital, metharbital, barbexaclone, stiripentol, clobazam, clonazepam, clorazepate, diazepam, midazolam, lorazepam, nitrazepam, temazepam, nimetazepam, potassium bromide, felbamate, carbamazepine, oxcarbazepine, vigabatrin, progabide, tiagabine, gabapentin, prgabalin, ethotoin, phenytoin, mephenytoin, fosphenytoin, paramethadione, trimethadione, ethadione, beclaminde, primidone, brivaracetam, levetiracetam, seletracetam, ethsuximide, phesuximide, mesuximide, acetazolamide, sulthiame, methazolamide, zonisamide, lamotrigine, pheneturide, phenacemide, valpromide, valnoctamide and pharmaceutically acceptable salt thereof.

Non-limiting examples of calcitonin-gene-related peptide (CGRP) receptor antagonists are MK-0974, CGRP8-37, BIBN 4096 BS, quinine, nitrobenzamide, 4-oxobutanamides, cyclopropane derivatives, and benzimidazolinyl piperidines.

Non-limiting examples of triptans are naratriptan, almotriptan, sumatriptan, zolmitriptan, eletriptan, frovatriptan, or rizatriptan, or a pharmaceutically acceptable salt thereof. In some embodiments, a oral dosage form (e.g., bilayer tablet) is provided comprising one or more triptan and one or more antiemetic. In one embodiment, the triptan is sumatriptan or a pharmaceutically acceptable salt thereof, and the antiemetic is promethazine or a pharmaceutically acceptable salt thereof. In a further embodiment, the composition is a bilayer tablet comprising a controlled-release layer and an immediate-release layer, wherein the controlled-release layer comprises an effective amount of the sumatriptan or a pharmaceutically acceptable salt thereof and the immediate release layer comprises an effective amount of the promethazine or a pharmaceutically acceptable salt thereof. In one embodiment, the sumatriptan salt is sumatriptan succinate.

Non-limiting examples of ergots are ergotamine, methysergide, zonisamide and pharmaceutically acceptable salt thereof. In one embodiment, the compositions comprises: sumatriptan or a pharmaceutically acceptable salt thereof in a dosage from about 25 mg to about 100 mg and promethazine or a pharmaceutically acceptable salt thereof in a dosage of from about 12.5 mg to about 50 mg.

In various embodiments, compositions of the invention are administered in a single dosage form which comprises active agents as disclosed in Table 1 or Table 2 and one or more beta blockers, serotonin receptor agonists, vasoconstrictors, anti-platelet agents, anti-convulsants, triptans, ergot alkaloids, and calcitonin-gene-related peptide (CGRP) receptor antagonists.

In some embodiments, a single dosage form is a multi-layered tablet which comprises one or more pharmaceutically active agents which includes one or more beta blockers, serotonin receptor agonists, vasoconstrictors, anti-platelet agents, anti-convulsants, triptans, ergot alkaloids, or calcitonin-gene-related peptide (CGRP) receptor antagonists. In one embodiment, a multilayer tablet comprises at least one immediate release layer and at least one controlled-released layer. Compositions of the invention can be administered using other dosage forms disclosed herein.

In yet other embodiments, compositions comprising one or more active agents disclosed herein (e.g., Table 1 or Table 2) of the invention are administered prior to, concurrent with, or after administration of one or more beta blockers, serotonin receptor agonists, vasoconstrictors, anti-platelet agents, anti-convulsants, triptans, ergot alkaloids, or calcitonin-gene-related peptide (CGRP) receptor antagonists. In some embodiments the present methods for treating or preventing pain further comprise administering an effective amount of one or more beta blockers, serotonin receptor agonists, vasoconstrictors, anti-platelet agents, anti-convulsants, triptans, ergots, or CGRP receptor antagonists.

Dosage

In various embodiments compositions of the invention comprise multiple active agents at the same or different dosages. In some embodiments, the analgesic components may vary in dosages as further described herein, and the antihistamine or antiemetic dosage can be adjusted according to the particular analgesics used.

For example, in various embodiments compositions are provided that comprise an opioid analgesic agent that is present at from about a dose of about 1.0 mg to about 100 mg, including but not limited to 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, or 100 mg. In one embodiment the opioid analgesic agent is hydrocodone or oxycodone or salt thereof. In another embodiment the opioid analgesic agent is present in a bi-layer tablet that comprises an immediate release and a controlled release layer.

In another embodiment a composition is provided that comprises a non-opioid analgesic that is present at a dose from about 200 mg to about 1000 mg, including but not limited to 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. In one embodiment the non-opioid analgesic agent is present in a bi-layer tablet that comprises an immediate release and a controlled release layer.

In another embodiment the compositions comprise an antiemetic or antihistamine agent (e.g., promethazine) present at a dose from about 0.5 mg to about 200 mg of promethazine or a pharmaceutically acceptable salt thereof, including but not limited to 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11.0 mg, 11.5 mg, 12.0 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg. In one embodiment the antiemetic or antihistamine agent is present in a bi-layer tablet that comprises an immediate release and a controlled release layer.

In one embodiment, the compositions of the invention comprise an opioid analgesic agent (such as hydrocodone), a pharmaceutically acceptable salt or its thiosemicarbazone, p-nitrophenylhydrazone, o-methyloxime, semicarbazone, or bis(methylcarbamate) (each of the foregoing being a hydrocodone agent or derivative); acetaminophen; and promethazine or salt thereof. Furthermore, the opioid analgesic agent is present in a range of from about 1.0 mg to about 100 mg, including but not limited to 1 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, or 100 mg.

Furthermore, in various embodiments, the compositions of the invention comprise acetaminophen or a pharmaceutically acceptable salt thereof is present in the composition at a range of from about 200 mg to about 1000 mg, including but not limited to 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. In addition, the promethazine or salt thereof is present in the composition at a dose between about 0.5 mg to about 200 mg, including but not limited to 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11.0 mg, 11.5 mg, 12.0 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg. In one embodiment hydrocodone or a salt thereof, acetaminophen or a salt thereof, and promethazine or a salt thereof are present in a bi-layer tablet that comprises an immediate release and a controlled release layer. In another embodiment the immediate release layer comprises promethazine or a salt thereof and the controlled release layer comprises hydrocodone or a salt thereof and acetaminophen or a salt thereof.

In various embodiments, the compositions of the invention comprise an opioid analgesic agent (such as hydrocodone or oxycodone or a pharmaceutically acceptable salt thereof), acetaminophen or a pharmaceutically acceptable salt thereof and promethazine or a pharmaceutically acceptable salt thereof, wherein the composition comprises the respective agents, opioid analgesic agent: acetaminophen or a salt thereof: promethazine or a pharmaceutically acceptable salt thereof in a ratio by weight of about (1 to 2):(40 to 45):(1 to 2), such as about 1:40:1, 1:40:1.1, 1:40:1.2, 1:40:1.3, 1:40:1.4, 1:40:1.5, 1:40:1.6, 1:40:1.7, 1:40:1.8, 1:40:1.9, 1:40:2, 1.1:40:1, 1.2:40:1, 1.3:40:1, 1.4:40:1, 1.5:40:1, 1.6:40:1, 1.7:40:1, 1.8:40:1, 1.9:40:1, 2:40:1, 1:41:1, 1:41:1.1, 1:41:1.2, 1:41:1.3, 1:41:1.4, 1:41:1.5, 1:41:1.6, 1:41:1.7, 1:41:1.8, 1:41:1.9, 1:41:2, 1.1:41:1, 1.2:41:1, 1.3:41:1, 1.4:41:1, 1.5:41:1, 1.6:41:1, 1.7:41:1, 1.8:41:1, 1.9:41:1, 2:41:1, 1:42:1, 1:42:1.1, 1:42:1.2, 1:42:1.3, 1:42:1.4, 1:42:1.5, 1:42:1.6, 1:42:1.7, 1:42:1.8, 1:42:1.9, 1:42:2, 1.1:42:1, 1.2:42:1, 1.3:42:1, 1.4:42:1, 1.5:42:1, 1.6:42:1, 1.7:42:1, 1.8:42:1, 1.9:42:1, 2:42:1, 1:43:1, 1:43:1.1, 1:43:1.2, 1:43:1.3, 1:43:1.4, 1:43:1.5, 1:43:1.6, 1:43:1.7, 1:43:1.8, 1:43:1.9, 1:43:2, 1.1:43:1, 1.2:43:1, 1.3:43:1, 1.4:43:1, 1.5:43:1, 1.6:43:1, 1.7:43:1, 1.8:43:1, 1.9:43:1, 2:43:1, 1:43.1:1, 1:43.1:1.1, 1:43.1:1.2, 1:43.1:1.3, 1:43.1:1.4, 1:43.1:1.5, 1:43.1:1.6, 1:43.1:1.7, 1:43.1:1.8, 1:43.1:1.9, 1:43.1:2, 1.1:43.1:1, 1.2:43.1:1, 1.3:43.1:1, 1.4:43.1:1, 1.5:43.1:1, 1.6:43.1:1, 1.7:43.1:1, 1.8:43.1:1, 1.9:43.1:1, 2:43.1:1, 1:43.2:1, 1:43.2:1.1, 1:43.2:1.2, 1:43.2:1.3, 1:43.2:1.4, 1:43.2:1.5, 1:43.2:1.6, 1:43.2:1.7, 1:43.2:1.8, 1:43.2:1.9, 1:43.2:2, 1.1:43.2:1, 1.2:43.2:1, 1.3:43.2:1, 1.4:43.2:1, 1.5:43.2:1, 1.6:43.2:1, 1.7:43.2:1, 1.8:43.2:1, 1.9:43.2:1, 2:43.2:1, 1:43.3:1, 1:43.3:1.1, 1:43.3:1.2, 1:43.3:1.3, 1:43.3:1.4, 1:43.3:1.5, 1:43.3:1.6, 1:43.3:1.7, 1:43.3:1.8, 1:43.3:1.9, 1:43.3:2, 1.1:43.3:1, 1.2:43.3:1, 1.3:43.3:1, 1.4:43.3:1, 1.5:43.3:1, 1.6:43.3:1, 1.7:43.3:1, 1.8:43.3:1, 1.9:43.3:1, 2:43.3:1, 1:43.4:1, 1:43.4:1.1, 1:43.4:1.2, 1:43.4:1.3, 1:43.4:1.4, 1:43.4:1.5, 1:43.4:1.6, 1:43.4:1.7, 1:43.4:1.8, 1:43.4:1.9, 1:43.4:2, 1.1:43.4:1, 1.2:43.4:1, 1.3:43.4:1, 1.4:43.4:1, 1.5:43.4:1, 1.6:43.4:1, 1.7:43.4:1, 1.8:43.4:1, 1.9:43.4:1, 2:43.4:1, 1:43.5:1, 1:43.5:1.1, 1:43.5:1.2, 1:43.5:1.3, 1:43.5:1.4, 1:43.5:1.5, 1:43.5:1.6, 1:43.5:1.7, 1:43.5:1.8, 1:43.5:1.9, 1:43.5:2, 1.1:43.5:1, 1.2:43.5:1, 1.3:43.5:1, 1.4:43.5:1, 1.5:43.5:1, 1.6:43.5:1, 1.7:43.5:1, 1.8:43.5:1, 1.9:43.5:1, 2:43.5:1, 1:43.6:1, 1:43.6:1.1, 1:43.6:1.2, 1:43.6:1.3, 1:43.6:1.4, 1:43.6:1.5, 1:43.6:1.6, 1:43.6:1.7, 1:43.6:1.8, 1:43.6:1.9, 1:43.6:2, 1.1:43.6:1, 1.2:43.6:1, 1.3:43.6:1, 1.4:43.6:1, 1.5:43.6:1, 1.6:43.6:1, 1.7:43.6:1, 1.8:43.6:1, 1.9:43.6:1, 2:43.6:1, 1:43.7:1, 1:43.7:1.1, 1:43.7:1.2, 1:43.7:1.3, 1:43.7:1.4, 1:43.7:1.5, 1:43.7:1.6, 1:43.7:1.7, 1:43.7:1.8, 1:43.7:1.9, 1:43.7:2, 1.1:43.7:1, 1.2:43.7:1, 1.3:43.7:1, 1.4:43.7:1, 1.5:43.7:1, 1.6:43.7:1, 1.7:43.7:1, 1.8:43.7:1, 1.9:43.7:1, 2:43.7:1, 1:43.8:1, 1:43.8:1.1, 1:43.8:1.2, 1:43.8:1.3, 1:43.8:1.4, 1:43.8:1.5, 1:43.8:1.6, 1:43.8:1.7, 1:43.8:1.8, 1:43.8:1.9, 1:43.8:2, 1.1:43.8:1, 1.2:43.8:1, 1.3:43.8:1, 1.4:43.8:1, 1.5:43.8:1, 1.6:43.8:1, 1.7:43.8:1, 1.8:43.8:1, 1.9:43.8:1, 2:43.8:1, 1:43.9:1, 1:43.9:1.1, 1:43.9:1.2, 1:43.9:1.3, 1:43.9:1.4, 1:43.9:1.5, 1:43.9:1.6, 1:43.9:1.7, 1:43.9:1.8, 1:43.9:1.9, 1:43.9:2, 1.1:43.9:1, 1.2:43.9:1, 1.3:43.9:1, 1.4:43.9:1, 1.5:43.9:1, 1.6:43.9:1, 1.7:43.9:1, 1.8:43.9:1, 1.9:43.9:1, 2:43.9:1, 1:44:1, 1:44:1.1, 1:44:1.2, 1:44:1.3, 1:44:1.4, 1:44:1.5, 1:44:1.6, 1:44:1.7, 1:44:1.8, 1:44:1.9, 1:44:2, 1.1:44:1, 1.2:44:1, 1.3:44:1, 1.4:44:1, 1.5:44:1, 1.6:44:1, 1.7:44:1, 1.8:44:1, 1.9:44:1, 2:44:1, 1:45:1, 1:45:1.1, 1:45:1.2, 1:45:1.3, 1:45:1.4, 1:45:1.5, 1:45:1.6, 1:45:1.7, 1:45:1.8, 1:45:1.9, 1:45:2, 1.1:45:1, 1.2:45:1, 1.3:45:1, 1.4:45:1, 1.5:45:1, 1.6:45:1, 1.7:45:1, 1.8:45:1, 1.9:45:1, or 2:45:1. For example, in one embodiment, the ratio of amounts for each active agent is about (1):(43.33):(1.67) for hydrocodone or a salt thereof: acetaminophen or a salt thereof: promethazine or a pharmaceutically acceptable salt thereof, respectively. In one embodiment a pharmaceutically acceptable salt of hydrocodone, acetaminophen or promethazine is provided. In one embodiment an opioid analgesic agent (such as hydrocodone or oxycodone or a salt thereof), acetaminophen or a salt thereof; and promethazine or a salt thereof are present in a bi-layer tablet that comprises an immediate release and a controlled release layer.

In another embodiment, the composition comprises oxycodone, a pharmaceutically acceptable salt or its thiosemicarbazone, p-nitrophenylhydrazone, o-methyloxime, semicarbazone, or bis (methylcarbamate) (each of the foregoing being a hydrocodone agent or derivative); acetaminophen or a salt thereof; and promethazine or a salt thereof. Furthermore, the oxycodone or a salt thereof is present in a range of about 1 mg to about 200 mg, including but not limited to 1.0 mg, 1.5 mg, 2.5 mg, 3.0 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg or 20 mg, 30 mg, 40 mg, 50 mg, 70 mg, 100 mg, 130 mg, 160, 190 mg, 200 mg. Furthermore, the acetaminophen or a salt thereof is in a range of between about 200 mg to about 1000 mg, including but not limited to 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. The compositions can further comprise between about 0.5 mg to about 200 mg of an antihistamine (e.g., promethazine or a salt thereof), including but not limited to 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11.0 mg, 11.5 mg, 12.0 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg. In one embodiment oxycodone or a salt thereof, acetaminophen or a salt thereof and promethazine or a salt thereof are present in a bi-layer tablet that comprises an immediate release and a controlled release layer.

In one embodiment, the composition comprises promethazine or a salt thereof in an amount of 12.5 mg. In one embodiment, the compositions of the invention comprise oxycodone or a salt thereof, acetaminophen or a salt thereof and promethazine or a salt thereof, wherein the composition comprises the agents in a weight ratio of about (1 to 2):(40 to 45):(1 to 2), respectively. In one embodiment a pharmaceutically acceptable salt of oxycodone, acetaminophen or promethazine is provided. For example, in one embodiment, the weight ratio of amounts for each active agent is about (1):(43.33):(1.67) for oxycodone or a salt thereof, acetaminophen or a salt thereof and promethazine or a salt thereof, respectively. In one embodiment, the compositions of the invention comprise an antihistamine (e.g., promethazine or a salt thereof) at a lower dosage than that which the antihistamine is administered alone. In one embodiment, the antihistamine is provided in the composition at a dosage to prevent sedation, which may be observed with relatively higher dosages of promethazine or a salt thereof. Thus in some embodiments, promethazine is provided at 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11.0 mg, 11.5 mg, 12.0 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg. Therefore, an antihistamine or antiemetic (e.g., promethazine or a salt thereof) can be provided at a dosage that is effective for reducing adverse affects associated with the opioid analgesic or non-opioid analgesic, but is at a relative low enough dosage (e.g., given the subject's weight) to prevent sedation associated with the antihistamine or antiemetic. Examples of adverse effects include acute liver toxicity, allergic reactions such as swelling, difficulty breathing, closing of throat, abdominal pain, nausea, unusual bleeding or bruising. In one embodiment oxycodone or a salt thereof, acetaminophen or a salt thereof; and promethazine or a salt thereof are present in a bi-layer tablet that comprises an immediate release and a controlled release layer.

In one embodiment, the compositions of the invention comprise 6-8 mg of hydrocodone or a salt thereof (such as about 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, or 8.0 mg,), 310-330 mg of acetaminophen (such as about 310 mg, 315 mg, 320 mg, or 325 mg), and 5-13 mg of promethazine or a salt thereof (such as about 10 mg, 10.5 mg, 11.0 mg, 11.5 mg, 12.0 mg, 12.5 mg, 13.0, mg, 13.5 mg, 14.0 mg, 14.5 mg, or 15 mg). In a further embodiment a pharmaceutically acceptable salt of hydrocodone, acetaminophen or promethazine is provided. The hydrocodone and the acetaminophen can be formulated using conventional technologies to provide for an extended time release over a desired dosage interval. All or some of the promethazine can be formulated for immediate release to help abate common adverse effects associated with the hydrocodone and acetaminophen including nausea, vomiting, other gastric upsets, skin rashes, allergic reactions such as swelling, difficulty breathing, closing of throat, abdominal pain, unusual bleeding or bruising, sedation, CNS depression, or respiratory depression. In one embodiment hydrocodone, acetaminophen; and promethazine are present in a bi-layer tablet that comprises an immediate release and a controlled release layer.

In one embodiment, the compositions of the invention comprise from 1% to 20% by weight of an antihistamine (such as 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20%); from 10% to 80% by weight a non-opioid analgesic (such as 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, 45%, 45.5%, 46%, 46.5%, 47%, 47.5%, 48%, 48.5%, 49%, 49.5%, 50%, 50.5%, 51%, 51.5%, 52%, 52.5%, 53%, 53.5%, 54%, 54.5%, 55%, 55.5%, 56%, 56.5%, 57%, 57.5%, 58%, 58.5%, 59%, 59.5%, 60%, 60.5%, 61%, 61.5%, 62%, 62.5%, 63%, 63.5%, 64%, 64.5%, 65%, 65.5%, 66%, 66.5%, 67%, 67.5%, 68%, 68.5%, 69%, 69.5%, 70%, 70.5%, 71%, 71.5%, 72%, 72.5%, 73%, 73.5%, 74%, 74.5%, 75%, 75.5%, 76%, 76.5%, 77%, 77.5%, 78%, 78.5%, 79%, 79.5%, 80%); and from 1% to 20% by weight of an opioid analgesic (such as 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20%). In one embodiment an opioid analgesic agent, a non-opioid analgesic and an antihistamine are present in a bi-layer tablet that comprises an immediate release and a controlled release layer.

In one embodiment, the compositions of the invention comprise 6-8 mg of oxycodone HCL (such as about 7.5 mg), 310-330 mg of acetaminophen (such as about 325 mg), and 6-15 mg of promethazine HCL (such as about 12.5 mg). The oxycodone HCL and the acetaminophen can be formulated using conventional technologies to provide for an extended time release over a desired dosage interval. All or some of the promethazine can be formulated for immediate release. In one embodiment the composition is in the form of a bi-layer tablet comprising an immediate-release layer comprising promethazine HCL and a controlled-release layer and a controlled release layer comprising acetaminophen and oxycodone or a salt thereof.

In one embodiment, administration of the composition disclosed herein that comprises an antiemetic agent (such as promethazine or a salt thereof) can produce an outcome in a subject, such as reduced, abated or eliminated adverse effects associated with the administration of an opioid agent or non-opioid agent, such as oxycodone HCL, hydrocodone bitartrate and acetaminophen. Reduced, abated or eliminated adverse effects include but are not limited to including nausea, vomiting, other gastric upsets, skin rashes, allergic reactions such as swelling, difficulty breathing, closing of throat, abdominal pain, unusual bleeding or bruising, sedation, CNS depression, or respiratory depression or any combination thereof.

The dosages and concentrations of active agents in the compositions may be varied as desired, as further described herein. Depending on the subject and/or condition being treated and on the administration route, the active agent in a composition can generally be administered in dosages of 0.01 mg to 500 mg per kg body weight per day, e.g. about 20 mg/day for an average person. The dosage can be adjusted based on the mode of administration. A typical dosage may be one administration daily or multiple administrations daily.

Of course for controlled-release dosage forms the unit dose can be designed for administration over a defined period of time. In some embodiments, dosage for one or a combination of agents can be from about 0.01 to 5 mg, 1 to 10 mg, 5 to 20 mg, 10 to 50 mg, 20 to 100 mg, 50 to 150 mg, 100 to 250 mg, 150 to 300 mg, 250 to 500 mg, 300 to 600 mg or 500 to 1000 mg V/kg body weight. Dose levels can vary as a function of the specific compound, the severity of the symptoms and the susceptibility of the subject to adverse effects.

In another embodiment a composition comprises multiple active agents at the same or different dosages, where the composition comprises an effective amount of: an opioid analgesic; an antiemetic or antihistamine; and a stimulant. In some embodiments the composition may further comprise a barbiturate or a non-opioid active agent, or both. The dosage can be adjusted according to the particular actives selected.

In one embodiment, a composition comprises an effective amount of: an opioid analgesic; an antiemetic or antihistamine; and a stimulant. In this embodiment the antiemetic or an antihistamine (e.g., promethazine or a salt thereof), that is present at about 0.5 mg to about 60 mg, including but not limited to a dose of about 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11.0 mg, 11.5 mg, 12.0 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg. In one embodiment, the antiemetic or antihistamine is promethazine or a salt thereof. In various other embodiments, the antihistamine or antiemetic is one described herein above. As described herein, in some embodiments, the antihistamine or antiemetic is a component of an immediate-release formulation. For example, in a further embodiment, the immediate-release is in a capsule, a tablet, a transdermal means, or achieved through injection, intramuscular administration or other means disclosed herein. In one embodiment an opioid analgesic agent, a stimulant and an antihistamine are present in a bi-layer tablet that comprises an immediate release and a controlled release layer. In one embodiment the stimulant and an antihistamine are present in the immediate release layer and the opioid analgesic agent is present in the controlled release layer. In another embodiment an opioid analgesic agent, a non-opioid analgesic, a stimulant and an antihistamine are present in a bi-layer tablet that comprises an immediate release and a controlled release layer. In one embodiment the stimulant and an antihistamine are present in the immediate release layer and the opioid analgesic agent and a non-opioid analgesic are present in the controlled release layer.

In a further embodiment, a composition of the invention comprises: an effective amount of an opioid analgesic agent; an antiemetic or antihistamine agent; and a stimulant agent or a non-opioid agent, or both. In one embodiment each agent is present at a dose of about 0.5 mg to about 20 mg, 5 mg to 30 mg, 10 mg to 100 mg, including but not limited to about 0.5 mg, 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 25 mg, 30 mg, 35 mg, 40 mg, 45 mg, or 50 mg. In one embodiment an opioid analgesic agent, a stimulant and an antihistamine are present in a bi-layer tablet that comprises an immediate release and a controlled release layer. In one embodiment the stimulant and an antihistamine are present in the immediate release layer and the opioid analgesic agent is present in the controlled release layer.

In yet a further embodiment, the composition comprising: an effective amount of an opioid analgesic, a stimulant and optionally an antiemetic or antihistamine. In one embodiment the composition comprises a stimulant at a dose of about 1 mg to about 350 mg, 5 mg to 25 mg, 10 mg to 50 mg, 25 to 100 mg, 50 to 150 mg, 100 mg to 250 mg, 75 mg to 350 mg, including but not limited to about 1.0 mg, 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 25 mg, 30 mg, 35 mg, 40 mg, 45 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, or 350 mg. In one embodiment an opioid analgesic agent, a stimulant and an antihistamine are present in a bi-layer tablet that comprises an immediate release and a controlled release layer. In one embodiment the stimulant and an antihistamine are present in the immediate release layer and the opioid analgesic agent is present in the controlled release layer.

In various embodiments, a composition of the invention comprises: an opioid analgesic, a stimulant, and an antiemetic or antihistamine, wherein the relative ratio by weight of each of an opioid:a stimulant:an antiemetic or antihistamine is about (1 to 2):(40 to 45):(1 to 2), such as about 1:40:1, 1:40:1.1, 1:40:1.2, 1:40:1.3, 1:40:1.4, 1:40:1.5, 1:40:1.6, 1:40:1.7, 1:40:1.8, 1:40:1.9, 1:40:2, 1.1:40:1, 1.2:40:1, 1.3:40:1, 1.4:40:1, 1.5:40:1, 1.6:40:1, 1.7:40:1, 1.8:40:1, 1.9:40:1, 2:40:1, 1:41:1, 1:41:1.1, 1:41:1.2, 1:41:1.3, 1:41:1.4, 1:41:1.5, 1:41:1.6, 1:41:1.7, 1:41:1.8, 1:41:1.9, 1:41:2, 1.1:41:1, 1.2:41:1, 1.3:41:1, 1.4:41:1, 1.5:41:1, 1.6:41:1, 1.7:41:1, 1.8:41:1, 1.9:41:1, 2:41:1, 1:42:1, 1:42:1.1, 1:42:1.2, 1:42:1.3, 1:42:1.4, 1:42:1.5, 1:42:1.6, 1:42:1.7, 1:42:1.8, 1:42:1.9, 1:42:2, 1.1:42:1, 1.2:42:1, 1.3:42:1, 1.4:42:1, 1.5:42:1, 1.6:42:1, 1.7:42:1, 1.8:42:1, 1.9:42:1, 2:42:1, 1:43:1, 1:43:1.1, 1:43:1.2, 1:43:1.3, 1:43:1.4, 1:43:1.5, 1:43:1.6, 1:43:1.7, 1:43:1.8, 1:43:1.9, 1:43:2, 1.1:43:1, 1.2:43:1, 1.3:43:1, 1.4:43:1, 1.5:43:1, 1.6:43:1, 1.7:43:1, 1.8:43:1, 1.9:43:1, 2:43:1, 1:43.1:1, 1:43.1:1.1, 1:43.1:1.2, 1:43.1:1.3, 1:43.1:1.4, 1:43.1:1.5, 1:43.1:1.6, 1:43.1:1.7, 1:43.1:1.8, 1:43.1:1.9, 1:43.1:2, 1.1:43.1:1, 1.2:43.1:1, 1.3:43.1:1, 1.4:43.1:1, 1.5:43.1:1, 1.6:43.1:1, 1.7:43.1:1, 1.8:43.1:1, 1.9:43.1:1, 2:43.1:1, 1:43.2:1, 1:43.2:1.1, 1:43.2:1.2, 1:43.2:1.3, 1:43.2:1.4, 1:43.2:1.5, 1:43.2:1.6, 1:43.2:1.7, 1:43.2:1.8, 1:43.2:1.9, 1:43.2:2, 1.1:43.2:1, 1.2:43.2:1, 1.3:43.2:1, 1.4:43.2:1, 1.5:43.2:1, 1.6:43.2:1, 1.7:43.2:1, 1.8:43.2:1, 1.9:43.2:1, 2:43.2:1, 1:43.3:1, 1:43.3:1.1, 1:43.3:1.2, 1:43.3:1.3, 1:43.3:1.4, 1:43.3:1.5, 1:43.3:1.6, 1:43.3:1.7, 1:43.3:1.8, 1:43.3:1.9, 1:43.3:2, 1.1:43.3:1, 1.2:43.3:1, 1.3:43.3:1, 1.4:43.3:1, 1.5:43.3:1, 1.6:43.3:1, 1.7:43.3:1, 1.8:43.3:1, 1.9:43.3:1, 2:43.3:1, 1:43.4:1, 1:43.4:1.1, 1:43.4:1.2, 1:43.4:1.3, 1:43.4:1.4, 1:43.4:1.5, 1:43.4:1.6, 1:43.4:1.7, 1:43.4:1.8, 1:43.4:1.9, 1:43.4:2, 1.1:43.4:1, 1.2:43.4:1, 1.3:43.4:1, 1.4:43.4:1, 1.5:43.4:1, 1.6:43.4:1, 1.7:43.4:1, 1.8:43.4:1, 1.9:43.4:1, 2:43.4:1, 1:43.5:1, 1:43.5:1.1, 1:43.5:1.2, 1:43.5:1.3, 1:43.5:1.4, 1:43.5:1.5, 1:43.5:1.6, 1:43.5:1.7, 1:43.5:1.8, 1:43.5:1.9, 1:43.5:2, 1.1:43.5:1, 1.2:43.5:1, 1.3:43.5:1, 1.4:43.5:1, 1.5:43.5:1, 1.6:43.5:1, 1.7:43.5:1, 1.8:43.5:1, 1.9:43.5:1, 2:43.5:1, 1:43.6:1, 1:43.6:1.1, 1:43.6:1.2, 1:43.6:1.3, 1:43.6:1.4, 1:43.6:1.5, 1:43.6:1.6, 1:43.6:1.7, 1:43.6:1.8, 1:43.6:1.9, 1:43.6:2, 1.1:43.6:1, 1.2:43.6:1, 1.3:43.6:1, 1.4:43.6:1, 1.5:43.6:1, 1.6:43.6:1, 1.7:43.6:1, 1.8:43.6:1, 1.9:43.6:1, 2:43.6:1, 1:43.7:1, 1:43.7:1.1, 1:43.7:1.2, 1:43.7:1.3, 1:43.7:1.4, 1:43.7:1.5, 1:43.7:1.6, 1:43.7:1.7, 1:43.7:1.8, 1:43.7:1.9, 1:43.7:2, 1.1:43.7:1, 1.2:43.7:1, 1.3:43.7:1, 1.4:43.7:1, 1.5:43.7:1, 1.6:43.7:1, 1.7:43.7:1, 1.8:43.7:1, 1.9:43.7:1, 2:43.7:1, 1:43.8:1, 1:43.8:1.1, 1:43.8:1.2, 1:43.8:1.3, 1:43.8:1.4, 1:43.8:1.5, 1:43.8:1.6, 1:43.8:1.7, 1:43.8:1.8, 1:43.8:1.9, 1:43.8:2, 1.1:43.8:1, 1.2:43.8:1, 1.3:43.8:1, 1.4:43.8:1, 1.5:43.8:1, 1.6:43.8:1, 1.7:43.8:1, 1.8:43.8:1, 1.9:43.8:1, 2:43.8:1, 1:43.9:1, 1:43.9:1.1, 1:43.9:1.2, 1:43.9:1.3, 1:43.9:1.4, 1:43.9:1.5, 1:43.9:1.6, 1:43.9:1.7, 1:43.9:1.8, 1:43.9:1.9, 1:43.9:2, 1.1:43.9:1, 1.2:43.9:1, 1.3:43.9:1, 1.4:43.9:1, 1.5:43.9:1, 1.6:43.9:1, 1.7:43.9:1, 1.8:43.9:1, 1.9:43.9:1, 2:43.9:1, 1:44:1, 1:44:1.1, 1:44:1.2, 1:44:1.3, 1:44:1.4, 1:44:1.5, 1:44:1.6, 1:44:1.7, 1:44:1.8, 1:44:1.9, 1:44:2, 1.1:44:1, 1.2:44:1, 1.3:44:1, 1.4:44:1, 1.5:44:1, 1.6:44:1, 1.7:44:1, 1.8:44:1, 1.9:44:1, 2:44:1, 1:45:1, 1:45:1.1, 1:45:1.2, 1:45:1.3, 1:45:1.4, 1:45:1.5, 1:45:1.6, 1:45:1.7, 1:45:1.8, 1:45:1.9, 1:45:2, 1.1:45:1, 1.2:45:1, 1.3:45:1, 1.4:45:1, 1.5:45:1, 1.6:45:1, 1.7:45:1, 1.8:45:1, 1.9:45:1, or 2:45:1. In one embodiment an opioid analgesic agent, a stimulant and an antihistamine are present in a bi-layer tablet that comprises an immediate release and a controlled release layer. In one embodiment the stimulant and an antihistamine are present in the immediate release layer and the opioid analgesic agent is present in the controlled release layer.

In another embodiment, compositions are provided that comprise an effective amount of an opioid (such as hydrocodone, fentanyl or oxycodone or a salt thereof); a non-opioid (such as acetaminophen or naproxen salt thereof); and a barbiturate (such as butalbital or a salt thereof). In some embodiments the compositions further comprise an antiemetic (such as promethazine or a salt thereof). In some embodiments the composition further comprises a stimulant agent. In some embodiments the barbiturate is present at a dose of 1 mg to about 350 mg, 5 mg to 25 mg, 10 mg to 50 mg, 25 to 100 mg, 50 to 150 mg, 100 mg to 250 mg, 75 mg to 350 mg, including but not limited to about 1.0 mg, 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 25 mg, 30 mg, 35 mg, 40 mg, 45 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, or 350 mg.

In another embodiment the compositions comprise an effective amount of an opioid (such as hydrocodone, fentanyl or oxycodone or a salt thereof); a non-opioid agent (such as acetaminophen or naproxen or a salt thereof); and a barbiturate (such as butalbital or a salt thereof). In one embodiment the opioid agent (such as hydrocodone or oxycodone or a salt thereof) is present in a range of about 1 mg to about 200 mg, including but not limited to 1.0 mg, 1.5 mg, 2.5 mg, 3.0 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg or 20 mg, 30 mg, 40 mg, 50 mg, 70 mg, 100 mg, 130 mg, 160, 190 mg, 200 mg. Furthermore, the non-opioid agent (such as acetaminophen or naproxen or a salt thereof) is present in a range of between about 200 mg to about 1000 mg, including but not limited to 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. Additionally, the barbiturate (e.g., butalbital or a salt thereof) is present at a dose between about 0.5 mg to about 200 mg, including but not limited to, 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11.0 mg, 11.5 mg, 12.0 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg. In one embodiment an opioid analgesic agent, a non-opioid agent, and a barbiturate agent are present in a bi-layer tablet that comprises an immediate release and a controlled release layer. In a further embodiment the bi-layer tablet comprises an antiemetic agent, such as an antihistamine. In one embodiment the antihistamine is present in the immediate release layer and the opioid analgesic agent, non-opioid agent, and barbiturate agent are present in the controlled release layer.

In another embodiment compositions are provided that comprise an effective amount of a barbiturate agent (such as butalbital or a salt thereof); a non-opioid agent (such as acetaminophen or naproxen or a salt thereof); and a stimulant agent (such as caffeine or a salt thereof). In one embodiment the barbiturate agent (such as butalbital or a salt thereof); is present in a range of about 0.5 mg to about 200 mg, including but not limited to 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11.0 mg, 11.5 mg, 12.0 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg. Furthermore, the non-opioid agent (such as acetaminophen or naproxen or a salt thereof) is present in a range of between about 200 mg to about 1000 mg, including but not limited to 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. Additionally, the stimulant agent (e.g., caffeine) is present at a dose from about 0.5 mg to about 200 mg including but not limited to 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11.0 mg, 11.5 mg, 12.0 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg. In one embodiment a stimulant agent, a non-opioid agent, and a barbiturate agent are present in a bi-layer tablet that comprises an immediate release and a controlled release layer. In one embodiment the stimulant is present in the immediate release layer and the non-opioid analgesic agent and barbiturate are present in the controlled release layer. In a further embodiment the bi-layer tablet comprises an antiemetic agent, such as an antihistamine (e.g., promethazine). In one embodiment the stimulant and an antihistamine are present in the immediate release layer and the non-opioid analgesic agent and barbiturate are present in the controlled release layer.

In another embodiment compositions are provided that comprise an effective amount of a barbiturate and a stimulant. In one embodiment the composition comprises a stimulant at a dose of about 1 mg to about 350 mg (such as 5 mg to 25 mg, 10 mg to 50 mg, 25 to 100 mg, 50 to 150 mg, 100 mg to 250 mg, 75 mg to 350 mg) including but not limited to about 1.0 mg, 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 25 mg, 30 mg, 35 mg, 40 mg, 45 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, or 350 mg. Additionally, the barbiturate agent (such as butalbital or a salt thereof); is present in a range of about 0.5 mg to about 200 mg, including but not limited to 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11.0 mg, 11.5 mg, 12.0 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg. In one embodiment, a barbiturate agent, and a stimulant are present in a bi-layer tablet that comprises an immediate release and a controlled release layer. In a further embodiment the bi-layer tablet further comprises an antiemetic agent, such as an antihistamine (e.g. promethazine or a salt thereof). In one embodiment the stimulant and an antihistamine are present in the immediate release layer and the barbiturate agent is present in the controlled release layer.

In another embodiment the compositions comprise an effective amount of a non-opioid agent (such as naproxen or ibuprofen or a salt thereof) and a stimulant (such as caffeine or a salt thereof). In some embodiments the non-opioid agent (such as naproxen or ibuprofen or a salt thereof) is present in a range of between about 200 mg to about 1000 mg, including but not limited to 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. In these embodiments the compositions comprise a stimulant at a dose of about 1 mg to about 350 mg, (such as 5 mg to 25 mg, 10 mg to 50 mg, 25 to 100 mg, 50 to 150 mg, 100 mg to 250 mg, or 75 mg to 350 mg), including but not limited to about 1.0 mg, 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 25 mg, 30 mg, 35 mg, 40 mg, 45 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, or 350 mg. In one embodiment a non-opioid agent and a stimulant are formulated as a bi-layer tablet that comprises an immediate release and a controlled release layer. In one example naproxen and caffeine are formulated in a bi-layer tablet. In one embodiment the caffeine is present in the immediate release layer and naproxen is present in the controlled release layer.

In one embodiment, the compositions of the invention comprise an effective amount of propoxyphene or a salt thereof and a non-opioid agent (such as naproxen or a salt thereof). In some embodiments the composition further comprises an antiemetic (such as promethazine or a salt thereof). In some embodiments the compositions further comprise a stimulant agent. In one embodiment, the propoxyphene or salt thereof is present in a range of about 1.0 mg to about 100 mg, including but not limited to 11.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, or 100 mg. Furthermore, the non-opioid agent is in a range of about 200 mg to about 1000 mg, including but not limited to 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. In one embodiment propoxyphene or a salt thereof and naproxen (such as naproxen sodium or naproxen magnesium) are present in a bi-layer tablet. In a further embodiment, the composition comprises an antiemetic or an antihistamine (e.g., promethazine or a salt thereof). In one embodiment the antihistamine is present in the immediate release layer and propoxyphene and naproxen are present in the controlled release layer.

In another embodiment, the compositions described herein comprise an effective amount of an antiemetic or an antihistamine (e.g., promethazine or a salt thereof), that is present in the range of at about 0.5 mg to about 60 mg, including but not limited to a dose of about 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11.0 mg, 11.5 mg, 12.0 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 31 mg, 32 mg, 33 mg, 34 mg, 35 mg, 36 mg, 37 mg, 38 mg, 39 mg, 40 mg, 41 mg, 12 mg, 43 mg, 44 mg, 45 mg, 46 mg, 47 mg, 48 mg, 49 mg, 50 mg, 55 mg, 60 mg. In one embodiment, the antiemetic or antihistamine is promethazine or a salt thereof. In various other embodiments, the antihistamine or antiemetic is another described herein above. As described herein, in some embodiments, the antihistamine or antiemetic is a component of an immediate-release formulation. For example, in a further embodiment, the immediate-release is in a lollipop, capsule, a tablet, a transdermal means, through injection, intramuscular administration or other means disclosed herein.

Dosage Forms

Oral Dosage Forms

In one embodiment the invention relates to methods and compositions formulated for oral delivery to a subject in need. In one embodiment a composition is formulated so as to deliver one or more pharmaceutically active agents to a subject through a mucosa layer in the mouth or esophagus. In another embodiment the composition is formulated to deliver one or more pharmaceutically active agents to a subject through a mucosa layer in the stomach and/or intestines.

In one embodiment compositions are provided in modified release dosage forms (such as immediate release, controlled release or both), which comprise an effective amount of an opioid analgesic (such as oxycodone or hydrocodone or a salt thereof), a non-opioid analgesic (such as acetaminophen, naproxen or ibuprofen or a salt thereof) and an antihistamine (such as promethazine or a salt thereof); and one or more release controlling excipients as described herein. Suitable modified release dosage vehicles include, but are not limited to, hydrophilic or hydrophobic matrix devices, water-soluble separating layer coatings, enteric coatings, osmotic devices, multiparticulate devices, and combinations thereof. The compositions may also comprise non-release controlling excipients.

In another embodiment compositions are provided in enteric coated dosage forms. The compositions can also comprise non-release controlling excipients.

In another embodiment compositions are provided in effervescent dosage forms. The compositions can also comprise non-release controlling excipients.

In another embodiment compositions can be provided in a dosage form that has at least one component that can facilitate the immediate release of an active agent, and at least one component that can facilitate the controlled release of an active agent. In a further embodiment the dosage form can be capable of giving a discontinuous release of the compound in the form of at least two consecutive pulses separated in time from 0.1 up to 24 hours. The compositions can comprise one or more release controlling and non-release controlling excipients, such as those excipients suitable for a disruptable semi-permeable membrane and as swellable substances.

In another embodiment compositions are provided in a dosage form for oral administration to a subject, which comprise one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

In one embodiment the compositions are in the form of enteric-coated granules, as controlled-release capsules for oral administration. The compositions can further comprise cellulose, disodium hydrogen phosphate, hydroxypropyl cellulose, hypromellose, lactose, mannitol, and sodium lauryl sulfate.

In another embodiment the compositions are in the form of enteric-coated pellets, as controlled-release capsules for oral administration. The compositions can further comprise glyceryl monostearate 40-50, hydroxypropyl cellulose, hypromellose, magnesium stearate, methacrylic acid copolymer type C, polysorbate 80, sugar spheres, talc, and triethyl citrate.

In another embodiment the compositions are enteric-coated controlled-release tablets for oral administration. The compositions can further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, and yellow ferric oxide.

In another embodiment the compositions can further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

The compositions provided herein can be in unit-dosage forms or multiple-dosage forms. Unit-dosage forms, as used herein, refer to physically discrete units suitable for administration to human or non-human animal subjects and packaged individually. Each unit-dose can contain a predetermined quantity of an active ingredient(s) sufficient to produce the desired therapeutic effect, in association with the required pharmaceutical carriers or excipients. Examples of unit-dosage forms include, but are not limited to, ampules, syringes, and individually packaged tablets and capsules. Unit-dosage forms may be administered in fractions or multiples thereof. A multiple-dosage form is a plurality of identical unit-dosage forms packaged in a single container, which can be administered in segregated unit-dosage form. Examples of multiple-dosage forms include, but are not limited to, vials, bottles of tablets or capsules, or bottles of pints or gallons. In another embodiment the multiple dosage forms comprise different pharmaceutically active agents. For example a multiple dosage form can be provided which comprises a first dosage element comprising an immediate release form of an antihistamine (such as in a liquid form) and a second dosage element comprising an opioid and/or non opioid analgesic, which can be in a modified release form (such as immediate release, controlled release, or extended release form).

In this example a pair of dosage elements can make a single unit dosage. In one embodiment a kit is provided comprising multiple unit dosages, wherein each unit comprises a first dosage element comprising an immediate release form of an antihistamine (such as in a liquid form) and a second dosage element comprising an opioid or non-opioid analgesic or both, which can be in a modified release form (such as immediate release or controlled release, or both). In another embodiment the kit further comprises a set of instructions. In yet a further embodiment the antihistamine is promethazine or a pharmaceutically acceptable salt thereof, the opioid analgesic is oxycodone or hydrocodone or pharmaceutically acceptable salt thereof, the non-opioid analgesic is acetaminophen or a pharmaceutically acceptable salt thereof.

In one embodiment compositions can be formulated in various dosage forms for oral, parenteral, and topical administration. The compositions may also be formulated as a modified release dosage form, including immediate-, delayed-, extended-, prolonged-, sustained-, pulsatile-, controlled-, extended, accelerated- and fast-, targeted-, programmed-release, and gastric retention dosage forms. These dosage forms can be prepared according to known methods and techniques (see, Remington: The Science and Practice of Pharmacy, supra; Modified-Release Drug Delivery Technology, Rathbone et al., Eds., Drugs and the Pharmaceutical Science, Marcel Dekker, Inc.: New York, N.Y., 2002; Vol. 126, which is herein incorporated by reference in its entirety).

In various embodiments of the invention, the compositions are in one or more dosage form. For example, a composition can be administered in a solid or liquid form. Examples of solid dosage forms include but are not limited to discrete units in capsules or tablets, as a powder or granule, or present in a tablet conventionally formed by compression molding. Such compressed tablets may be prepared by compressing in a suitable machine the three or more agents and a pharmaceutically acceptable carrier. The molded tablets can be optionally coated or scored, having indicia inscribed thereon and can be so formulated as to cause immediate, substantially immediate, slow, controlled or extended release of the opioid analgesics (such as oxycodone or hydrocodone) and/or the non-opioid analgesics (such as acetaminophen) and or the antihistamine (such as promethazine). Furthermore, dosage forms of the invention can comprise acceptable carriers or salts known in the art, such as those described in the Handbook of Pharmaceutical Excipients, American Pharmaceutical Association (1986), incorporated by reference herein in its entirety.

In one embodiment, one or more pharmaceutically active agents are mixed with a pharmaceutical excipient to form a solid preformulation composition comprising a homogeneous mixture of compounds described herein. When referring to these compositions as "homogeneous", it is meant that the agents are dispersed evenly throughout the composition so that the composition can be subdivided into unit dosage forms such as tablets or capsules. This solid preformulation composition can then subdivided into unit dosage forms of the type described above comprising from, for example, about 1.0 mg to about 15 mg of an opioid, such as hydrocodone or oxycodone or a pharmaceutically acceptable salt thereof.

The compositions can be formulated, in the case of capsules or tablets, to be swallowed whole, for example with water. The inclusion of the side-effect-reducing agent such as an antihistamine or antiemetic to abate common symptoms of nausea and vomiting are believed beneficial in that promethazine or a salt thereof, or the like will eliminate or minimize the amount of discomfort. Adverse effects reduced or eliminated include but are not limited to nausea, vomiting, other gastric upsets, skin rashes, allergic reactions such as swelling, difficulty breathing, closing of throat, abdominal pain, unusual bleeding or bruising, CNS suppression and respiratory suppression.

Frequently, subjects taking opioids have adverse effects including vomiting that can occur shortly after taking a first or subsequent dose. As a consequence, a portion of the opioid dose is subsequently lost, making it difficult to accurately gauge replacement dosages for the subject, and for subjects outside of a hospital or clinic environment, there might not be any alternative form of pain medication readily available. As a consequence, subjects experiencing gastric discomfort such as vomiting will lack the beneficial effects of the opioid analgesic and experience the additional discomfort and enhanced pain associated with vomiting. This problem is solved by also administering promethazine or a salt thereof, which reduces side-effects.

The dosage forms described herein can be manufactured using processes that are well known to those of skill in the art. For example, for the manufacture of bi-layered tablets, the agents can be dispersed uniformly in one or more excipients, for example, using high shear granulation, low shear granulation, fluid bed granulation, or by blending for direct compression. Excipients include diluents, binders, disintegrants, dispersants, lubricants, glidants, stabilizers, surfactants and colorants. Diluents, also termed "fillers", can be used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders can impart cohesive qualities to a tablet formulation and can be used to help a tablet remain intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, waxes, natural and synthetic gums, e.g., acacia, tragacanth, sodium alginate, and synthetic polymers such as polymethacrylates and polyvinylpyrrolidone. Lubricants can also facilitate tablet manufacture; non-limiting examples thereof include magnesium stearate, calcium stearate, stearic acid, glyceryl behenate, and polyethylene glycol. Disintegrants can facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses, starches, gums and the like. Non-limiting examples of suitable glidants include silicon dioxide, talc and the like. Stabilizers can inhibit or retard drug decomposition reactions, including oxidative reactions. Surfactants can also include and can be anionic, cationic, amphoteric or nonionic. If desired, the tablets can also comprise nontoxic auxiliary substances such as pH buffering agents, preservatives, e.g., antioxidants, wetting or emulsifying agents, solubilizing agents, coating agents, flavoring agents, and the like.

Controlled-release formulations can comprise one or more combination of excipients that slow the release of the agents by coating or temporarily bonding or decreasing their solubility of the active agents. Examples of these excipients include cellulose ethers such as hydroxypropylmethylcellulose (e.g., Methocel K4M) or silicified microcrystalline cellulose, polyvinylacetate-based excipients such as, e.g., Kollidon SR, and polymers and copolymers based on methacrylates and methacrylic acid such as, e.g., Eudragit NE 30D. In one embodiment of the invention, the opioid analgesic or non-opioid agents (e.g., hydrocodone or oxycodone or a salt thereof, and acetaminophen or a salt thereof) are formulated for extended or controlled-release while the promethazine or a salt thereof is formulated for immediate release. In another embodiment, all agents are formulated for extended or controlled-release.

Immediate-release formulations can comprise one or more combination of excipients that allow for a rapid release of a pharmaceutically active agent (such as from 1 minute to 1 hour after administration), such as an anti-emetic or an antihistamine. In one embodiment an immediate release excipient can be microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, Avicel PH200, and combinations of such excipients.

Pharmaceutical carriers or vehicles suitable for administration of the compounds provided herein include all such carriers known to those skilled in the art to be suitable for the particular mode of administration. In addition, the compositions can one or more components that do not impair the desired action, or with components that supplement the desired action, or have another action. As noted above, the compositions can comprise additional (e.g., a fourth, fifth, sixth, etc.) additional active agents.

In one embodiment, the compositions comprise three or more pharmaceutically active agents wherein at least one active agent is formulated in an immediate release form. In this embodiment the immediate-release form can be included in an amount that is effective to shorten the time to its maximum concentration in the blood. By way of example, certain immediate-release pharmaceutical preparations are taught in United States Patent Publication US 2005/0147710A1 entitled, "Powder Compaction and Enrobing" which is incorporated herein in its entirety by reference.

In a further embodiment, a component of an immediate-release form or layer is a component that reduces abates or eliminates and/or suppresses an adverse effect associated with one or more opioid analgesics.

For example, the immediate-release active can be an antihistamine or an antiemetic, which reduces, abates or eliminates an adverse effect associated with opioid and/or non-opioid analgesics described herein.

In a further embodiment, all or less than the entire amount of the antiemetic or antihistamine agent is formulated in immediate-release form, as described herein.

A variety of known methods and materials may be used to bring about the immediate release. For instance, placement of the agent along an exterior of a tablet (e.g., coating the exterior or formulating the outer layer with the agent) and/or combined with forming a tablet by compressing the powder using low compaction can produce immediate-release of the agent from the composition.

In a specific embodiment, an effective amount of the promethazine or a salt thereof in immediate-release form may be coated onto a substrate. For example, where the extended release of one or more analgesics from a formulation is due to a controlled-release coating, an immediate-release layer comprising promethazine or a salt thereof can overcoat the controlled-release coating. In another example, an immediate-release layer can be coated onto the surface of a substrate wherein an opioid, a non-opioid agent, a barbiturate, or a stimulant is incorporated in a controlled release matrix. Where a plurality of controlled-release substrates (e.g., multiparticulate systems including pellets, spheres, beads and the like) are incorporated into a hard gelatin capsule, a side-effect-reducing compound can be incorporated into the gelatin capsule via inclusion of an amount of immediate-release promethazine or a salt thereof, as a powder or granulate within the capsule. Alternatively, the gelatin capsule itself can be coated with an immediate-release layer of promethazine. One skilled in the art recognizes still other alternative means of incorporating an immediate release side-effect-reducing compound into the unit dose. By including an effective amount of immediate-release side-effect-reducing compound in the unit dose, the experience of adverse effects including nausea, vomiting, other gastric upsets, skin rashes, allergic reactions such as swelling, difficulty breathing, closing of throat, abdominal pain, unusual bleeding or bruising, skin rashes, sedation, CNS depression, or respiratory depression in subjects can be significantly reduced.

In one embodiment, the composition comprises three or more active agents wherein at least one active agent is in controlled-release form. The controlled-release form can be in an amount that is effective to protect the agent from rapid elimination from the body. Certain preparations relating to the controlled release of a pharmaceutical are taught in United States Patent Publication US 2005/0147710A1 entitled, "Powder Compaction and Enrobing" which is incorporated herein in its entirety by reference. Examples of time release coated beads are disclosed in U.S. Application Publication No. 20080131517.

In a further embodiment, at least one pharmaceutically active agent in a controlled-release form is an opioid analgesic agent. In one embodiment of the invention, compositions comprise one or more carriers that protect the agents against rapid elimination from the body, such as time-release formulations or coatings. Such carriers include controlled-release formulations, including, for example, microencapsulated delivery systems. The active agents can be included in the pharmaceutically acceptable carrier in amounts sufficient to treat a subject's pain, with reduced adverse effects.

In certain embodiments the compositions are in oral-dosage form and comprise a matrix that includes, for example, a controlled-release material and an opioid or non-opioid analgesic. In certain embodiments, the matrix is compressible into a tablet and can be optionally overcoated with a coating that can control the release of the opioid or non-opioid analgesic from the composition. In this embodiment blood levels of analgesics are maintained within a therapeutic range over an extended period of time. In certain alternate embodiments, the matrix is encapsulated.

Tablets or capsules containing a composition described herein can be coated or otherwise compounded to provide a dosage form affording the advantage of prolonged action. For example, the tablet or capsule can contain an inner dosage and an outer dosage component, the latter being in the form of an envelope over the former. The two components can be separated by an enteric layer that serves to resist disintegration in the stomach and permit the inner component to pass intact into the duodenum or to be controlled in release. For controlled extended release, the capsule can also have micro drilled holes.

A coating comprising a side-effect-reducing compound, in immediate release form, can be added to the outside of a controlled-release tablet core to produce a final dosage form. Such a coating can be prepared by admixing a compound like promethazine with polyvinylpyrrolidone (PVP) 29/32 or hydroxypropyl methylcellulose (HPMC) and water/isopropyl alcohol and triethyl acetate. Such an immediate-release coating can be spray coated onto the tablet cores. The immediate-release coating can also be applied using a press-coating process with a blend consisting of 80% by weight promethazine and 20% by weight of lactose and hydroxypropyl methylcellulose type 2910. Press-coating techniques are known in the art and are described in U.S. Pat. No. 6,372,254, which is herein incorporated by reference in its entirety.

The immediate-release or controlled-release dosage forms described herein can also take the form of a bi-layered tablet, which comprises a first layer and a second layer. The first layer comprises a first drug that is an analgesic, antitussive, antihistamine, and antiemetic. The second layer comprises a second drug that is an analgesic, antitussive, antihistamine, and antiemetic. The second drug is the same as or different from the first drug. The bi-layered tablet can provide a plasma concentration within the therapeutic range of the second drug over a period which is coextensive with at least about 70% of the period (e.g., 12 hours) within which the bi-layered tablet provides a plasma concentration within the therapeutic range of the first drug.

In a further embodiment of the bi-layered tablet, one layer is an immediate release layer and the other layer is a controlled-release layer. In one example a bi-layered is formulated using the methods disclosed in U.S. Pat. No. 4,820,522, which is herein incorporated by reference in its entirety.

In one embodiment of the bi-layered tablet described herein, both layers can comprise an opioid analgesic, a non-opioid analgesic and a compound to reduce or suppress adverse effects.

In a further embodiment of the bi-layered tablet described herein, the immediate-release layer comprises promethazine or a salt thereof and the controlled release layer comprises hydrocodone or oxycodone or a pharmaceutically acceptable salt thereof. In one embodiment the immediate or controlled release layer can further comprise acetaminophen or naproxen or a salt thereof.

In one embodiment of the multi-layered tablet, the second drug can have a plasma half-life that differs from the plasma half-life of the first drug by at least about 2 hours.

In another embodiment, an effective amount of the antiemetic agent or antihistamine in an immediate-release form may be coated onto a substrate. For example, where the one or more opioid analgesics and one or more stimulant are components of a controlled-release formulation, an immediate-release layer comprising the antiemetic agent or antihistamine can overcoat the controlled-release formulation.

In another embodiment, the immediate-release layer can be coated onto the surface of a substrate having a controlled release matrix. Where a plurality of controlled-release substrates comprising an effective unit dose of a pharmaceutically active agent (e.g., multiparticulate systems including pellets, spheres, beads and the like) are incorporated into a hard gelatin capsule, another agent can be incorporated into the gelatin capsule via inclusion of an amount of immediate-release agent as a powder or granulate within the capsule. Alternatively, the gelatin capsule itself can be coated with an immediate-release layer. One skilled in the art recognizes still other alternative means of incorporating the immediate release side-effect-reducing compound into the unit dose. Therefore, in one embodiment, by including an effective amount of an antiemetic agent or antihistamine (and optionally including a stimulant) in the unit dose, the subject is prepared for the eventual and subsequent release of one or more opioid analgesic in the controlled-release layer, where the antiemetic agent or antihistamine reduces the incidence of or intensity of adverse effects associated with an opioid agent including but not limited to nausea, vomiting, other gastric upsets, skin rashes, allergic reactions such as swelling, difficulty breathing, closing of throat, abdominal pain, unusual bleeding or bruising, skin rashes, sedation, CNS depression, or respiratory depression in subjects can be significantly reduced.

The immediate-release or controlled-release dosage forms described herein can also take the form of a bi-layered tablet, which can comprise an immediate-release layer and a controlled-release layer. In one embodiment the immediate release layer comprises an antiemetic agent or antihistamine, and optionally a stimulant or a non-opioid analgesic, or both. In one embodiment, the first layer can comprise one, two, three or more active agents. The controlled release layer can comprise an opioid analgesic or non-opioid analgesic or stimulant. Such classes of active agents are described herein above.

The immediate-release or controlled release dosage forms described herein can also take the form of pharmaceutical particles manufactured by a variety of methods, including but not limited to high-pressure homogenization, wet or dry ball milling, or small particle precipitation (nano spray). Other methods to make a suitable powder formulation are the preparation of a solution of active ingredients and excipients, followed by precipitation, filtration, and pulverization, or followed by removal of the solvent by freeze-drying, followed by pulverization of the powder to the desired particle size.

In one embodiment the particles have a final size of 3-1000 µm, such as at most 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 µm. In another embodiment the pharmaceutical particles have a final size of 10-500 µm. In one embodiment the pharmaceutical particles have a final size of 50-600 µm. In another embodiment the pharmaceutical particles have a final size of 100-800 µm. These dosage forms can include immediate-release particles in combination with controlled-release particles in a ratio sufficient useful for delivering the desired dosages of active agents. In an alternative embodiment, a dosage unit can be divided into or exclusively included into both immediate release and controlled release particles.

In a further embodiment the dosage form can be an effervescent dosage form. Effervescent means that the dosage form, when mixed with liquid, including water and saliva, evolves a gas. Some effervescent agents (or effervescent couple) evolve gas by means of a chemical reaction which takes place upon exposure of the effervescent disintegration agent to water and/or to saliva in the mouth. This reaction can be the result of the reaction of a soluble acid source and an alkali monocarbonate or carbonate source. The reaction of these two general compounds produces carbon dioxide gas upon contact with water or saliva. An effervescent couple (or the individual acid and base separately) can be coated with a solvent protective or enteric coating to prevent premature reaction. Such a couple can also be mixed with previously lyophilized particles (such as one or more pharmaceutically active agents coated with a solvent protective or enteric coating. The acid sources may be any which are safe for human consumption and may generally include food acids, acid and hydrite antacids such as, for example: citric, tartaric, amalic, fumeric, adipic, and succinics. Carbonate sources include dry solid carbonate and bicarbonate salt such as, for example, sodium bicarbonate, sodium carbonate, potassium bicarbonate and potassium carbonate, magnesium carbonate and the like. Reactants which evolve oxygen or other gasses and which are safe for human consumption are also included. In one embodiment citric acid and sodium bicarbonate is used.

In another embodiment the dosage form can be in a candy form (e.g., matrix), such as a lollipop or lozenge. In one embodiment one or more pharmaceutically active agents is dispersed within a candy matrix. In one embodiment the candy matrix comprises one or more sugars (such as dextrose or sucrose). In another embodiment the candy matrix is a sugar-free matrix. The choice of a particular candy matrix is subject to wide variation. Conventional sweeteners such as sucrose may be utilized, or sugar alcohols suitable for use with diabetic patients, such as sorbitol or mannitol might be employed. Other sweeteners, such as the aspartanes, can also be easily incorporated into a composition in accordance with compositions described herein. The candy base may be very soft and fast dissolving, or may be hard and slower dissolving. Various forms will have advantages in different situations.

A containing candy mass comprising at least one pharmaceutically active agent can be orally administered to a subject in need thereof so that the agent will be released into the subject's mouth as the candy mass dissolves. The drug rapidly enters the subject bloodstream, and importantly, the blood in the veins draining from the mouth and the pharyngeal and esophageal areas passes through a substantial portion of the body (so that the drug can be absorbed) before the blood passes through the liver (where the drug may be inactivated). A subject in need thereof can include a human adult or child in pain, such as a child in sickle cell crisis, a child undergoing bone marrow transplant or a lumbar puncture procedure, a child with cancer (e.g., metastasic cancer, leukemia or lymphoma).

In some embodiments of the invention the candy matrix (lollipop or lozenge) comprises a composition that lacks a stimulant. In one embodiment said formulation may have a sedative effect in addition to providing pain relief to a subject in need thereof. In some other embodiments the candy matrix (lollipop or lozenge) comprises a composition that comprises a stimulant. In these embodiments the composition provides an anti-sedative effect in addition to providing pain relief to a subject in need thereof.

In one embodiment a candy mass is prepared that comprises one or more layers which may comprise different pharmaceutically active agents and or rates of dissolution. In one embodiment a multilayer candy mass (such as a lollipop) comprises an outer layer with a concentration of one or more pharmaceutically active agents differing from that of one or more inner layers. Such a drug delivery system has a variety of applications. By way of example, it may be desirable to quickly get a predetermined dose of a first pharmaceutically active agent into the bloodstream to obtain a desired effect and then use a different inner layer to deliver one or more other agents.

The choices of matrix and the concentration of the drug in the matrix can be important factors with respect to the rate of drug uptake. A matrix that dissolves quickly can deliver drug into the patient's mouth for absorption more quickly than a matrix that is slow to dissolve. Similarly, a candy matrix that contains one or more pharmaceutically active agents in a high concentration can release more of the one or more pharmaceutically active agents in a given period of time than a candy having a low concentration. In one embodiment a candy matrix such as one disclosed in U.S. Pat. No. 4,671,953 or US Application 2004/0213828 (which are herein incorporated by reference in their entirety) is used to deliver the pharmaceutically active agents disclosed herein.

The immediate-release or extended release dosage forms described herein can also take the form of pharmaceutical particles manufactured by a variety of methods, including but not limited to high-pressure homogenization, wet or dry ball milling, or small particle precipitation (e.g., nGimat's NanoSpray). Other methods useful to make a suitable powder formulation are the preparation of a solution of active ingredients and excipients, followed by precipitation, filtration, and pulverization, or followed by removal of the solvent by freeze-drying, followed by pulverization of the powder to the desired particle size. In one embodiment the pharmaceutical particles have a final size of 3-1000 µm, such as at most 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 µm. In another embodiment the pharmaceutical particles have a final size of 10-500 µm. In another embodiment the pharmaceutical particles have a final size of 50-600 µm. In another embodiment the pharmaceutical particles have a final size of 100-800 µm. These dosage forms can include immediate-release particles in combination with controlled-release particles in a ratio sufficient useful for delivering the desired dosages of active agents. For example, the immediate-release particles can comprise about 12.5 mg of promethazine or a salt thereof, and the controlled-release particles can comprise about 7.5 mg of hydrocodone or oxycodone or a salt thereof, and about 325 mg of acetaminophen or a salt thereof.

In another embodiment, the agents are released from a multi-layered tablet that comprises at least a first layer, a second layer and a third layer. Wherein, the layers containing a pharmaceutically active agent can be optionally separated by one or more layers of inert materials. In one embodiment the layers containing a pharmaceutically active agent have similar rates of release, e.g., all are immediate release or all are controlled-release. In an alternative embodiment the layers have different rates of release. In this embodiment at least one layer is an immediate release layer and at least one layer is a controlled release layer. For example in one embodiment the multilayer tablet comprises at least three layers, each of which contains a different agent, such as: layer one contains promethazine or a salt thereof; layer two comprises hydrocodone or oxycodone or a salt thereof; and layer three comprises acetaminophen or a salt thereof. In this embodiment the promethazine layer may be immediate-release, while the other two layers may be controlled-release.

Transdermal Dosage Forms

In another embodiment, the invention relates to a method of use and a system for the transdermal delivery of one or more pharmaceutically active agents into a subject. In one embodiment a portion of the skin of a subject is sealed with a thin, film layer of a base material to occlude the skin and transport a desired dosage of at least one pharmaceutically active agent across the a layer, which can be from a rate-controlling system in contact with the thin layer. The rate-controlling system can be a thin rate-controlling membrane interposed between one or more agents and the thin layer. In another embodiment a reservoir delivers at least one pharmaceutically active agent to the layer for delivery into a subject. In some embodiments the pharmaceutically active agents to be delivered are: an opioid analgesic, a non-opioid analgesic and an antihistamine; or pharmaceutically acceptable salts, solvates, or prodrugs thereof; one or more pharmaceutically acceptable excipients or carriers.

In one embodiment, the rate-controlling system or reservoir comprises at least one pharmaceutically active agent to be delivered, is dispersed in a base material and contained within a container system. In one embodiment at least one pharmaceutically active agent is dissolved in the base material. In another embodiment at least one pharmaceutically active agent is uniformly dispersed in the base material. In another embodiment, the rate-controlling system or reservoir comprises microparticles of at least one pharmaceutically active agent to be delivered suspended in a base material and contained within a container system. In one embodiment the base material is a viscous material. The container system may comprise a macroporous, non-rate-controlling face membrane with an impervious backing to form a pool or patch-like system of desired face membrane area with the face of the membrane placed over and in contact with the thin, occluding, viscous layer on the skin. The thin viscous layer may be coated or placed on the skin repeatedly, and the patch system placed on top of the thin, viscous layer or the viscous layer formed in situ by exudation through the membrane face when the patch or pool system is placed in position on the skin. In one embodiment the patch or pool container system generally is retained in a transdermal position by the use of a peripheral adhesive layer about the patch or pool. In one embodiment, the face or transport area of the membrane is covered prior to use by a removable cover such as a peelable strip of impervious sheet material. In another embodiment, microcapsules containing a drug for delivery may be suspended in a viscous base material, and the composition then spread as a layer over the skin of the user with or without a covering material.

In other embodiments U.S. Pat. Nos. 4,906,463; 4,588,580; 4,685,911, 4,626,539, 4,834,978 and 5,635,204 disclose useful transdermal patches which may be used for the practice methods and compositions described herein, which are herein incorporated by reference in their entirety.

In one embodiment the compositions are administered to a subject via a transdermal patch.

Suppository Dosage Form

In another embodiment, the compositions are in the form of a suppository. In one embodiment the suppository is useful for vaginal or rectal administration. In some embodiments the suppository is effervescent.

In some embodiments the suppository base material contains hydrophobic or hydrophilic media, each of which can melt at body temperature. In one embodiment the suppository base material used can be cocoa butter or similar material. In another embodiment the suppository base material can be a moist polymer is then mixed with the one or more pharmaceutically active agents and compressed into the desired form. In one embodiment at least one pharmaceutically active agent is dissolved in the suppository base material. In another embodiment at least one pharmaceutically active agent is uniformly dispersed in the suppository base material. In another embodiment, the suppository base material comprises microparticles of at least one pharmaceutically active agent to be delivered suspended in the suppository base material. In some embodiments (such as vaginal suppositories) the suppository is effervescent. In some embodiments the effervescing properties are imparted for the purpose of enhancing the rapid disintegration properties of the suppository.

In other embodiments U.S. Pat. Nos. 4,265,875 and 4,853,211 disclose useful suppositories which may be used for the practice of methods and compositions described herein, which are herein incorporated by reference in their entirety.

Abuse Safeguard Dosage Forms

Adverse-Effect Agents

In one embodiment, the present compositions can safeguard against abuse of the opioid analgesic agent. For example, a composition disclosed herein can further comprise an effective amount of an adverse-effect agent or antagonist agent that reduces or eliminates one or more of: (1) the capacity of the opioid analgesic agent to produce the kind of physical dependence in which withdrawal causes sufficient distress to bring about drug-seeking behavior; (2) the ability to suppress withdrawal symptoms caused by withdrawal from the opioid analgesic agent; and (3) the induction of euphoria. Useful adverse-effect agents include, but are not limited to, opioid antagonists. When there is a potential for an overdose, then an antidote of the opioid analgesic agent can be used as the adverse-effect agent.

The phrase "adverse-effect agent" is also meant to encompass all pharmaceutically acceptable salts of the adverse-effect agent.

Opioid antagonists that can be used as an adverse-effect agent include, but are not limited to, naloxone, naltrexone, nalmefene, cyclazacine, levallorphan, or a salt thereof, and mixtures thereof. In certain embodiments, the opioid antagonist is naloxone, naltrexone or a pharmaceutically acceptable salt thereof.

In some embodiments, the opioid agent and the opioid antagonist are present in a ratio of opioid antagonist to opioid agent (analgesic) which is analgesically effective when the combination is administered orally, but which is aversive in a physically dependent subject. In this manner, the combination product (antagonist/agonist) could in essence be therapeutic to one population (patients in pain), while being unacceptable (aversive) in a different population (e.g., physically dependent subjects) when orally administered at the same dose or at a higher dose than the usually prescribed dosage, e.g., about 2-3 times the usually prescribed dose of the opioid. Thus, the oral dosage form would have less potential for parenteral as well as oral abuse. In one embodiment where the opioid is hydrocodone or oxycodone or a salt thereof and the antagonist is naltrexone or a salt thereof, the ratio of naltrexone or a salt thereof to hydrocodone or a salt thereof is from about 0.02-0.35:1 by weight, and in some embodiments from about 0.05-0.2:1 by weight. In one embodiment the ratio of naltrexone or a salt thereof is in an amount from about 0.5 to about 4 mg per 15 mg of hydrocodone or a salt thereof. In another embodiment the ratio of naltrexone or a salt thereof is in an amount from about 0.75 mg to about 3 mg per 15 mg hydrocodone or a salt thereof. In another example where the opioid antagonist is naltrexone or a salt thereof and the opioid agent is hydromorphone or a salt thereof, the ratio of naltrexone or a salt thereof to hydromorphone or a salt thereof can be from about 0.14:1 to about 1.19:1, or from about 0.222:1 to about 0.889:1. In another example where the opioid antagonist is naltrexone or a salt thereof and the opioid agent is oxycodone or a salt thereof, the ratio of naltrexone or a salt thereof to oxycodone or a salt thereof is about 0.03:1 to about 0.3:1, or from about 0.056:1 to about 0.222:1.

In one embodiment, the opioid is hydrocodone, hydromorphone, oxycodone, fentanyl, or a pharmaceutically acceptable salt thereof.

In some embodiments, an opioid antagonist is administered in an amount (i) which does not cause a reduction in the level of analgesia elicited from the dosage form upon oral administration to a non-therapeutic level and (ii) which provides at least a mildly negative, "aversive" experience in physically dependent subjects (e.g., precipitated abstinence syndrome) when the subjects attempt to take at least twice the usually prescribed dose at a time (and often 2-3 times that dose or more), as compared to a comparable dose of the opioid without the opioid antagonist present. In certain embodiments, an amount of naltrexone or a salt thereof is included in the oral dosage form and is less positively reinforcing (e.g., less "liked") to a non-physically dependent opioid addict than a comparable oral dosage form without the antagonist included. In one embodiment the composition provides effective analgesia when orally administered.

In some embodiments the oral dosage form can be administered on a twice-a-day or a once-a-day basis.

The composition can be formulated as a controlled oral formulation in any suitable tablet, coated tablet or multiparticulate formulation known to those skilled in the art. The controlled release dosage form can optionally include a carrier which is incorporated into a matrix or can be applied as a controlled release coating.

In embodiments in which the opioid analgesic is hydrocodone (or a pharmaceutically acceptable salt thereof), the extended release oral dosage forms may include analgesic doses from about 4 mg to about 60 mg of hydrocodone or a salt thereof per dosage unit. In a controlled release oral dosage forms where hydromorphone or a salt thereof is the therapeutically active opioid, it can be included in an amount from about 2 mg to about 64 mg hydromorphone hydrochloride. In yet another embodiment, the opioid analgesic is oxycodone and the controlled release oral dosage forms include from about 2.5 mg to about 800 mg oxycodone HCL. Alternatively, the dosage form may contain molar equivalent amounts of other salts of the opioids useful in compositions described herein.

In other embodiments U.S. Pat. Nos. 6,228,863; 6,475, 494; 7,201,920; and 7,172,767, 7,201,920 disclose useful opioid agent/opioid antagonist formulations which can be used for the methods and compositions described herein, which are herein incorporated by reference in their entirety.

In another embodiment, one or more non-opioid analgesic agents, in addition to the opioid antagonist, can be included in the dosage form. Such non-opioid drugs can provide additional analgesia, and include, for example, aspirin; acetaminophen; non-steroidal anti-inflammatory drugs ("NSAIDS"), e.g., ibuprofen, naproxen, ketoprofen, etc.; N-methyl-D-aspartate (NMDA) receptor antagonists, e.g., a morphinan such as dextromethorphan or dextrorphan, or ketamine; cycooxygenase-II inhibitors ("COX-II inhibitors"); and/or glycine receptor antagonists.

Abuse Deterrent Agents

In another embodiment the compositions comprising an opioid analgesic safeguards against abuse by further comprising one or more abuse deterrent agents. The choice of which abuse deterrent agent to include in a composition can be varied depending on the route of administration and intended method of treatment. For example different abuse deterrent agents can be used in conjunction with same pharmaceutically active agents depending on if they are formulated as an oral dosage form or a transdermal dosage form. Similarly, compositions intended to treat a cancer associated pain in a subject can comprise a different abuse deterrent agent than a composition intended to treat headache associated pain in a subject.

In one embodiment the abuse deterrent agent is formulated as a gel-forming agent, and optionally comprises one or more mucous membrane irritants or nasal passageway tissue irritants. In another embodiment, the compositions described herein include a composition comprising an analgesic, one or more gel-forming agents and one or more emetics as described herein. In another embodiment, the compositions comprise an opioid analgesic, one or more mucous membrane irritants or nasal passageway tissue irritants and one or more emetics as described herein. In one particular embodiment, the compositions comprise an analgesic, one or more gel-forming agents, one or more mucous membrane irritants and/or nasal passageway tissue irritants, and one or more emetics.

Suitable gel-forming agents include compounds that, upon contact with a solvent (e.g., water), absorb the solvent and swell, thereby forming a viscous or semi-viscous substance that significantly reduces and/or minimizes the amount of free solvent which can contain an amount of solublized drug, and which can be drawn into a syringe. The gel can also reduce the overall amount of drug extractable with the solvent by entrapping the drug in a gel matrix. In one embodiment, typical gel-forming agents include pharmaceutically acceptable polymers, typically hydrophilic polymers, such as hydrogels.

In some embodiments, the polymers exhibit a high degree of viscosity upon contact with a suitable solvent. The high viscosity can enhance the formation of highly viscous gels when attempts are made by an abuser to crush and dissolve the contents of a dosage form in an aqueous vehicle and inject it intravenously.

More specifically, in certain embodiments the polymeric material described herein provides viscosity to the dosage form when it is tampered. In such embodiments, when an abuser crushes and dissolves the dosage form in a solvent (e.g., water or saline), a viscous or semi-viscous gel is formed. The increase in the viscosity of the solution discourages the abuser from injecting the gel intravenously or intramuscularly by preventing the abuser from transferring sufficient amounts of the solution to a syringe to cause a desired "high" once injected.

Suitable polymers include one or more pharmaceutically acceptable polymers selected from any pharmaceutical polymer that will undergo an increase in viscosity upon contact with a solvent. Polymers can include polyethylene oxide, polyvinyl alcohol, hydroxypropyl methyl cellulose and carbomers.

In another embodiment the compositions comprise an abuse deterrent agent that is a mucous membrane irritant or nasal passageway tissue irritant, or both. These irritants are designed to deter abuse via the improper administration of a dosage form comprising an opioid (e.g., crushing and snorting). In one embodiment, suitable mucous membrane irritants or nasal passageway tissue irritants include compounds that are generally considered pharmaceutically inert, yet can induce irritation. Such compounds include, but are not limited to surfactants. In one embodiment, suitable surfactants include sodium lauryl sulfate, poloxamer, sorbitan monoesters and glyceryl monooleates. Other suitable compounds are believed to be within the knowledge of a practitioner skilled in the relevant art, and can be found in the Handbook of Pharmaceutical Excipients, 4th Ed. (2003), the entire content of which is hereby incorporated by reference.

In one embodiment the irritant can be present in amount of from 1 to 10 percent by weight on a solid basis, such as from about 1 to 5 percent by weight on a solid basis. In another embodiment, the amount of irritant can be present in an amount from 1 to 3 percent by weight.

In another embodiment, the irritant can deter abuse of a dosage form when a potential abuser tampers with a dosage form described herein. Specifically, in such embodiments, when an abuser crushes the dosage form, the irritant is exposed. The irritant discourages inhalation of the crushed dosage form by inducing pain and/or irritation of the abuser's mucous membrane and/or nasal passageway tissue. In one embodiment, the irritant discourages inhalation (e.g., via snorting through the nose) by inducing pain and/or irritation of the abuser's nasal passageway tissue.

In one embodiment, the compositions described herein comprise one or more mucous membrane irritants that cause irritation of mucous membranes located anywhere on or in the body, including membranes of the mouth, eyes and intestinal tract. Such compositions can deter abuse via oral, intra-ocular or rectal or vaginal routes.

In another embodiment the compositions comprise an abuse deterrent agent that is an emetic or emesis inducing agent. In one embodiment the emetic can be a pharmaceutically acceptable inert excipient that only induces emesis after a certain threshold amount is ingested. In another embodiment, the emetic can be a pharmaceutically active emetic.

In one embodiment, the amount of emetic present in the compositions described herein can be tied directly to the amount of drug in the composition. Thus, by controlling the quantity of the emetic compound in the composition, emesis can be avoided if normal prescription directions are followed. However, if an overdosage occurs by ingesting more than a prescribed quantity of a drug in a composition described herein, the amount of ingested emetic can exceed the threshold amount necessary to induce emesis.

In some embodiments, the threshold amount of emetic for inducing emesis can be reached when the normal prescription directions are inappropriately increased by factors of 2, 3, 4, 5, 6, 7, or 8 times, or more. Thus, in some embodiments, the amount of emetic present in a composition described herein is an amount such that the amount of emetic ingested does not exceed the threshold amount necessary for inducing emesis until a subject ingests 2, 3, 4, 5, 6, 7, or 8 or more times the amount of drug normally prescribed. In some embodiments, emesis can preclude death or serious illness in the subject.

In one embodiment, the emetic is zinc sulfate. Zinc sulfate is an excipient, which can induce emesis when more than about 0.6 to 2.0 gm is ingested, typically more than about 0.6 gm, or about 5 to 25 percent by weight on a solid basis, more typically about 5 to 10 percent by weight. Accordingly, compositions described herein can be easily designed to induce emesis if a prescribed dosage is exceeded and/or if prescription directions are not followed for dosage forms containing a composition described herein. Typically, suitable embodiments include less than about 0.6 to 2.0 gm of zinc sulfate.

For example a dosage form can induce emesis only after a pre-determined number of dosage forms are ingested (such as 4, 5, 6 or more), in this case the amount of zinc sulfate in each dosage form should not exceed about 0.19 gm. Thus, if three dosage forms are ingested, the amount of emetic can be 0.57 gm, which is less than a typical threshold amount of the particular emetic. However, if a fourth dosage form having 0.19 gm. of zinc sulfate is ingested, the amount of emetic exceeds the threshold amount, and emesis is induced.

In another embodiment the compositions comprise an effective amount of an abuse deterrent agent that induces flushing, (i.e. redness of the skin, including redness of the skin of one or more of the face, neck, chest, back and trunk and legs) and/or itching and/or discomfort and/or temporary pain (a flushing/pain inducing agent or flushing inducing agent), and/or generalized pruritic, and/or intense warmth, and/or chills when administered at or in excess of a threshold amount.

With respect to flushing, discomfort and pain inducing agents, a threshold amount is an amount below which one or more adverse effects is absent or below which a subject may experience a beneficial effect.

In one embodiment, the flushing agent or itching agent or pain-inducing agent is a drug. In certain embodiments, the drug is obtainable "over the counter" and in certain embodiments, the "over the counter" drug is a vitamin. In yet another embodiment, the vitamin is niacin. In another embodiment, the present invention includes vitamin.

Accordingly, in one embodiment the amount of flushing, itching, or pain inducing agent present in a composition described herein can be tied directly to the amount of drug in the composition. Thus, by controlling the quantity of the flushing, itching, or pain inducing agent in the composition, flushing, itching, or pain can be avoided if normal prescription directions are followed. However, if an overdosage occurs by ingesting more than a prescribed quantity of a drug in a composition described herein (e.g., by ingesting more than the prescribed dose), the total amount of flushing, itching, or pain inducing agent can, in certain embodiments, exceed the threshold amount necessary to induce flushing, itching, or pain thereby inducing flushing, itching, or pain.

In one embodiment, compositions and methods described herein includes about 10 mg to about 500 mg of the flushing, itching, or pain inducing agent. In yet another embodiment, a composition comprises about 15 mg to about 150 mg of a flushing, itching, or pain agent. In another embodiment, a composition comprises 15, 30, 45, 60, 75, 90 or 105 mg of a flushing, itching, or pain inducing agent. In one embodiment, compositions and methods described herein includes a flushing, itching, or pain inducing agent in an amount of about 1% to 25%, typically about 3% to 15%, more typically about 1%, 3%, 6%, 9%, 12%, 15% or 20% by weight, including or excluding the weight of any analgesic and/or other drug susceptible to abuse.

In some embodiments of dosage forms having a controlled release layer or formulation, the amount of flushing inducing agent (and in other embodiments, the amount of any abuse deterrent component or opioid antagonist described herein), can exceed the threshold amount present in an immediate release form. This is because in controlled release formulations, the amount of drug which is susceptible to abuse is typically higher than in an immediate release formulation and the flushing inducing agent (or other abuse deterrent component) becomes bioavailable at a slower rate than the immediate release form. Thus, the amount of abuse deterrent component which is bioavailble typically also remains below the amount sufficient to cause an abuse deterrent effect. However, if the dosage form is tampered with (e.g., ground, chewed or crushed), a large portion of the abuse deterrent component becomes immediately bioavailable, thus inducing one or more abuse deterrent effects.

Examples of abuse deterrent agents that can be used in compositions described herein are disclosed in US Patent Application Nos: US20060177380A1; US20060110327A1; and US20070231268A1, which are herein incorporated by reference in its entirety.

Abuse Deterrence via Chemical Modification of Active Agents

In another embodiment the compositions comprise an opioid agent that is conjugated to a chemical moiety. The chemical moiety can be any chemical substance that can be attached to the opioid agent in a manner that renders it pharmacologically inactive. Analgesics and stimulants produce their pharmacological effects through binding to specific receptors or uptake proteins. The attachment of certain chemical moieties can therefore prevent the active substance from binding its receptor(s) or recognition site on its uptake protein. Further, without being bound by theory, the covalent modification is believed to prevent the pharmacological effect by preventing the drug from crossing the blood-brain barrier. The attachment of the chemical moiety to the opioid agent can also prevent or substantially delay the absorption of the compound, particularly when the compound is delivered by routes other than oral administration.

In one embodiment of the invention, the chemical moiety is attached to the opioid agent in a manner in which it is not readily released by conditions found in the mouth (saliva), the intranasal cavity, the surface of the lungs, or in the serum. Extreme acid conditions encountered in the stomach are not present elsewhere in humans. Therefore, any acid dependent release mechanism will occur only after oral administration. Although, degradative enzymes are present in the aforementioned environments, they are not generally present in the high concentrations found in the intestinal tract. Thus, release of the opioid agent by enzymatic cleavage will not occur rapidly when the novel compounds are administered by routes other than oral delivery.

In another embodiment of the invention, the opioid agent is attached to a polymer of serine (or other amino acid containing a hydroxyl side chain e.g. threonine, tyrosine) via side chain hydroxyl groups. Alternatively, attachment is to a polymer of glutamic acid through the carboxyl group of the delta carbon of glutamic acid. The resulting ester (carbonate) linkages can be hydrolysed by lipases (esterases) encountered in the small intestine. Esterases are not present at high levels in saliva or on the mucosal surfaces of the nasal cavity, lungs, or oral cavity. Thus, opioid agents attached to polyglutamic acid by this method would not be rapidly released by saliva or when delivered intranasally or by inhalation.

In another embodiment of the invention, the opioid agent is attached to an oligopeptide, which can consist of between one and five amino acids. In a further embodiment of the invention the amino acids are a heterogenous mixture of the twenty naturally occurring amino acids. Hydrophilic amino acids will tend to prevent passive absorption of the analgesic peptide conjugate through nasal membranes. In one embodiment of the invention that hydrophilic amino acids be included in the oligopeptide. In another embodiment of the invention that lipophilic amino acids be attached closer to the analgesic for optimum stability. Both lipophilic and hydrophilic properties (i.e., amphiphilic) can be satisfied with between three and five amino acids. In a further embodiment of the invention, the oligopeptide that is attached to the analgesic can be an amphiphilic tripeptide.

Amphiphilic amino acids/oligopeptides may contain (i) hydrophobic amino acids, located in positions next to the active agent to provide increased stability; (ii) amino acid sequences designed to be cleaved by intestinal enzymes (e.g. pepsin, trypsin, chymotrypsin, elastase, carboxypeptidases A and B, etc.) provide for increased bioavailability; (iii) peptides longer than three amino acids for increased stability, increased anti-abuse e.g. less membrane permeability, and potentially more efficient intestinal digestion, e.g., major intestinal enzymes target proteins and polypeptides, (iv) or mixtures thereof. In one embodiment the carrier portion of the conjugate is designed for intestinal cleavage.

In another embodiment the cleavage specificity is directed to pepsin and/or chymotrypsin. Examples of carriers include XXXAA or XXAAA, where X is selected from any amino acid, except Arg, Lys, His, Pro, and Met and A is selected from Tyr, Phe, Trp, or Leu. Examples of other carriers are selected from XXXPheLeu wherein X is Glu; XXXPheLeu wherein X is Gly; XXPheLeuLeu wherein X is Glu; and XXPheLeuLeu wherein X is Gly.

In another embodiment the cleavage specificity is directed to trypsin. Examples of more carriers include XXXAA or XXAAA wherein X is any amino acid except Pro and Cys and A is Arg or Lys. Examples of yet more carriers are selected from XXXArgLeu wherein X is Glu; XXXArgLeu wherein X is Gly; XXArgLeuLeu wherein X is Gly; XXXArgLeuLeu wherein X is Gly.

Examples of chemical modifications to opioid agents that can be used in compositions described herein are disclosed in US Patent Application No: 20050080012, which is herein incorporated by reference in its entirety.

In another embodiment, one or more adverse-effect-reducing active agents in addition to the opioid antagonist agent or abuse deterrent component can be included in the dosage form. Adverse-effect-reducing active agents include but are not limited to promethazine, dolasetron, granisetron, ondansetron, tropisetron, palonosetron, domperidone, droperidol, haloperidol, chlorpromazine, prochloperazine, metoclopramide, alizapride, cyclizine, diphenhydramine, dimenhydrinate, meclizine, hydroxyzine, *cannabis*, dronabinol, nabilone, midazolam, lorazepam, hyoscine, dexamethasone, trimethobenzamide, emetrol and propofol.

Additives

The present compositions can further comprise suitable additives, including, but not limited to, diluents, binders, surfactants, lubricants, glidants, coating materials, plasticizers, coloring agents, flavoring agents, or pharmaceutically inert materials. Examples of diluents include, for example, cellulose; cellulose derivatives such as microcrystalline cellulose and the like; starch; starch derivatives such as corn starch, cyclodextrin and the like; sugar; sugar alcohol such as lactose, D-mannitol and the like; inorganic diluents such as dried aluminum hydroxide gel, precipitated calcium carbonate, magnesium aluminometasilicate, dibasic calcium phosphate and the like.

Examples of binders include, for example, hydroxypropylcellulose, methylcellulose, hydroxypropylmethylcellulose, povidone, dextrin, pullulane, hydroxypropyl starch, polyvinyl alcohol, scacia, agar, gelatin, tragacanth, macrogol and the like.

Examples of surfactants include, for example, sucrose esters of fatty acids, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, lauromacrogol and the like.

Examples of lubricants include, for example, stearic acid, calcium stearate, magnesium stearate, talc and the like.

Examples of glidants include, for example, dried aluminum hydroxide gel, magnesium silicate and the like.

Examples of coating materials include, for example, hydroxypropylmethyl cellulose 2910, aminoalkyl methacrylate copolymer E, polyvinylacetal diethylaminoacetate, macrogol 6000, titanium oxide and the like. Examples of plasticizers include, for example, triethyl citrate, triacetin, macrogol 6000 and the like.

Administration

Described herein are methods for preventing an adverse effect such as nausea, vomiting, other gastric upsets, skin rashes, itching, allergic reactions such as swelling, difficulty breathing, closing of throat, abdominal pain, unusual bleeding or bruising, skin rashes, sedation, CNS depression, or respiratory depression in a subject receiving, or in need of, opioid analgesic therapy. The prevention of an adverse effect can be accomplished by the administration of an effective amount of promethazine or other antihistamine with the chosen analgesic agent or agents. In one embodiment, the invention provides methods for treating pain, comprising administering to a subject in need thereof an effective amount of an opioid analgesic agent, a non-opioid analgesic agent, an agent that reduces side effects of the opioid analgesic agent and optionally a stimulant agent. In one embodiment, the non-opioid analgesic agent is acetaminophen. In another embodiment, the agent that reduces an adverse effect is promethazine. In another embodiment, the invention provides methods for treating pain, comprising administering to a subject in need thereof an effective amount of an opioid analgesic agent, a non-opioid analgesic agent, a barbiturate agent, an agent that reduces side effects of the opioid analgesic agent and optionally a stimulant agent. In another embodiment, the invention provides methods for treating pain, comprising administering to a subject in need thereof an effective amount of an opioid analgesic agent, a barbiturate agent, an agent that reduces side effects of the opioid analgesic agent and optionally a stimulant agent. In another embodiment, the invention provides methods for treating pain, comprising administering to a subject in need thereof an effective amount of an a non-opioid analgesic agent, a barbiturate agent, an agent that reduces side effects of the opioid analgesic agent and optionally a stimulant agent. In another embodiment, the invention provides methods for treating pain, comprising administering to a subject in need thereof an effective amount of an opioid analgesic agent, an agent that reduces side effects of the opioid analgesic agent and optionally a stimulant agent.

The administration can continue for only a relatively short time in the case of an acute condition requiring opioid therapy or for long periods in the case of conditions requiring chronic use of opioid analgesics. The dosing of analgesics can be dependent upon the condition being treated, the subject's individual perception of pain and the use of the opioid on a set time schedule as a prophylactic to prevent the onset of pain or on an as needed basis in response to perceived pain. The choice of selecting a dosage of a composition that contains suitable amount of promethazine can be dependent upon the extent and severity of the adverse effects including nausea, vomiting, other gastric upsets, skin rashes, allergic reactions such as swelling, difficulty breathing, closing of throat, abdominal pain, unusual bleeding or bruising, skin rashes, sedation, CNS depression, or respiratory depression in a subject, upon the sensitivity to side-effect-reducing compounds such as promethazine in a subject, upon the likelihood of subject losing medication by vomiting, and/or on an as needed basis in response to perceived adverse effects. The dosage can be assessed by a prescribing professional evaluating the subject, the condition treated, the analgesic to be used, diet and the expected duration of therapy.

In one embodiment, compositions and methods described herein provides for a method for treating a subject suffering from or susceptible to pain, comprising administering to said subject an effective amount of a composition comprising an effective amount of a first component which is a non-opioid analgesic, or a pharmaceutically acceptable salt thereof, an effective amount of a second component which is a non-opioid analgesic, or a pharmaceutically acceptable salt thereof and an effective amount of a third component which is an antihistamine.

In another embodiment, a method for treating a subject is provided comprising administering an effective amount of a composition comprising: an effective amount of a first pharmaceutically active agent which is an opioid analgesic, or a pharmaceutically acceptable salt thereof; an effective amount of a second pharmaceutically active agent which is a non-opioid analgesic, or a pharmaceutically acceptable salt thereof; and an effective amount of a third pharmaceutically active agent which is an antihistamine or an anti-emetic. In one embodiment the at least one adverse effect is nausea, vomiting, other gastric upsets, skin rashes, allergic reactions such as swelling, difficulty breathing, closing of throat, itching, abdominal pain, unusual bleeding or bruising, skin rashes, sedation, CNS depression, or respiratory depression. In one embodiment the non-opioid analgesic is acetaminophen or analogue thereof. In one embodiment, the antihistamine is promethazine. In one embodiment, the opioid analgesic is hydrocodone. In another embodiment the opioid analgesic is oxycodone. In another embodiment, the invention provides methods for preventing or ameliorating an adverse effect associated with administration of an analgesic, comprising administering to a subject in need thereof an effective amount of an opioid analgesic agent, a non-opioid analgesic agent, an agent that reduces side effects of the opioid analgesic agent and optionally a stimulant agent. In one embodiment, the non-opioid analgesic agent is acetaminophen. In another embodiment, the agent that reduces an adverse effect is promethazine. In another embodiment, the invention provides methods for preventing or ameliorating an adverse effect associated with administration of an analgesic, comprising administering to a subject in need thereof an effective amount of an opioid analgesic agent, a non-opioid analgesic agent, a barbiturate agent, an agent that reduces side effects of the opioid analgesic agent and optionally a stimulant agent. In another embodiment, the invention provides methods for preventing or ameliorating an adverse effect associated with administration of an analgesic, comprising administering to a subject in need thereof an effective amount of an opioid analgesic agent, a barbiturate agent, an agent that reduces side effects of the opioid analgesic agent and optionally a stimulant agent. In another embodiment, the invention provides methods for preventing or ameliorating an adverse effect associated with administration of an analgesic, comprising administering to a subject in need thereof an effective amount of an a non-opioid analgesic agent, a barbiturate agent, an agent that reduces side effects of the opioid analgesic agent and optionally a stimulant agent. In another embodiment, the invention provides methods for preventing or ameliorating an adverse effect associated with administration of an analgesic, comprising administering to a subject in need thereof an effective amount of an opioid analgesic agent, an agent that reduces side effects of the opioid analgesic agent and optionally a stimulant agent.

In another embodiment, compositions and methods described herein provides for a method for preventing an adverse effect such as nausea, vomiting, and a skin rash in a subject receiving or in need of opioid therapy by the administration of an effective amount of acetaminophen or analogue thereof and promethazine with the opioid analgesic agent. In one embodiment, the opioid analgesic is hydrocodone. In another embodiment the opioid analgesic is oxycodone. In one embodiment, administration of a composition comprising a non-opioid analgesic and an antihistamine enhances the reduction or elimination of adverse effects associated with an opioid analgesic. For example, addition of promethazine and acetaminophen/ibuprofen reduces or eliminates an adverse effect associated with an opioid analgesic in a synergistic manner.

It is believed that administration of a composition of the invention would result in treatment of the subject which includes elimination or reduction of an adverse effect associated with analgesics (e.g., opioids) and enhance the beneficial uses of such analgesics. Such an adverse effect can otherwise render administration of certain analgesics intolerable, due to for example vomiting, nausea, and skin rashes. Therefore, various embodiments of the methods of the invention are directed to target populations of subjects that are susceptible to such an adverse effect(s), thus allowing such subjects to benefit from the pain-alleviating effects of analgesic-based pain relief, administration of which would otherwise be intolerable.

For example, by reducing the risk of vomiting, the risk of subject losing the analgesics (and losing the pain-relieving beneficial effects of analgesics) by vomiting is minimized. Furthermore, administration can be adjusted to provide the dose of side-effect-reducing compound to match the subject's analgesic ingestion without separate intervention by the health care professionals. Adding one or more additional active agents, such as promethazine, to the present compositions is believed to result in a composition having reduced potential for abuse and diversion.

Routes of Administration

In various embodiments, the active agents are formulated to be administered through oral dosage forms (e.g., tablets, capsules, gels, lollipops), inhalations, nasal sprays, patches, absorbing gels, liquids, liquid tannates, suppositories, injections, I.V. drips, other delivery methods, or a combination thereof to treat subjects. Administration may be performed in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary (e.g., AERx® inhalable technology commercially available from Aradigm, or Inhance, pulmonary delivery system commercially available from Inhale Therapeutics), vaginally, parenterally, rectally, or intraocularly.

To prepare the present compositions, an effective amount of active agents can be mixed with a suitable pharmaceutically acceptable carrier. Upon mixing of the compounds, the resulting composition can be a solid, a half-solid, a solution, suspension, or an emulsion. Such compositions can be prepared according to methods known to those skilled in the art. The forms of the resulting compositions can depend upon a variety of factors, including the intended mode of administration and the solubility of the compounds in the selected carrier or vehicle. The effective concentration of analgesics is sufficient for lessening or alleviating pain. In one embodiment of the invention, the components of the present compositions are at least one opioid analgesic agent (e.g., hydrocodone/oxycodone), one non-opioid analgesic agent (e.g., acetaminophen), and one antihistamine agent (e.g., promethazine). In other embodiments, administration comprises administration of an antihistamine (e.g., promethazine) separately, prior to, or during administration of the analgesic formulations described herein (e.g., which comprises hydrocodone and acetaminophen). In another embodiment the components of the present compositions are at least one opioid analgesic agent, a non-opioid analgesic agent, an agent that reduces side effects of the opioid analgesic agent and a stimulant agent. In another embodiment, the components of the present compositions are at least one opioid analgesic agent, a non-opioid analgesic agent, a barbiturate agent, an agent that reduces side effects of the opioid analgesic agent and optionally a stimulant agent. In another embodiment, the components of the present compositions are at least one opioid analgesic agent, a barbiturate agent, an agent that reduces side effects of the opioid analgesic agent and optionally a stimulant agent. In another embodiment, the components of the present compositions are at least one non-opioid analgesic agent, a barbiturate agent, an agent that reduces side effects of the opioid analgesic agent and optionally a stimulant agent. In another embodiment, components of the present compositions are at least one opioid analgesic agent, an agent that reduces side effects of the opioid analgesic agent and optionally a stimulant agent.

The agents of the compositions and methods described herein can be administered by the nasal inhalation route using conventional nebulizers or by oxygen aerosolization to provide convenient pain relief with reduced adverse effects. The agents can be suspended or dissolved in a pharmacologically acceptable inhalation carrier. Examples of such carriers are distilled water, water/ethanol mixtures, and physiological saline solution. Conventional additives including sodium chloride, glucose, citric acid and the like may be employed in these dosage forms to stabilize or to provide isotonic media. In one embodiment of the invention, the compositions suitable for nasal inhalation by oxygen aerosolization administration comprise hydrocodone or oxycodone, acetaminophen, and promethazine. In other embodiments, an antihistamine (e.g., promethazine) can be administered separately, prior to, or during administration of the compositions described herein (e.g., those comprising hydrocodone and acetaminophen).

The agents described herein can also be administered as a self-propelled dosage unit in aerosol form suitable for inhalation therapy. Suitable means for employing the aerosol inhalation therapy technique are described, for example, in U.S. Pat. No. 6,913,768 to Couch et al., which is incorporated herein by reference in its entirety. The agent can be suspended in an inert propellant such as a mixture of dichlorodifluoromethane and dichlorotetrafluoroethane, together with a co-solvent such as ethanol, together with flavoring materials and stabilizers. In one embodiment of the invention, the agents useful for a self-propelled dosage unit in aerosol form administration are hydrocodone or oxycodone, acetaminophen, and promethazine. In a further embodiment the dosage unit may further comprise an agent such as a bronchodilator (e.g., albuterol).

The agents of the compositions and methods described herein can also be administered as nasal spray/drop compositions, which can conveniently and safely be applied to subjects to effectively treat pain with reduced adverse effects. The compositions may further comprise a water soluble polymer such as polyvinylpyrrolidone, together with other medications such as sumatriptan, together with bioadhesive material. In one embodiment of the invention, the components of a composition for nasal spray or drop administration are hydrocodone or oxycodone agent, acetaminophen, and promethazine, or a pharmaceutically acceptable salt thereof.

The compositions described herein can also be administered topically to the skin of a subject. The agents can be mixed with a pharmaceutically acceptable carrier or a base which is suitable for topical application to skin to form a dermatological composition. Suitable examples of carrier or base include, but not limited to, water, glycols, alcohols, lotions, creams, gels, emulsions, and sprays. A dermatological composition comprising an analgesic agent can be integrated into a topical dressing, medicated tape, dermal patch absorbing gel and cleansing tissues. In one embodiment of the invention, the dermatological composition comprises hydrocodone or oxycodone, acetaminophen, and promethazine.

The compositions described herein can also be in liquid or liquid tannate form. The liquid formulations can comprise, for example, an agent in water-in-solution and/or suspension form; and a vehicle comprising polyethoxylated castor oil, alcohol and/or a polyoxyethylated sorbitan mono-oleate with or without flavoring. Each dosage form comprises an effective amount of an active agent and can optionally comprise pharmaceutically inert agents, such as conventional excipients, vehicles, fillers, binders, disintegrants, pH adjusting substances, buffer, solvents, solubilizing agents, sweeteners, coloring agents and any other inactive agents that can be included in pharmaceutical dosage forms for oral administration. Examples of such vehicles and additives can be found in Remington's Pharmaceutical Sciences, 17th edition (1985). Therefore, in one embodiment a liquid composition of the invention comprises an opioid analgesic (e.g., hydrocodone or oxycodone), a non-opioid analgesic (e.g., acetaminophen) and an antihistamine (e.g., promethazine). In another embodiment a liquid composition of the invention comprises at least one opioid analgesic agent, a non-opioid analgesic agent, an agent that reduces side effects of the opioid analgesic agent and a stimulant agent. In another embodiment, a liquid composition of the invention comprises at least one opioid analgesic agent, a non-opioid analgesic agent, a barbiturate agent, an agent that reduces side effects of the opioid analgesic agent and optionally a stimulant agent. In another embodiment, a liquid composition of the invention comprises at least one opioid analgesic agent, a barbiturate agent, an agent that reduces side effects of the opioid analgesic agent and optionally a stimulant agent. In another embodiment, a liquid composition of the invention comprises at least one non-opioid analgesic agent, a barbiturate agent, an agent that reduces side effects of the opioid analgesic agent and optionally a stimulant agent. In another embodiment, a liquid composition of the invention comprises at least one opioid analgesic agent, an agent that reduces side effects of the opioid analgesic agent and optionally a stimulant agent.

The compositions described herein can also be administered in a suppository form, comprising an outer layer containing the composition in a suppository base. The suppository base may, for example, be any conventional suppository base material such as glycogelatin, polyethylene glycol, fractionated palm kernel oil, or one or more natural, synthetic or semi synthetic hard fats such as cocoa butter. Therefore, in one embodiment of the invention, the base material is mixed with an opioid analgesic (e.g., hydrocodone/oxycodone), a non-opioid analgesic (e.g., acetaminophen) and an antihistamine (e.g., promethazine).

The compositions described herein can also be administered in injection-ready stable liquids for injection or I.V. drip. For example, saline or other injection-ready liquid can be mixed with an opioid analgesic (e.g., hydrocodone or oxycodone), a non-opioid analgesic (e.g., acetaminophen) and an antihistamine (e.g., promethazine). In one embodiment a composition disclosed herein is administered by a subject administered injection. For example a subject can administer the composition via a hand-held injection device such as a pen type injector. In one example a subject can use a device or component disclosed in U.S. Pat. Nos. 6,146,361; 5,536,249; or 5,954,700 (which are herein incorporated by reference in their entirety) to administer a pharmaceutical composition disclosed herein.

Treatment or Prevention of Pain

The present compositions and methods are useful for treating or preventing pain. Accordingly the present invention includes methods for treating or preventing pain, comprising administering to a subject in need thereof a composition of the invention. Pain treatable or preventable includes, but is not limited to, pain associated with cancer, chronic or acute pain, headache pain, migraine headache, chronic headache, surgical procedure, acute or chronic physical injury, bone fracture or crush injuries, spinal cord injury, inflammatory disease (e.g., pancreatitis), noninflammatory neuropathic or dysfunctional pain conditions, or a combination thereof.

Various methods of drug administration known in the art or disclosed herein are utilized to deliver a composition of present invention to a subject in need thereof.

In some embodiments, methods of treatment or prevention comprising administering a composition of the invention are for treating pain or preventing pain. In some embodiments, the pain treatable or preventable via administration of a composition of the invention includes but is not limited to headache pain, and/or headache related symptoms as further described herein below.

Treatment or Prevention of Headache

The present compositions and methods are useful for treating or preventing a headache. Preventable or treatable headaches include but are not limited to migraine headaches (with or without aura), cluster headaches, chronic headaches, tension type headaches, Hemicrania Continua, new daily persistent, chronic tension type headaches or any combination thereof. In one embodiment, a method for treating or preventing a headache comprises administering to a subject in need thereof a composition of the invention. Each of such compositions if fully described herein.

Migraines and cluster headaches are both important, well-known, and extensively studied medical problem. In many cases, they completely incapacitate a sufferer for the duration of the headache. Their physiological embodiments, causative and aggravating factors, and current Treatments are discussed in detail in numerous scientific articles, and in full-length medical textbooks such as Headache in Clinical Practice (edited by S. Silberstein et al., Oxford Univ. Press, 1998); The Headaches, by J. Olesen; and Headache Disorders: A Management Guide for Practitioners, by A. Rapoport and F. Sheftell (W. B. Saunders, Philadelphia, 1996), which are herein incorporated by reference in their entirety. In addition, various definitions, categories, and diagnostic standards are defined by standardized criteria that have been approved and issued by the International Headache Society (IHS), which were published as a supplement to the journal Cephalalgia (Cephalalgia. 2004; 24 Suppl 1:9-160) and is herein incorporated by reference in its entirety.

In one embodiment a composition of the invention is administered to a subject to treat, eliminate or prevent at least one headache symptom. An effective amount is a dosage sufficient to reduce at least one symptom associate with a headache. Headache symptoms include: (1) frequency, which can be evaluated over a span of time, such as number of such headaches per week, per month, or per year; (2) duration, which evaluates (usually in hours) how long a headache lasts, from the time it begins to develop into a migraine or cluster headache, until it has been resolved; and (3) severity (also referred to as intensity), which is based on subjective estimates of the severity or intensity of pain or other symptoms (such as nausea) being suffered by patients during such headaches. In one embodiment a composition is used in a method to reduce the frequency, duration or severity of a preventable or treatable headache.

Treatment or Prevention of Photophobia

In one embodiment, the invention provides methods for treating or preventing photophobia, comprising administering to a subject in need thereof a composition of the invention. In one embodiment the composition comprises an effective amount of each of an opioid analgesic and an antiemetic, as disclosed herein above. In one embodiment, the antiemetic is promethazine or a pharmaceutically acceptable salt thereof and the opioid analgesic is hydrocodone, oxycodone or a pharmaceutically acceptable salt thereof. In a further embodiment, the composition is in the form of a bilayer tablet that comprises an immediate-release layer and a controlled-release layer. In another embodiment the immediate-release layer comprises promethazine or a pharmaceutically acceptable salt thereof, and the controlled-release layer comprises hydrocodone, oxycodone or a pharmaceutically acceptable salt thereof. In a further embodiment, the photophobia is associated with a migraine headache.

In another embodiment, the invention provides methods for treating or preventing photophobia, comprising administering to a subject in need thereof a composition comprising an effective amount of a triptan and an effective amount of an antiemetic. In a further embodiment the triptan is a sumatriptan or a pharmaceutically acceptable salt thereof, and the antiemetic is promethazine or a pharmaceutically acceptable salt thereof. In one embodiment, the sumatriptan salt is sumatriptan succinate.

In yet a further embodiment, the composition is in the form of a bilayer tablet that comprises an immediate-release layer and a controlled-release layer. In another embodiment of the invention the controlled-release layer comprises sumatriptan or a pharmaceutically acceptable salt thereof, and the immediate-release layer comprises promethazine or a pharmaceutically acceptable salt thereof.

EXAMPLES

Example 1

Example of an Analgesic Composition Comprising Hydrocodone Bitartrate, Acetaminophen and Promethazine Hydrochloride

| Analgesic Composition A Agents mg/Tablet | |
|---|---|
| Hydrocodone Bitartrate | 7.5 mg |
| Acetaminophen | 325 mg |
| Promethazine Hydrochloride | 12.5 mg |

Example 2

In one example, the composition of Example 1 is formulated in the form of a bi-layer tablet having an immediate-release layer comprising 12.5 mg of promethazine hydrochloride and having a controlled-release layer comprising 7.5 mg of hydrocodone bitartrate and 325 mg of acetaminophen.

Example 3

The composition of Example 1 is orally administered with water to a subject having a tendency to exhibit adverse effects of opioid administration, such as gastric upset, nausea, vomiting, skin rash, sedation, CNS depression, or respiratory depression. Such subjects, upon taking the composition set forth in Example 1 will receive an effective amount of promethazine in their blood stream. The promethazine will reduce the adverse effects that such a target population would otherwise exhibit.

Example 4

Example of an analgesic composition comprising Oxycodone Hydrochloride, Acetaminophen and Promethazine Hydrochloride

| Analgesic Composition B Agents mg/Tablet | |
|---|---|
| Oxycodone HCl | 5 mg or 7.5 mg |
| Acetaminophen | 325 mg |
| Promethazine Hydrochloride | 12.5 mg |

Example 5

In one example, the composition of Example 4 is in the form of a bi-layer tablet having an immediate-release layer comprising 12.5 mg of promethazine hydrochloride, and having a controlled-release layer comprising 5 or 7.5 mg of oxycodone HCl and 325 mg of acetaminophen.

Example 6

The composition of Example 5 is orally administered with water to a subject having a tendency to exhibit adverse effects of opioid administration, such as gastric upset, nausea, vomiting, skin rash, sedation, CNS depression, or respiratory depression. Such subjects, upon taking the composition set forth in Example 5 will receive an effective amount of promethazine which will reduce the adverse effects that such a target population would otherwise exhibit.

Example 7

Example of an Abuse Safeguard Drug Formulation Comprising Hydrocodone Bitartrate, Acetaminophen and Promethazine Hydrochloride.

| Analgesic Composition C Agents mg/Tablet | |
|---|---|
| Hydrocodone Bitartrate | 7.5 mg |
| Acetaminophen | 325 mg |
| Promethazine HCl | 12.5 mg |
| Naltrexone | 0.75 mg |

Example 8

In one example, the composition of Example 7 is in the form of a bi-layered tablet having an immediate-release layer comprising 12.5 mg of promethazine hydrochloride, and having a controlled-release layer comprising 7.5 mg of hydrocodone bitartrate and 325 mg of acetaminophen.

Example 9

The composition of Example 7 is orally administered with water to a subject having a tendency to exhibit adverse effects of opioid administration, such as gastric upset, nausea, vomiting, skin rash, sedation, CNS depression, or respiratory depression. Such subjects, upon taking the composition set forth in Example 7 will receive an effective amount of promethazine in their blood stream. The promethazine will reduce the adverse effects that such a target population would otherwise exhibit.

Example 10

Example of an Abuse Safeguard Drug Formulation Comprising Oxycodone HCl, Acetaminophen and Promethazine HCl.

| Analgesic Composition D Agents mg/Tablet | |
|---|---|
| Oxycodone HCl | 5 mg or 7.5 mg |
| Acetaminophen | 325 mg |
| Promethazine HCl | 12.5 mg |
| Naltrexone | 0.5 mg or 0.75 mg |

Example 11

In one example, the composition of Example 10 is in the form of a bi-layer tablet having an immediate-release layer comprising 12.5 mg of promethazine hydrochloride, and having a controlled-release layer comprising 5 or 7.5 mg of oxycodone HCl and 325 mg of acetaminophen.

Example 12

The composition of Example 10 is orally administered with water to a subject having a tendency to exhibit adverse effects of opioid administration, such as gastric upset, nausea, vomiting, skin rash, sedation, CNS depression, or respiratory depression. Such subjects, upon taking the composition set forth in Example 10 will receive an effective amount of promethazine in their blood stream. The promethazine will reduce the adverse effects that such a target population would otherwise exhibit.

Example 13

Example of a bi-layer tablet analgesic composition comprising Hydrocodone or a Pharmaceutically Acceptable Salt Thereof, Acetaminophen and Promethazine or a Pharmaceutically Acceptable Salt Thereof. In one example, a bi-layer tablet comprises: (1) a controlled-release layer comprising (a) from about 6.5 mg to about 8.5 mg of hydrocodone or a pharmaceutically acceptable salt thereof, (b) from about 290 to about 360 mg of acetaminophen or a pharmaceutically acceptable salt thereof, (c) from about 135 mg to about 170 mg of silicified microcrystalline cellulose, (d) from about 17 mg to about 23 mg of hydroxy methyl propyl cellulose, (e) from about 1 mg to about 4 mg of magnesium stearate, and (f) from about 1 mg to about 4 mg of stearic acid; and (2) an immediate-release layer comprising (a) from about 11 mg to about 14 mg of promethazine or a pharmaceutically acceptable salt thereof, (b) from about 100 mg to about 140 mg of silicified microcrystalline cellulose, (c) from about 12 mg to about 18 mg of croscarmellose sodium and (d) from about 0.8 mg to about 1.5 mg of magnesium stearate. In another example, a bi-layer tablet's controlled-release layer comprises about 7.5 mg of hydrocodone or a pharmaceutically acceptable salt thereof, about 325 mg of acetaminophen or a pharmaceutically acceptable salt thereof, about 152 mg of silicified microcrystalline cellulose, about 20 mg of hydroxy methyl propyl cellulose, about 2.7 mg of magnesium stearate, and about 2.7 mg of stearic acid; and tablet's immediate release layer comprises about 12.5 mg of promethazine or a pharmaceutically acceptable salt thereof, about 121.5 mg of silicified microcrystalline cellulose, about 15 mg of croscarmellose sodium and about 1 mg of magnesium stearate.

Analgesic Composition F.1

| Top Layer - Immediate Release Layer | |
| --- | --- |
| Ingredient | Quantity/Tablet (mg) |
| Promethazine HCl | 12.5 mg |
| Prosolve SMCC (HD90) | 121.5 mg |
| Croscarmellose Sodium | 15 mg |
| Crospovidone NF | 15 mg |
| Avicel PH200 | 21.5 mg |
| Magnesium Stearate | 1 mg |
| Total Top Layer Weight | 186.5 mg |

| Bottom Layer- Controlled-Release Layer | |
| --- | --- |
| Ingredient | Quantity/Tablet (mg) |
| Acetaminophen 89.5% | 360.5 mg |
| Hydrocodone Bitartrate | 7.5 mg |
| Silicified Microcrystalline Cellulose | 150 mg |
| Hydroxy Methyl Propyl Cellulose | 10 mg |
| Croscarmellose Sodium | 23 mg |
| Magnesium Stearate | 15 mg |
| Total Bottom Layer Weight | 566 mg |

Analgesic Composition F.2

| Top Layer - Immediate Release Layer | |
| --- | --- |
| Ingredient | Quantity/Tablet (mg) |
| Promethazine HCl | 12.5 mg |
| Silicified Microcrystalline Cellulose | 121.5 mg |
| Croscarmellose Sodium | 15 mg |
| Magnesium Stearate | 1 mg |
| Total Top Layer Weight | 150.0 mg |

| Bottom Layer- Controlled-Release Layer | |
| --- | --- |
| Ingredient | Quantity/Tablet (mg) |
| Acetaminophen 89.05% | 364.96 mg |
| Hydrocodone bitartrate | 7.5 mg |
| Silicified Microcrystalline Cellulose | 152.04 mg |
| Hydroxy Methyl Propyl Cellulose | 20 mg |
| Stearic Acid | 2.75 mg |
| Magnesium Stearate | 2.75 mg |
| Total Bottom Layer Weight | 566 mg |

Example 14

The composition of Example 13 is orally administered with water to a subject having a tendency to exhibit adverse effects of opioid administration, such as gastric upset, nausea, vomiting, skin rash, sedation, CNS depression, or respiratory depression. Such subjects, upon taking the composition set forth in Example 13 will receive an effective amount of promethazine in their blood stream. The promethazine will reduce the adverse effects that such a target population would otherwise exhibit.

Example 15

Dissolution Data

Dissolution apparatus was a USP Rotating Paddle Apparatus 2 with an automated sampling station (e.g., VK-8000 or equivalent). Dissolution fluid was 900 mL of de-aerated 0.01 N HCl, maintained at 37.0+/−0.5° C. during dissolution procedure. The fluid was prepared by diluting 5 mL of concentrated HCl in 6000 mL of de-aerated water, and mixed. To measure peaks, a dual wavelength detector (e.g., Hitachi L-2420) was used, or alternatively, two separate chromatographic systems can be used in order to measure the peaks at two different wavelengths.

Standard Solution Preparation: Each ingredient was weighed (e.g., 21 mg of hydrocodone bitrartrate) into a 50 mL volumetric flask, and diluted to volume with dissolution media. The resulting solution was mixed to form a stock solution. Different ingredients were similarly prepared to provide stock solutions (e.g., promethazine HCl, acetaminophen). 2 mL each of stock standard solutions were diluted with dissolution fluid and mixed to produce a final standard solution. For example, the concentration of hydrocodone bitartrate was about 0.0084 mg/mL, promethazine HCl was about 0.014 mg/mL, and acetaminophen was about 0.36 mg/mL.

Dissolution test solutions were prepared in 900 mL of 0.01 N HCl using the USP Rotating Paddle Apparatus at 50 WM. An aliquot of the dissolution solution was filtered and a 50-pL aliquot was chromatographed on a 50-mm×4.6-mm (i.d.) Waters SunFire™ $C_{18}$, 3.5-μm particle size column using a gradient HPLC method. Mobile phase A consisted of water/acetonitrile/TFA, 950/50/2 (v/v/v) and mobile phase B consisted of water/acetonitrile/TFA, 50/950/1.5 (v/v/v). The flow rate was 2.0 mL/minute. For example, the amount of acetaminophen released was determined at 300 nm by comparing the area obtained for the peak due to acetaminophen in the chromatogram of the dissolution test solution to that obtained for the corresponding peak in a chromatogram of a standard solution. The amount of hydrocodone bitartrate released was determined at 230 nm by comparing the area obtained for the peak due to hydrocodone bitartrate in the chromatogram of the dissolution test solution to that obtained for the corresponding peak in a chromatogram of a standard solution. The amount of promethazine HCl released was determined at 230 nm by comparing the area obtained for the peak due to promethazine HCl in the chromatogram of the dissolution test solution to that obtained for the corresponding peak in a chromatogram of a standard solution.

Paddle speed was 50 rpm; pull volume was 10 mL (no replacement); Pull points: 5, 10, 15, 20, 25, 30, 45 and 60 minutes. The amount of each component dissolved in the dissolution medium was determined by HPLC. The method can use a high purity, bonded C18 stationary phase and a binary mobile phase consisting of an appropriate buffer and organic modifier.

Dissolution Procedure. 900 mL of dissolution fluid preheated to 37° C. was placed into each vessel. Tablets of Analgesic Composition F.2 above were weighed and placed in vessels respectively. At prescribed time intervals, 5 mL aliquot of the dissolution fluid was drawn using the automated sampling station equipped with a 35 μm full flow filter connected to a sampling probe. Filtrate was allowed to cool to room temperature, to produce a final sample solution. Fluid withdrawn was not replaced. Samples were injected in HPLC for analysis after a baseline was established. Peak area responses were measured for each component: acetaminophen peak eluted at about 1.5 minutes; hydrocodone bitartrate eluted at about 3.3 minutes and promethazine HCl eluted at about 4.8 minutes. The resolution between each peak was calculated, as well as the tailing factor. The mean and % RSD values for the acetaminophen peak areas at 300 nm were measured; promethazine HCl and hydrocodone bitartrate at 230 nm. The five replicate injections were not more than 2.0% RSD. 50 μL aliquots of standard and sample solutions were subjected to liquid chromatography. A typical chromatogram of a standard solution is illustrated in FIG. 1.

Figure 3:
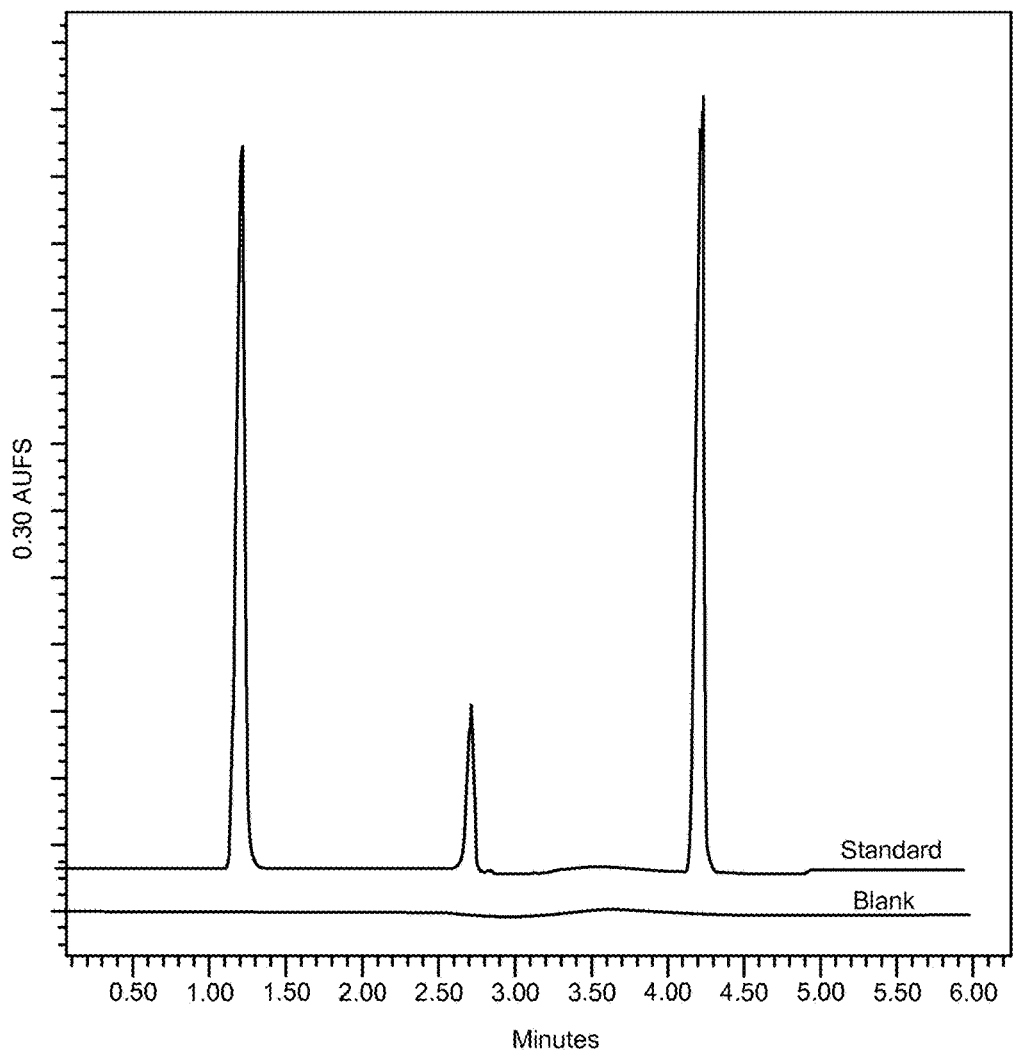
FIG. 3 illustrates an example of chromatograph of a diluent blank and standard solution.
Figure 4:
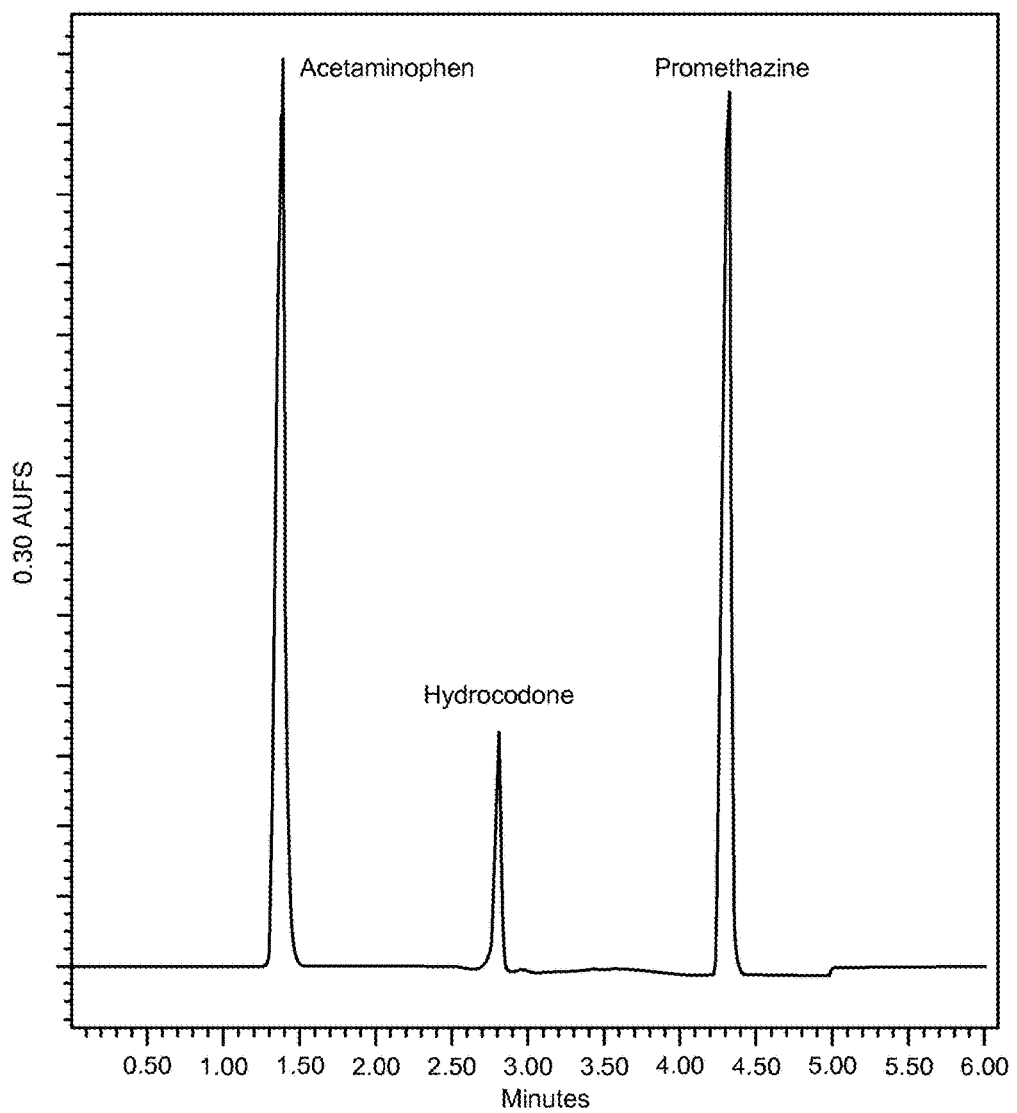
FIG. 4 illustrates an example of a dissolution chromatograph for a composition of the invention.

The amount of a pharmaceutically active agent in a tablet is determined by comparing the area obtained for the peak due to the agent in a chromatogram of the dissolution test solution to that obtained for the corresponding peak in a chromatogram of a standard solution. For example the standard peaks are provided in FIG. 3, while the test solutions are provide in FIG. 4.

Example 16

The compositions of Table 1 or Table 2 can be formulated in formulated in a variety of dosage forms (e.g., tablets, capsules, geld, lollipops), parenteral, intraspinal infusion, inhalations, nasal sprays, transdermal patches, iontophoresis transport, absorbing gels, liquids, liquid tannates, suppositories, injections, I.V. drips, other delivery methods, or a combination thereof to treat subjects. In some embodiments each agent disclosed in Table 1 or Table 2 can be present in a composition as its pharmaceutically acceptable salt. In one embodiment the hydrocodone of the compositions of Table 1 is in the form of hydrocodone bitartrate; in another embodiment the oxycodone of the compositions of Table 1 is in the form of oxycodone hydrochloride; in another embodiment the ibuprofen of the compositions of Table 1 is in the form of ibruprofen sodium; in another embodiment the naproxen of the compositions of Table 1 is in the form of naproxen sodium; in another embodiment the promethazine of the compositions of Table 1 or Table 2 is in the form of promethazine hydrochloride; and in another embodiment the naltrexone of the compositions of Table 1 is in the form of naltrexone hydrochloride. In some embodiments a dosage form comprising an effective amount of promethazine or a pharmaceutically acceptable salt thereof will be orally administered to a subject having a tendency to exhibit one or more adverse effect of opioid administration, such as gastric upset, nausea, vomiting, skin rash, sedation, CNS depression, or respiratory depression in response to opioid administration. In one embodiment one or more of compositions of Table 1 or Table 2 are in the form of a bi-layer tablet comprising an immediate release layer and a controlled release layer. In one embodiment the controlled-release layer comprises hydrocodone, oxycodone, propoxyphene, ibuprofen, acetaminophen, naproxen or a pharmaceutically acceptable salt thereof and the immediate-release layer comprises promethazine or a pharmaceutically acceptable salt thereof.

TABLE 1

Multi-drug Compositions

| Composition No. | Opioid agent | Non-opioid agent | Antiemetic agent | Barbiturate agent | Stimulant agent | Opioid antagonist agent | Abuse deterrent agent |
|---|---|---|---|---|---|---|---|
| 1 | Hydrocodone | Acetaminophen | — | — | — | — | — |
| 2 | Hydrocodone | — | Promethazine | — | — | — | — |
| 3 | Hydrocodone | — | — | Butalbital | — | — | — |
| 4 | Hydrocodone | — | — | — | Modafinil | — | — |
| 5 | Hydrocodone | — | — | — | Caffeine | — | — |
| 6 | Hydrocodone | — | — | — | — | Naltrexone | — |
| 7 | Hydrocodone | — | — | — | — | — | Niacin |

TABLE 1-continued

Multi-drug Compositions

| Composition No. | Opioid agent | Non-opioid agent | Antiemetic agent | Barbiturate agent | Stimulant agent | Opioid antagonist agent | Abuse deterrent agent |
|---|---|---|---|---|---|---|---|
| 8 | Hydrocodone | Acetaminophen | Promethazine | — | — | — | — |
| 9 | Hydrocodone | Acetaminophen | — | Butalbital | — | — | — |
| 10 | Hydrocodone | Acetaminophen | — | — | Modafinil | — | — |
| 11 | Hydrocodone | Acetaminophen | — | — | Caffeine | — | — |
| 12 | Hydrocodone | Acetaminophen | — | — | — | Naltrexone | — |
| 13 | Hydrocodone | Acetaminophen | — | — | — | — | Niacin |
| 14 | Hydrocodone | — | Promethazine | Butalbital | — | — | — |
| 15 | Hydrocodone | — | Promethazine | — | Modafinil | — | — |
| 16 | Hydrocodone | — | Promethazine | — | Caffeine | — | — |
| 17 | Hydrocodone | — | Promethazine | — | — | Naltrexone | — |
| 18 | Hydrocodone | — | Promethazine | — | — | — | Niacin |
| 19 | Hydrocodone | — | — | Butalbital | Modafinil | — | — |
| 20 | Hydrocodone | — | — | Butalbital | Caffeine | — | — |
| 21 | Hydrocodone | — | — | Butalbital | — | Naltrexone | — |
| 22 | Hydrocodone | — | — | Butalbital | — | — | Niacin |
| 23 | Hydrocodone | — | — | — | Modafinil | Naltrexone | — |
| 24 | Hydrocodone | — | — | — | Caffeine | Naltrexone | — |
| 25 | Hydrocodone | — | — | — | Modafinil | — | Niacin |
| 26 | Hydrocodone | — | — | — | Caffeine | — | Niacin |
| 27 | Hydrocodone | — | — | — | — | Naltrexone | Niacin |
| 28 | Hydrocodone | Acetaminophen | Promethazine | Butalbital | — | — | — |
| 29 | Hydrocodone | Acetaminophen | Promethazine | — | Modafinil | — | — |
| 30 | Hydrocodone | Acetaminophen | Promethazine | — | Caffeine | — | — |
| 31 | Hydrocodone | Acetaminophen | Promethazine | — | — | Naltrexone | — |
| 32 | Hydrocodone | Acetaminophen | Promethazine | — | — | — | Niacin |
| 33 | Hydrocodone | Acetaminophen | — | Butalbital | Modafinil | — | — |
| 34 | Hydrocodone | Acetaminophen | — | Butalbital | Caffeine | — | — |
| 35 | Hydrocodone | Acetaminophen | — | Butalbital | — | Naltrexone | — |
| 36 | Hydrocodone | Acetaminophen | — | Butalbital | — | — | Niacin |
| 37 | Hydrocodone | Acetaminophen | — | — | Modafinil | Naltrexone | — |
| 38 | Hydrocodone | Acetaminophen | — | — | Modafinil | — | Niacin |
| 39 | Hydrocodone | Acetaminophen | — | — | Caffeine | Naltrexone | — |
| 40 | Hydrocodone | Acetaminophen | — | — | Caffeine | — | Niacin |
| 41 | Hydrocodone | Acetaminophen | — | — | — | Naltrexone | Niacin |
| 42 | Hydrocodone | — | Promethazine | Butalbital | Modafinil | — | — |
| 43 | Hydrocodone | — | Promethazine | Butalbital | Caffeine | — | — |
| 44 | Hydrocodone | — | Promethazine | Butalbital | — | Naltrexone | — |
| 45 | Hydrocodone | — | Promethazine | Butalbital | — | — | Niacin |
| 46 | Hydrocodone | — | Promethazine | — | Modafinil | Naltrexone | — |
| 47 | Hydrocodone | — | Promethazine | — | Caffeine | Naltrexone | — |
| 48 | Hydrocodone | — | Promethazine | — | Modafinil | — | Niacin |
| 49 | Hydrocodone | — | Promethazine | — | Caffeine | — | Niacin |
| 50 | Hydrocodone | — | Promethazine | — | — | Naltrexone | Niacin |
| 51 | Hydrocodone | — | — | Butalbital | Modafinil | Naltrexone | — |
| 52 | Hydrocodone | — | — | Butalbital | Caffeine | Naltrexone | — |
| 53 | Hydrocodone | — | — | Butalbital | Modafinil | — | Niacin |
| 54 | Hydrocodone | — | — | Butalbital | Caffeine | — | Niacin |
| 55 | Hydrocodone | — | — | Butalbital | — | Naltrexone | Niacin |
| 56 | Hydrocodone | — | — | — | Modafinil | Naltrexone | Niacin |
| 57 | Hydrocodone | — | — | — | Caffeine | Naltrexone | Niacin |
| 58 | Hydrocodone | Acetaminophen | Promethazine | Butalbital | Modafinil | — | — |
| 59 | Hydrocodone | Acetaminophen | Promethazine | Butalbital | Caffeine | — | — |
| 60 | Hydrocodone | Acetaminophen | Promethazine | Butalbital | — | Naltrexone | — |
| 61 | Hydrocodone | Acetaminophen | Promethazine | Butalbital | — | — | Niacin |
| 62 | Hydrocodone | Acetaminophen | Promethazine | — | Modafinil | Naltrexone | — |
| 63 | Hydrocodone | Acetaminophen | Promethazine | — | Caffeine | Naltrexone | — |
| 64 | Hydrocodone | Acetaminophen | Promethazine | — | Modafinil | — | Niacin |
| 65 | Hydrocodone | Acetaminophen | Promethazine | — | Caffeine | — | Niacin |
| 66 | Hydrocodone | Acetaminophen | Promethazine | — | — | Naltrexone | Niacin |
| 67 | Hydrocodone | Acetaminophen | — | Butalbital | Modafinil | Naltrexone | — |
| 68 | Hydrocodone | Acetaminophen | — | Butalbital | Caffeine | Naltrexone | — |
| 69 | Hydrocodone | Acetaminophen | — | Butalbital | Modafinil | — | Niacin |
| 70 | Hydrocodone | Acetaminophen | — | Butalbital | Caffeine | — | Niacin |
| 71 | Hydrocodone | Acetaminophen | — | Butalbital | — | Naltrexone | Niacin |
| 72 | Hydrocodone | Acetaminophen | — | — | Modafinil | Naltrexone | Niacin |
| 73 | Hydrocodone | Acetaminophen | — | — | Caffeine | Naltrexone | Niacin |
| 74 | Hydrocodone | — | Promethazine | Butalbital | Modafinil | Naltrexone | — |
| 75 | Hydrocodone | — | Promethazine | Butalbital | Caffeine | Naltrexone | — |
| 76 | Hydrocodone | — | Promethazine | Butalbital | Modafinil | — | Niacin |
| 77 | Hydrocodone | — | Promethazine | Butalbital | Caffeine | — | Niacin |
| 78 | Hydrocodone | — | Promethazine | Butalbital | — | Naltrexone | Niacin |
| 79 | Hydrocodone | — | — | Butalbital | Caffeine | Naltrexone | Niacin |
| 80 | Hydrocodone | Acetaminophen | Promethazine | Butalbital | Modafinil | Naltrexone | — |
| 81 | Hydrocodone | Acetaminophen | Promethazine | Butalbital | Caffeine | Naltrexone | — |

TABLE 1-continued

Multi-drug Compositions

| Composition No. | Opioid agent | Non-opioid agent | Antiemetic agent | Barbiturate agent | Stimulant agent | Opioid antagonist agent | Abuse deterrent agent |
|---|---|---|---|---|---|---|---|
| 82 | Hydrocodone | Acetaminophen | Promethazine | Butalbital | Modafinil | — | Niacin |
| 83 | Hydrocodone | Acetaminophen | Promethazine | Butalbital | Caffeine | — | Niacin |
| 84 | Hydrocodone | — | Promethazine | Butalbital | Modafinil | Naltrexone | Niacin |
| 85 | Hydrocodone | — | Promethazine | Butalbital | Caffeine | Naltrexone | Niacin |
| 86 | Hydrocodone | Acetaminophen | — | Butalbital | Modafinil | Naltrexone | Niacin |
| 87 | Hydrocodone | Acetaminophen | — | Butalbital | Caffeine | Naltrexone | Niacin |
| 88 | Hydrocodone | Acetaminophen | Promethazine | — | Modafinil | Naltrexone | Niacin |
| 89 | Hydrocodone | Acetaminophen | Promethazine | — | Caffeine | Naltrexone | Niacin |
| 90 | Hydrocodone | Acetaminophen | Promethazine | Butalbital | — | Naltrexone | Niacin |
| 91 | Hydrocodone | Acetaminophen | Promethazine | Butalbital | Modafinil | Naltrexone | Niacin |
| 92 | Hydrocodone | Acetaminophen | Promethazine | Butalbital | Caffeine | Naltrexone | Niacin |
| 93 | Hydrocodone | Naproxen | — | — | — | — | — |
| 94 | Hydrocodone | — | Promethazine | — | — | — | — |
| 95 | Hydrocodone | — | — | Butalbital | — | — | — |
| 96 | Hydrocodone | — | — | — | Modafinil | — | — |
| 97 | Hydrocodone | — | — | — | Caffeine | — | — |
| 98 | Hydrocodone | — | — | — | — | Naltrexone | — |
| 99 | Hydrocodone | — | — | — | — | — | Niacin |
| 100 | Hydrocodone | Naproxen | Promethazine | — | — | — | — |
| 101 | Hydrocodone | Naproxen | — | Butalbital | — | — | — |
| 102 | Hydrocodone | Naproxen | — | — | Modafinil | — | — |
| 103 | Hydrocodone | Naproxen | — | — | Caffeine | — | — |
| 104 | Hydrocodone | Naproxen | — | — | — | Naltrexone | — |
| 105 | Hydrocodone | Naproxen | — | — | — | — | Niacin |
| 106 | Hydrocodone | — | Promethazine | Butalbital | — | — | — |
| 107 | Hydrocodone | — | Promethazine | — | Modafinil | — | — |
| 108 | Hydrocodone | — | Promethazine | — | Caffeine | — | — |
| 109 | Hydrocodone | — | Promethazine | — | — | Naltrexone | — |
| 110 | Hydrocodone | — | Promethazine | — | — | — | Niacin |
| 111 | Hydrocodone | — | — | Butalbital | Modafinil | — | — |
| 112 | Hydrocodone | — | — | Butalbital | Caffeine | — | — |
| 113 | Hydrocodone | — | — | Butalbital | — | Naltrexone | — |
| 114 | Hydrocodone | — | — | Butalbital | — | — | Niacin |
| 115 | Hydrocodone | — | — | — | Modafinil | Naltrexone | — |
| 116 | Hydrocodone | — | — | — | Caffeine | Naltrexone | — |
| 117 | Hydrocodone | — | — | — | Modafinil | — | Niacin |
| 118 | Hydrocodone | — | — | — | Caffeine | — | Niacin |
| 119 | Hydrocodone | — | — | — | — | Naltrexone | Niacin |
| 120 | Hydrocodone | Naproxen | Promethazine | Butalbital | — | — | — |
| 121 | Hydrocodone | Naproxen | Promethazine | — | Modafinil | — | — |
| 122 | Hydrocodone | Naproxen | Promethazine | — | Caffeine | — | — |
| 123 | Hydrocodone | Naproxen | Promethazine | — | — | Naltrexone | — |
| 124 | Hydrocodone | Naproxen | Promethazine | — | — | — | Niacin |
| 125 | Hydrocodone | Naproxen | — | Butalbital | Modafinil | — | — |
| 126 | Hydrocodone | Naproxen | — | Butalbital | Caffeine | — | — |
| 127 | Hydrocodone | Naproxen | — | Butalbital | — | Naltrexone | — |
| 128 | Hydrocodone | Naproxen | — | Butalbital | — | — | Niacin |
| 129 | Hydrocodone | Naproxen | — | — | Modafinil | Naltrexone | — |
| 130 | Hydrocodone | Naproxen | — | — | Modafinil | — | Niacin |
| 131 | Hydrocodone | Naproxen | — | — | Caffeine | Naltrexone | — |
| 132 | Hydrocodone | Naproxen | — | — | Caffeine | — | Niacin |
| 133 | Hydrocodone | Naproxen | — | — | — | Naltrexone | Niacin |
| 134 | Hydrocodone | — | Promethazine | Butalbital | Modafinil | — | — |
| 135 | Hydrocodone | — | Promethazine | Butalbital | Caffeine | — | — |
| 136 | Hydrocodone | — | Promethazine | Butalbital | — | Naltrexone | — |
| 137 | Hydrocodone | — | Promethazine | Butalbital | — | — | Niacin |
| 138 | Hydrocodone | — | Promethazine | — | Modafinil | Naltrexone | — |
| 139 | Hydrocodone | — | Promethazine | — | Caffeine | Naltrexone | — |
| 140 | Hydrocodone | — | Promethazine | — | Modafinil | — | Niacin |
| 141 | Hydrocodone | — | Promethazine | — | Caffeine | — | Niacin |
| 142 | Hydrocodone | — | Promethazine | — | — | Naltrexone | Niacin |
| 143 | Hydrocodone | — | — | Butalbital | Modafinil | Naltrexone | — |
| 144 | Hydrocodone | — | — | Butalbital | Caffeine | Naltrexone | — |
| 145 | Hydrocodone | — | — | Butalbital | Modafinil | — | Niacin |
| 146 | Hydrocodone | — | — | Butalbital | Caffeine | — | Niacin |
| 147 | Hydrocodone | — | — | Butalbital | — | Naltrexone | Niacin |
| 148 | Hydrocodone | — | — | — | Modafinil | Naltrexone | Niacin |
| 149 | Hydrocodone | — | — | — | Caffeine | Naltrexone | Niacin |
| 150 | Hydrocodone | Naproxen | Promethazine | Butalbital | Modafinil | — | — |
| 151 | Hydrocodone | Naproxen | Promethazine | Butalbital | Caffeine | — | — |
| 152 | Hydrocodone | Naproxen | Promethazine | Butalbital | — | Naltrexone | — |
| 153 | Hydrocodone | Naproxen | Promethazine | Butalbital | — | — | Niacin |
| 154 | Hydrocodone | Naproxen | Promethazine | — | Modafinil | Naltrexone | — |
| 155 | Hydrocodone | Naproxen | Promethazine | — | Caffeine | Naltrexone | — |

TABLE 1-continued

Multi-drug Compositions

| Composition No. | Opioid agent | Non-opioid agent | Antiemetic agent | Barbiturate agent | Stimulant agent | Opioid antagonist agent | Abuse deterrent agent |
|---|---|---|---|---|---|---|---|
| 156 | Hydrocodone | Naproxen | Promethazine | — | Modafinil | — | Niacin |
| 157 | Hydrocodone | Naproxen | Promethazine | — | Caffeine | — | Niacin |
| 158 | Hydrocodone | Naproxen | Promethazine | — | — | Naltrexone | Niacin |
| 159 | Hydrocodone | Naproxen | — | Butalbital | Modafinil | Naltrexone | — |
| 160 | Hydrocodone | Naproxen | — | Butalbital | Caffeine | Naltrexone | — |
| 161 | Hydrocodone | Naproxen | — | Butalbital | Modafinil | — | Niacin |
| 162 | Hydrocodone | Naproxen | — | Butalbital | Caffeine | — | Niacin |
| 163 | Hydrocodone | Naproxen | — | Butalbital | — | Naltrexone | Niacin |
| 164 | Hydrocodone | Naproxen | — | — | Modafinil | Naltrexone | Niacin |
| 165 | Hydrocodone | Naproxen | — | — | Caffeine | Naltrexone | Niacin |
| 166 | Hydrocodone | — | Promethazine | Butalbital | Modafinil | Naltrexone | — |
| 167 | Hydrocodone | — | Promethazine | Butalbital | Caffeine | Naltrexone | — |
| 168 | Hydrocodone | — | Promethazine | Butalbital | Modafinil | — | Niacin |
| 169 | Hydrocodone | — | Promethazine | Butalbital | Caffeine | — | Niacin |
| 170 | Hydrocodone | — | Promethazine | Butalbital | — | Naltrexone | Niacin |
| 171 | Hydrocodone | — | — | Butalbital | Caffeine | Naltrexone | Niacin |
| 172 | Hydrocodone | Naproxen | Promethazine | Butalbital | Modafinil | Naltrexone | — |
| 173 | Hydrocodone | Naproxen | Promethazine | Butalbital | Caffeine | Naltrexone | — |
| 174 | Hydrocodone | Naproxen | Promethazine | Butalbital | Modafinil | — | Niacin |
| 175 | Hydrocodone | Naproxen | Promethazine | Butalbital | Caffeine | — | Niacin |
| 176 | Hydrocodone | — | Promethazine | Butalbital | Modafinil | Naltrexone | Niacin |
| 177 | Hydrocodone | — | Promethazine | Butalbital | Caffeine | Naltrexone | Niacin |
| 178 | Hydrocodone | Naproxen | — | Butalbital | Modafinil | Naltrexone | Niacin |
| 179 | Hydrocodone | Naproxen | — | Butalbital | Caffeine | Naltrexone | Niacin |
| 180 | Hydrocodone | Naproxen | Promethazine | — | Modafinil | Naltrexone | Niacin |
| 181 | Hydrocodone | Naproxen | Promethazine | — | Caffeine | Naltrexone | Niacin |
| 182 | Hydrocodone | Naproxen | Promethazine | Butalbital | — | Naltrexone | Niacin |
| 183 | Hydrocodone | Naproxen | Promethazine | Butalbital | Modafinil | Naltrexone | Niacin |
| 184 | Hydrocodone | Naproxen | Promethazine | Butalbital | Caffeine | Naltrexone | Niacin |
| 185 | Hydrocodone | Ibuprofen | — | — | — | — | — |
| 186 | Hydrocodone | — | Promethazine | — | — | — | — |
| 187 | Hydrocodone | — | — | Butalbital | — | — | — |
| 188 | Hydrocodone | — | — | — | Modafinil | — | — |
| 189 | Hydrocodone | — | — | — | Caffeine | — | — |
| 190 | Hydrocodone | — | — | — | — | Naltrexone | — |
| 191 | Hydrocodone | — | — | — | — | — | Niacin |
| 192 | Hydrocodone | Ibuprofen | Promethazine | — | — | — | — |
| 193 | Hydrocodone | Ibuprofen | — | Butalbital | — | — | — |
| 194 | Hydrocodone | Ibuprofen | — | — | Modafinil | — | — |
| 195 | Hydrocodone | Ibuprofen | — | — | Caffeine | — | — |
| 196 | Hydrocodone | Ibuprofen | — | — | — | Naltrexone | — |
| 197 | Hydrocodone | Ibuprofen | — | — | — | — | Niacin |
| 198 | Hydrocodone | — | Promethazine | Butalbital | — | — | — |
| 199 | Hydrocodone | — | Promethazine | — | Modafinil | — | — |
| 200 | Hydrocodone | — | Promethazine | — | Caffeine | — | — |
| 201 | Hydrocodone | — | Promethazine | — | — | Naltrexone | — |
| 202 | Hydrocodone | — | Promethazine | — | — | — | Niacin |
| 203 | Hydrocodone | — | — | Butalbital | Modafinil | — | — |
| 204 | Hydrocodone | — | — | Butalbital | Caffeine | — | — |
| 205 | Hydrocodone | — | — | Butalbital | — | Naltrexone | — |
| 206 | Hydrocodone | — | — | Butalbital | — | — | Niacin |
| 207 | Hydrocodone | — | — | — | Modafinil | Naltrexone | — |
| 208 | Hydrocodone | — | — | — | Caffeine | Naltrexone | — |
| 209 | Hydrocodone | — | — | — | Modafinil | — | Niacin |
| 210 | Hydrocodone | — | — | — | Caffeine | — | Niacin |
| 211 | Hydrocodone | — | — | — | — | Naltrexone | Niacin |
| 212 | Hydrocodone | Ibuprofen | Promethazine | Butalbital | — | — | — |
| 213 | Hydrocodone | Ibuprofen | Promethazine | — | Modafinil | — | — |
| 214 | Hydrocodone | Ibuprofen | Promethazine | — | Caffeine | — | — |
| 215 | Hydrocodone | Ibuprofen | Promethazine | — | — | Naltrexone | — |
| 216 | Hydrocodone | Ibuprofen | Promethazine | — | — | — | Niacin |
| 217 | Hydrocodone | Ibuprofen | — | Butalbital | Modafinil | — | — |
| 218 | Hydrocodone | Ibuprofen | — | Butalbital | Caffeine | — | — |
| 219 | Hydrocodone | Ibuprofen | — | Butalbital | — | Naltrexone | — |
| 220 | Hydrocodone | Ibuprofen | — | Butalbital | — | — | Niacin |
| 221 | Hydrocodone | Ibuprofen | — | — | Modafinil | Naltrexone | — |
| 222 | Hydrocodone | Ibuprofen | — | — | Modafinil | — | Niacin |
| 223 | Hydrocodone | Ibuprofen | — | — | Caffeine | Naltrexone | — |
| 224 | Hydrocodone | Ibuprofen | — | — | Caffeine | — | Niacin |
| 225 | Hydrocodone | Ibuprofen | — | — | — | Naltrexone | Niacin |
| 226 | Hydrocodone | — | Promethazine | Butalbital | Modafinil | — | — |
| 227 | Hydrocodone | — | Promethazine | Butalbital | Caffeine | — | — |
| 228 | Hydrocodone | — | Promethazine | Butalbital | — | Naltrexone | — |
| 229 | Hydrocodone | — | Promethazine | Butalbital | — | — | Niacin |

TABLE 1-continued

Multi-drug Compositions

| Composition No. | Opioid agent | Non-opioid agent | Antiemetic agent | Barbiturate agent | Stimulant agent | Opioid antagonist agent | Abuse deterrent agent |
|---|---|---|---|---|---|---|---|
| 230 | Hydrocodone | — | Promethazine | — | Modafinil | Naltrexone | — |
| 231 | Hydrocodone | — | Promethazine | — | Caffeine | Naltrexone | — |
| 232 | Hydrocodone | — | Promethazine | — | Modafinil | — | Niacin |
| 233 | Hydrocodone | — | Promethazine | — | Caffeine | — | Niacin |
| 234 | Hydrocodone | — | Promethazine | — | — | Naltrexone | Niacin |
| 235 | Hydrocodone | — | — | Butalbital | Modafinil | Naltrexone | — |
| 236 | Hydrocodone | — | — | Butalbital | Caffeine | Naltrexone | — |
| 237 | Hydrocodone | — | — | Butalbital | Modafinil | — | Niacin |
| 238 | Hydrocodone | — | — | Butalbital | Caffeine | — | Niacin |
| 239 | Hydrocodone | — | — | Butalbital | — | Naltrexone | Niacin |
| 240 | Hydrocodone | — | — | — | Modafinil | Naltrexone | Niacin |
| 241 | Hydrocodone | — | — | — | Caffeine | Naltrexone | Niacin |
| 242 | Hydrocodone | Ibuprofen | Promethazine | Butalbital | Modafinil | — | — |
| 243 | Hydrocodone | Ibuprofen | Promethazine | Butalbital | Caffeine | — | — |
| 244 | Hydrocodone | Ibuprofen | Promethazine | Butalbital | — | Naltrexone | — |
| 245 | Hydrocodone | Ibuprofen | Promethazine | Butalbital | — | — | Niacin |
| 246 | Hydrocodone | Ibuprofen | Promethazine | — | Modafinil | Naltrexone | — |
| 247 | Hydrocodone | Ibuprofen | Promethazine | — | Caffeine | Naltrexone | — |
| 248 | Hydrocodone | Ibuprofen | Promethazine | — | Modafinil | — | Niacin |
| 249 | Hydrocodone | Ibuprofen | Promethazine | — | Caffeine | — | Niacin |
| 250 | Hydrocodone | Ibuprofen | Promethazine | — | — | Naltrexone | Niacin |
| 251 | Hydrocodone | Ibuprofen | — | Butalbital | Modafinil | Naltrexone | — |
| 252 | Hydrocodone | Ibuprofen | — | Butalbital | Caffeine | Naltrexone | — |
| 253 | Hydrocodone | Ibuprofen | — | Butalbital | Modafinil | — | Niacin |
| 254 | Hydrocodone | Ibuprofen | — | Butalbital | Caffeine | — | Niacin |
| 255 | Hydrocodone | Ibuprofen | — | Butalbital | — | Naltrexone | Niacin |
| 256 | Hydrocodone | Ibuprofen | — | — | Modafinil | Naltrexone | Niacin |
| 257 | Hydrocodone | Ibuprofen | — | — | Caffeine | Naltrexone | Niacin |
| 258 | Hydrocodone | — | Promethazine | Butalbital | Modafinil | Naltrexone | — |
| 259 | Hydrocodone | — | Promethazine | Butalbital | Caffeine | Naltrexone | — |
| 260 | Hydrocodone | — | Promethazine | Butalbital | Modafinil | — | Niacin |
| 261 | Hydrocodone | — | Promethazine | Butalbital | Caffeine | — | Niacin |
| 262 | Hydrocodone | — | Promethazine | Butalbital | — | Naltrexone | Niacin |
| 263 | Hydrocodone | — | — | Butalbital | Caffeine | Naltrexone | Niacin |
| 264 | Hydrocodone | Ibuprofen | Promethazine | Butalbital | Modafinil | Naltrexone | — |
| 265 | Hydrocodone | Ibuprofen | Promethazine | Butalbital | Caffeine | Naltrexone | — |
| 266 | Hydrocodone | Ibuprofen | Promethazine | Butalbital | Modafinil | — | Niacin |
| 267 | Hydrocodone | Ibuprofen | Promethazine | Butalbital | Caffeine | — | Niacin |
| 268 | Hydrocodone | — | Promethazine | Butalbital | Modafinil | Naltrexone | Niacin |
| 269 | Hydrocodone | — | Promethazine | Butalbital | Caffeine | Naltrexone | Niacin |
| 270 | Hydrocodone | Ibuprofen | — | Butalbital | Modafinil | Naltrexone | Niacin |
| 271 | Hydrocodone | Ibuprofen | — | Butalbital | Caffeine | Naltrexone | Niacin |
| 272 | Hydrocodone | Ibuprofen | Promethazine | — | Modafinil | Naltrexone | Niacin |
| 273 | Hydrocodone | Ibuprofen | Promethazine | — | Caffeine | Naltrexone | Niacin |
| 274 | Hydrocodone | Ibuprofen | Promethazine | Butalbital | — | Naltrexone | Niacin |
| 275 | Hydrocodone | Ibuprofen | Promethazine | Butalbital | Modafinil | Naltrexone | Niacin |
| 276 | Hydrocodone | Ibuprofen | Promethazine | Butalbital | Caffeine | Naltrexone | Niacin |
| 277 | Oxycodone | Acetaminophen | — | — | — | — | — |
| 278 | Oxycodone | — | Promethazine | — | — | — | — |
| 279 | Oxycodone | — | — | Butalbital | — | — | — |
| 280 | Oxycodone | — | — | — | Modafinil | — | — |
| 281 | Oxycodone | — | — | — | Caffeine | — | — |
| 282 | Oxycodone | — | — | — | — | Naltrexone | — |
| 283 | Oxycodone | — | — | — | — | — | Niacin |
| 284 | Oxycodone | Acetaminophen | Promethazine | — | — | — | — |
| 285 | Oxycodone | Acetaminophen | — | Butalbital | — | — | — |
| 286 | Oxycodone | Acetaminophen | — | — | Modafinil | — | — |
| 287 | Oxycodone | Acetaminophen | — | — | Caffeine | — | — |
| 288 | Oxycodone | Acetaminophen | — | — | — | Naltrexone | — |
| 289 | Oxycodone | Acetaminophen | — | — | — | — | Niacin |
| 290 | Oxycodone | — | Promethazine | Butalbital | — | — | — |
| 291 | Oxycodone | — | Promethazine | — | Modafinil | — | — |
| 292 | Oxycodone | — | Promethazine | — | Caffeine | — | — |
| 293 | Oxycodone | — | Promethazine | — | — | Naltrexone | — |
| 294 | Oxycodone | — | Promethazine | — | — | — | Niacin |
| 295 | Oxycodone | — | — | Butalbital | Modafinil | — | — |
| 296 | Oxycodone | — | — | Butalbital | Caffeine | — | — |
| 297 | Oxycodone | — | — | Butalbital | — | Naltrexone | — |
| 298 | Oxycodone | — | — | Butalbital | — | — | Niacin |
| 299 | Oxycodone | — | — | — | Modafinil | Naltrexone | — |
| 300 | Oxycodone | — | — | — | Caffeine | Naltrexone | — |
| 301 | Oxycodone | — | — | — | Modafinil | — | Niacin |
| 302 | Oxycodone | — | — | — | Caffeine | — | Niacin |
| 303 | Oxycodone | — | — | — | — | Naltrexone | Niacin |

TABLE 1-continued

Multi-drug Compositions

| Composition No. | Opioid agent | Non-opioid agent | Antiemetic agent | Barbiturate agent | Stimulant agent | Opioid antagonist agent | Abuse deterrent agent |
|---|---|---|---|---|---|---|---|
| 304 | Oxycodone | Acetaminophen | Promethazine | Butalbital | — | — | — |
| 305 | Oxycodone | Acetaminophen | Promethazine | — | Modafinil | — | — |
| 306 | Oxycodone | Acetaminophen | Promethazine | — | Caffeine | — | — |
| 307 | Oxycodone | Acetaminophen | Promethazine | — | — | Naltrexone | — |
| 308 | Oxycodone | Acetaminophen | Promethazine | — | — | — | Niacin |
| 309 | Oxycodone | Acetaminophen | — | Butalbital | Modafinil | — | — |
| 310 | Oxycodone | Acetaminophen | — | Butalbital | Caffeine | — | — |
| 311 | Oxycodone | Acetaminophen | — | Butalbital | — | Naltrexone | — |
| 312 | Oxycodone | Acetaminophen | — | Butalbital | — | — | Niacin |
| 313 | Oxycodone | Acetaminophen | — | — | Modafinil | Naltrexone | — |
| 314 | Oxycodone | Acetaminophen | — | — | Modafinil | — | Niacin |
| 315 | Oxycodone | Acetaminophen | — | — | Caffeine | Naltrexone | — |
| 316 | Oxycodone | Acetaminophen | — | — | Caffeine | — | Niacin |
| 317 | Oxycodone | Acetaminophen | — | — | — | Naltrexone | Niacin |
| 318 | Oxycodone | — | Promethazine | Butalbital | Modafinil | — | — |
| 319 | Oxycodone | — | Promethazine | Butalbital | Caffeine | — | — |
| 320 | Oxycodone | — | Promethazine | Butalbital | — | Naltrexone | — |
| 321 | Oxycodone | — | Promethazine | Butalbital | — | — | Niacin |
| 322 | Oxycodone | — | Promethazine | — | Modafinil | Naltrexone | — |
| 323 | Oxycodone | — | Promethazine | — | Caffeine | Naltrexone | — |
| 324 | Oxycodone | — | Promethazine | — | Modafinil | — | Niacin |
| 325 | Oxycodone | — | Promethazine | — | Caffeine | — | Niacin |
| 326 | Oxycodone | — | Promethazine | — | — | Naltrexone | Niacin |
| 327 | Oxycodone | — | — | Butalbital | Modafinil | Naltrexone | — |
| 328 | Oxycodone | — | — | Butalbital | Caffeine | Naltrexone | — |
| 329 | Oxycodone | — | — | Butalbital | Modafinil | — | Niacin |
| 330 | Oxycodone | — | — | Butalbital | Caffeine | — | Niacin |
| 331 | Oxycodone | — | — | Butalbital | — | Naltrexone | Niacin |
| 332 | Oxycodone | — | — | — | Modafinil | Naltrexone | Niacin |
| 333 | Oxycodone | — | — | — | Caffeine | Naltrexone | Niacin |
| 334 | Oxycodone | Acetaminophen | Promethazine | Butalbital | Modafinil | — | — |
| 335 | Oxycodone | Acetaminophen | Promethazine | Butalbital | Caffeine | — | — |
| 336 | Oxycodone | Acetaminophen | Promethazine | Butalbital | — | Naltrexone | — |
| 337 | Oxycodone | Acetaminophen | Promethazine | Butalbital | — | — | Niacin |
| 338 | Oxycodone | Acetaminophen | Promethazine | — | Modafinil | Naltrexone | — |
| 339 | Oxycodone | Acetaminophen | Promethazine | — | Caffeine | Naltrexone | — |
| 340 | Oxycodone | Acetaminophen | Promethazine | — | Modafinil | — | Niacin |
| 341 | Oxycodone | Acetaminophen | Promethazine | — | Caffeine | — | Niacin |
| 342 | Oxycodone | Acetaminophen | Promethazine | — | — | Naltrexone | Niacin |
| 343 | Oxycodone | Acetaminophen | — | Butalbital | Modafinil | Naltrexone | — |
| 344 | Oxycodone | Acetaminophen | — | Butalbital | Caffeine | Naltrexone | — |
| 345 | Oxycodone | Acetaminophen | — | Butalbital | Modafinil | — | Niacin |
| 346 | Oxycodone | Acetaminophen | — | Butalbital | Caffeine | — | Niacin |
| 347 | Oxycodone | Acetaminophen | — | Butalbital | — | Naltrexone | Niacin |
| 348 | Oxycodone | Acetaminophen | — | — | Modafinil | Naltrexone | Niacin |
| 349 | Oxycodone | Acetaminophen | — | — | Caffeine | Naltrexone | Niacin |
| 350 | Oxycodone | — | Promethazine | Butalbital | Modafinil | Naltrexone | — |
| 351 | Oxycodone | — | Promethazine | Butalbital | Caffeine | Naltrexone | — |
| 352 | Oxycodone | — | Promethazine | Butalbital | Modafinil | — | Niacin |
| 353 | Oxycodone | — | Promethazine | Butalbital | Caffeine | — | Niacin |
| 354 | Oxycodone | — | Promethazine | Butalbital | — | Naltrexone | Niacin |
| 355 | Oxycodone | — | — | Butalbital | Caffeine | Naltrexone | Niacin |
| 356 | Oxycodone | Acetaminophen | Promethazine | Butalbital | Modafinil | Naltrexone | — |
| 357 | Oxycodone | Acetaminophen | Promethazine | Butalbital | Caffeine | Naltrexone | — |
| 358 | Oxycodone | Acetaminophen | Promethazine | Butalbital | Modafinil | — | Niacin |
| 359 | Oxycodone | Acetaminophen | Promethazine | Butalbital | Caffeine | — | Niacin |
| 360 | Oxycodone | — | Promethazine | Butalbital | Modafinil | Naltrexone | Niacin |
| 361 | Oxycodone | — | Promethazine | Butalbital | Caffeine | Naltrexone | Niacin |
| 362 | Oxycodone | Acetaminophen | — | Butalbital | Modafinil | Naltrexone | Niacin |
| 363 | Oxycodone | Acetaminophen | — | Butalbital | Caffeine | Naltrexone | Niacin |
| 364 | Oxycodone | Acetaminophen | Promethazine | — | Modafinil | Naltrexone | Niacin |
| 365 | Oxycodone | Acetaminophen | Promethazine | — | Caffeine | Naltrexone | Niacin |
| 366 | Oxycodone | Acetaminophen | Promethazine | Butalbital | — | Naltrexone | Niacin |
| 367 | Oxycodone | Acetaminophen | Promethazine | Butalbital | Modafinil | Naltrexone | Niacin |
| 368 | Oxycodone | Acetaminophen | Promethazine | Butalbital | Caffeine | Naltrexone | Niacin |
| 369 | Oxycodone | Naproxen | — | — | — | — | — |
| 370 | Oxycodone | — | Promethazine | — | — | — | — |
| 371 | Oxycodone | — | — | Butalbital | — | — | — |
| 372 | Oxycodone | — | — | — | Modafinil | — | — |
| 373 | Oxycodone | — | — | — | Caffeine | — | — |
| 374 | Oxycodone | — | — | — | — | Naltrexone | — |
| 375 | Oxycodone | — | — | — | — | — | Niacin |
| 376 | Oxycodone | Naproxen | Promethazine | — | — | — | — |
| 377 | Oxycodone | Naproxen | — | Butalbital | — | — | — |

TABLE 1-continued

Multi-drug Compositions

| Composition No. | Opioid agent | Non-opioid agent | Antiemetic agent | Barbiturate agent | Stimulant agent | Opioid antagonist agent | Abuse deterrent agent |
|---|---|---|---|---|---|---|---|
| 378 | Oxycodone | Naproxen | — | — | Modafinil | — | — |
| 379 | Oxycodone | Naproxen | — | — | Caffeine | — | — |
| 380 | Oxycodone | Naproxen | — | — | — | Naltrexone | — |
| 381 | Oxycodone | Naproxen | — | — | — | — | Niacin |
| 382 | Oxycodone | — | Promethazine | Butalbital | — | — | — |
| 383 | Oxycodone | — | Promethazine | — | Modafinil | — | — |
| 384 | Oxycodone | — | Promethazine | — | Caffeine | — | — |
| 385 | Oxycodone | — | Promethazine | — | — | Naltrexone | — |
| 386 | Oxycodone | — | Promethazine | — | — | — | Niacin |
| 387 | Oxycodone | — | — | Butalbital | Modafinil | — | — |
| 388 | Oxycodone | — | — | Butalbital | Caffeine | — | — |
| 389 | Oxycodone | — | — | Butalbital | — | Naltrexone | — |
| 390 | Oxycodone | — | — | Butalbital | — | — | Niacin |
| 391 | Oxycodone | — | — | — | Modafinil | Naltrexone | — |
| 392 | Oxycodone | — | — | — | Caffeine | Naltrexone | — |
| 393 | Oxycodone | — | — | — | Modafinil | — | Niacin |
| 394 | Oxycodone | — | — | — | Caffeine | — | Niacin |
| 395 | Oxycodone | — | — | — | — | Naltrexone | Niacin |
| 396 | Oxycodone | Naproxen | Promethazine | Butalbital | — | — | — |
| 397 | Oxycodone | Naproxen | Promethazine | — | Modafinil | — | — |
| 398 | Oxycodone | Naproxen | Promethazine | — | Caffeine | — | — |
| 399 | Oxycodone | Naproxen | Promethazine | — | — | Naltrexone | — |
| 400 | Oxycodone | Naproxen | Promethazine | — | — | — | Niacin |
| 401 | Oxycodone | Naproxen | — | Butalbital | Modafinil | — | — |
| 402 | Oxycodone | Naproxen | — | Butalbital | Caffeine | — | — |
| 403 | Oxycodone | Naproxen | — | Butalbital | — | Naltrexone | — |
| 404 | Oxycodone | Naproxen | — | Butalbital | — | — | Niacin |
| 405 | Oxycodone | Naproxen | — | — | Modafinil | Naltrexone | — |
| 406 | Oxycodone | Naproxen | — | — | Modafinil | — | Niacin |
| 407 | Oxycodone | Naproxen | — | — | Caffeine | Naltrexone | — |
| 408 | Oxycodone | Naproxen | — | — | Caffeine | — | Niacin |
| 409 | Oxycodone | Naproxen | — | — | — | Naltrexone | Niacin |
| 410 | Oxycodone | — | Promethazine | Butalbital | Modafinil | — | — |
| 411 | Oxycodone | — | Promethazine | Butalbital | Caffeine | — | — |
| 412 | Oxycodone | — | Promethazine | Butalbital | — | Naltrexone | — |
| 413 | Oxycodone | — | Promethazine | Butalbital | — | — | Niacin |
| 414 | Oxycodone | — | Promethazine | — | Modafinil | Naltrexone | — |
| 415 | Oxycodone | — | Promethazine | — | Caffeine | Naltrexone | — |
| 416 | Oxycodone | — | Promethazine | — | Modafinil | — | Niacin |
| 417 | Oxycodone | — | Promethazine | — | Caffeine | — | Niacin |
| 418 | Oxycodone | — | Promethazine | — | — | Naltrexone | Niacin |
| 419 | Oxycodone | — | — | Butalbital | Modafinil | Naltrexone | — |
| 420 | Oxycodone | — | — | Butalbital | Caffeine | Naltrexone | — |
| 421 | Oxycodone | — | — | Butalbital | Modafinil | — | Niacin |
| 422 | Oxycodone | — | — | Butalbital | Caffeine | — | Niacin |
| 423 | Oxycodone | — | — | Butalbital | — | Naltrexone | Niacin |
| 424 | Oxycodone | — | — | — | Modafinil | Naltrexone | Niacin |
| 425 | Oxycodone | — | — | — | Caffeine | Naltrexone | Niacin |
| 426 | Oxycodone | Naproxen | Promethazine | Butalbital | Modafinil | — | — |
| 427 | Oxycodone | Naproxen | Promethazine | Butalbital | Caffeine | — | — |
| 428 | Oxycodone | Naproxen | Promethazine | Butalbital | — | Naltrexone | — |
| 429 | Oxycodone | Naproxen | Promethazine | Butalbital | — | — | Niacin |
| 430 | Oxycodone | Naproxen | Promethazine | — | Modafinil | Naltrexone | — |
| 431 | Oxycodone | Naproxen | Promethazine | — | Caffeine | Naltrexone | — |
| 432 | Oxycodone | Naproxen | Promethazine | — | Modafinil | — | Niacin |
| 433 | Oxycodone | Naproxen | Promethazine | — | Caffeine | — | Niacin |
| 434 | Oxycodone | Naproxen | Promethazine | — | — | Naltrexone | Niacin |
| 435 | Oxycodone | Naproxen | — | Butalbital | Modafinil | Naltrexone | — |
| 436 | Oxycodone | Naproxen | — | Butalbital | Caffeine | Naltrexone | — |
| 437 | Oxycodone | Naproxen | — | Butalbital | Modafinil | — | Niacin |
| 438 | Oxycodone | Naproxen | — | Butalbital | Caffeine | — | Niacin |
| 439 | Oxycodone | Naproxen | — | Butalbital | — | Naltrexone | Niacin |
| 440 | Oxycodone | Naproxen | — | — | Modafinil | Naltrexone | Niacin |
| 441 | Oxycodone | Naproxen | — | — | Caffeine | Naltrexone | Niacin |
| 442 | Oxycodone | — | Promethazine | Butalbital | Modafinil | Naltrexone | — |
| 443 | Oxycodone | — | Promethazine | Butalbital | Caffeine | Naltrexone | — |
| 444 | Oxycodone | — | Promethazine | Butalbital | Modafinil | — | Niacin |
| 445 | Oxycodone | — | Promethazine | Butalbital | Caffeine | — | Niacin |
| 446 | Oxycodone | — | Promethazine | Butalbital | — | Naltrexone | Niacin |
| 447 | Oxycodone | — | — | Butalbital | Caffeine | Naltrexone | Niacin |
| 448 | Oxycodone | Naproxen | Promethazine | Butalbital | Modafinil | Naltrexone | — |
| 449 | Oxycodone | Naproxen | Promethazine | Butalbital | Caffeine | Naltrexone | — |
| 450 | Oxycodone | Naproxen | Promethazine | Butalbital | Modafinil | — | Niacin |
| 451 | Oxycodone | Naproxen | Promethazine | Butalbital | Caffeine | — | Niacin |

TABLE 1-continued

Multi-drug Compositions

| Composition No. | Opioid agent | Non-opioid agent | Antiemetic agent | Barbiturate agent | Stimulant agent | Opioid antagonist agent | Abuse deterrent agent |
|---|---|---|---|---|---|---|---|
| 452 | Oxycodone | — | Promethazine | Butalbital | Modafinil | Naltrexone | Niacin |
| 453 | Oxycodone | — | Promethazine | Butalbital | Caffeine | Naltrexone | Niacin |
| 454 | Oxycodone | Naproxen | — | Butalbital | Modafinil | Naltrexone | Niacin |
| 455 | Oxycodone | Naproxen | — | Butalbital | Caffeine | Naltrexone | Niacin |
| 456 | Oxycodone | Naproxen | Promethazine | — | Modafinil | Naltrexone | Niacin |
| 457 | Oxycodone | Naproxen | Promethazine | — | Caffeine | Naltrexone | Niacin |
| 458 | Oxycodone | Naproxen | Promethazine | Butalbital | — | Naltrexone | Niacin |
| 459 | Oxycodone | Naproxen | Promethazine | Butalbital | Modafinil | Naltrexone | Niacin |
| 460 | Oxycodone | Naproxen | Promethazine | Butalbital | Caffeine | Naltrexone | Niacin |
| 461 | Oxycodone | Ibuprofen | — | — | — | — | — |
| 462 | Oxycodone | — | Promethazine | — | — | — | — |
| 463 | Oxycodone | — | — | Butalbital | — | — | — |
| 464 | Oxycodone | — | — | — | Modafinil | — | — |
| 465 | Oxycodone | — | — | — | Caffeine | — | — |
| 466 | Oxycodone | — | — | — | — | Naltrexone | — |
| 467 | Oxycodone | — | — | — | — | — | Niacin |
| 468 | Oxycodone | Ibuprofen | Promethazine | — | — | — | — |
| 469 | Oxycodone | Ibuprofen | — | Butalbital | — | — | — |
| 470 | Oxycodone | Ibuprofen | — | — | Modafinil | — | — |
| 471 | Oxycodone | Ibuprofen | — | — | Caffeine | — | — |
| 472 | Oxycodone | Ibuprofen | — | — | — | Naltrexone | — |
| 473 | Oxycodone | Ibuprofen | — | — | — | — | Niacin |
| 474 | Oxycodone | — | Promethazine | Butalbital | — | — | — |
| 475 | Oxycodone | — | Promethazine | — | Modafinil | — | — |
| 476 | Oxycodone | — | Promethazine | — | Caffeine | — | — |
| 477 | Oxycodone | — | Promethazine | — | — | Naltrexone | — |
| 478 | Oxycodone | — | Promethazine | — | — | — | Niacin |
| 479 | Oxycodone | — | — | Butalbital | Modafinil | — | — |
| 480 | Oxycodone | — | — | Butalbital | Caffeine | — | — |
| 481 | Oxycodone | — | — | Butalbital | — | Naltrexone | — |
| 482 | Oxycodone | — | — | Butalbital | — | — | Niacin |
| 483 | Oxycodone | — | — | — | Modafinil | Naltrexone | — |
| 484 | Oxycodone | — | — | — | Caffeine | Naltrexone | — |
| 485 | Oxycodone | — | — | — | Modafinil | — | Niacin |
| 486 | Oxycodone | — | — | — | Caffeine | — | Niacin |
| 487 | Oxycodone | — | — | — | — | Naltrexone | Niacin |
| 488 | Oxycodone | Ibuprofen | Promethazine | Butalbital | — | — | — |
| 489 | Oxycodone | Ibuprofen | Promethazine | — | Modafinil | — | — |
| 490 | Oxycodone | Ibuprofen | Promethazine | — | Caffeine | — | — |
| 491 | Oxycodone | Ibuprofen | Promethazine | — | — | Naltrexone | — |
| 492 | Oxycodone | Ibuprofen | Promethazine | — | — | — | Niacin |
| 493 | Oxycodone | Ibuprofen | — | Butalbital | Modafinil | — | — |
| 494 | Oxycodone | Ibuprofen | — | Butalbital | Caffeine | — | — |
| 495 | Oxycodone | Ibuprofen | — | Butalbital | — | Naltrexone | — |
| 496 | Oxycodone | Ibuprofen | — | Butalbital | — | — | Niacin |
| 497 | Oxycodone | Ibuprofen | — | — | Modafinil | Naltrexone | — |
| 498 | Oxycodone | Ibuprofen | — | — | Modafinil | — | Niacin |
| 499 | Oxycodone | Ibuprofen | — | — | Caffeine | Naltrexone | — |
| 500 | Oxycodone | Ibuprofen | — | — | Caffeine | — | Niacin |
| 501 | Oxycodone | Ibuprofen | — | — | — | Naltrexone | Niacin |
| 502 | Oxycodone | — | Promethazine | Butalbital | Modafinil | — | — |
| 503 | Oxycodone | — | Promethazine | Butalbital | Caffeine | — | — |
| 504 | Oxycodone | — | Promethazine | Butalbital | — | Naltrexone | — |
| 505 | Oxycodone | — | Promethazine | Butalbital | — | — | Niacin |
| 506 | Oxycodone | — | Promethazine | — | Modafinil | Naltrexone | — |
| 507 | Oxycodone | — | Promethazine | — | Caffeine | Naltrexone | — |
| 508 | Oxycodone | — | Promethazine | — | Modafinil | — | Niacin |
| 509 | Oxycodone | — | Promethazine | — | Caffeine | — | Niacin |
| 510 | Oxycodone | — | Promethazine | — | — | Naltrexone | Niacin |
| 511 | Oxycodone | — | — | Butalbital | Modafinil | Naltrexone | — |
| 512 | Oxycodone | — | — | Butalbital | Caffeine | Naltrexone | — |
| 513 | Oxycodone | — | — | Butalbital | Modafinil | — | Niacin |
| 514 | Oxycodone | — | — | Butalbital | Caffeine | — | Niacin |
| 515 | Oxycodone | — | — | Butalbital | — | Naltrexone | Niacin |
| 516 | Oxycodone | — | — | — | Modafinil | Naltrexone | Niacin |
| 517 | Oxycodone | — | — | — | Caffeine | Naltrexone | Niacin |
| 518 | Oxycodone | Ibuprofen | Promethazine | Butalbital | Modafinil | — | — |
| 519 | Oxycodone | Ibuprofen | Promethazine | Butalbital | Caffeine | — | — |
| 520 | Oxycodone | Ibuprofen | Promethazine | Butalbital | — | Naltrexone | — |
| 521 | Oxycodone | Ibuprofen | Promethazine | Butalbital | — | — | Niacin |
| 522 | Oxycodone | Ibuprofen | Promethazine | — | Modafinil | Naltrexone | — |
| 523 | Oxycodone | Ibuprofen | Promethazine | — | Caffeine | Naltrexone | — |
| 524 | Oxycodone | Ibuprofen | Promethazine | — | Modafinil | — | Niacin |
| 525 | Oxycodone | Ibuprofen | Promethazine | — | Caffeine | — | Niacin |

TABLE 1-continued

Multi-drug Compositions

| Composition No. | Opioid agent | Non-opioid agent | Antiemetic agent | Barbiturate agent | Stimulant agent | Opioid antagonist agent | Abuse deterrent agent |
|---|---|---|---|---|---|---|---|
| 526 | Oxycodone | Ibuprofen | Promethazine | — | — | Naltrexone | Niacin |
| 527 | Oxycodone | Ibuprofen | — | Butalbital | Modafinil | Naltrexone | — |
| 528 | Oxycodone | Ibuprofen | — | Butalbital | Caffeine | Naltrexone | — |
| 529 | Oxycodone | Ibuprofen | — | Butalbital | Modafinil | — | Niacin |
| 530 | Oxycodone | Ibuprofen | — | Butalbital | Caffeine | — | Niacin |
| 531 | Oxycodone | Ibuprofen | — | Butalbital | — | Naltrexone | Niacin |
| 532 | Oxycodone | Ibuprofen | — | — | Modafinil | Naltrexone | Niacin |
| 533 | Oxycodone | Ibuprofen | — | — | Caffeine | Naltrexone | Niacin |
| 534 | Oxycodone | — | Promethazine | Butalbital | Modafinil | Naltrexone | — |
| 535 | Oxycodone | — | Promethazine | Butalbital | Caffeine | Naltrexone | — |
| 536 | Oxycodone | — | Promethazine | Butalbital | Modafinil | — | Niacin |
| 537 | Oxycodone | — | Promethazine | Butalbital | Caffeine | — | Niacin |
| 538 | Oxycodone | — | Promethazine | Butalbital | — | Naltrexone | Niacin |
| 539 | Oxycodone | — | — | Butalbital | Caffeine | Naltrexone | Niacin |
| 540 | Oxycodone | Ibuprofen | Promethazine | Butalbital | Modafinil | Naltrexone | — |
| 541 | Oxycodone | Ibuprofen | Promethazine | Butalbital | Caffeine | Naltrexone | — |
| 542 | Oxycodone | Ibuprofen | Promethazine | Butalbital | Modafinil | — | Niacin |
| 543 | Oxycodone | Ibuprofen | Promethazine | Butalbital | Caffeine | — | Niacin |
| 544 | Oxycodone | — | Promethazine | Butalbital | Modafinil | Naltrexone | Niacin |
| 545 | Oxycodone | — | Promethazine | Butalbital | Caffeine | Naltrexone | Niacin |
| 546 | Oxycodone | Ibuprofen | — | Butalbital | Modafinil | Naltrexone | Niacin |
| 547 | Oxycodone | Ibuprofen | — | Butalbital | Caffeine | Naltrexone | Niacin |
| 548 | Oxycodone | Ibuprofen | Promethazine | — | Modafinil | Naltrexone | Niacin |
| 549 | Oxycodone | Ibuprofen | Promethazine | — | Caffeine | Naltrexone | Niacin |
| 550 | Oxycodone | Ibuprofen | Promethazine | Butalbital | — | Naltrexone | Niacin |
| 551 | Oxycodone | Ibuprofen | Promethazine | Butalbital | Modafinil | Naltrexone | Niacin |
| 552 | Oxycodone | Ibuprofen | Promethazine | Butalbital | Caffeine | Naltrexone | Niacin |
| 553 | Propoxyphene | Acetaminophen | — | — | — | — | — |
| 554 | Propoxyphene | — | Promethazine | — | — | — | — |
| 555 | Propoxyphene | — | — | Butalbital | — | — | — |
| 556 | Propoxyphene | — | — | — | Modafinil | — | — |
| 557 | Propoxyphene | — | — | — | Caffeine | — | — |
| 558 | Propoxyphene | — | — | — | — | Naltrexone | — |
| 559 | Propoxyphene | — | — | — | — | — | Niacin |
| 560 | Propoxyphene | Acetaminophen | Promethazine | — | — | — | — |
| 561 | Propoxyphene | Acetaminophen | — | Butalbital | — | — | — |
| 562 | Propoxyphene | Acetaminophen | — | — | Modafinil | — | — |
| 563 | Propoxyphene | Acetaminophen | — | — | Caffeine | — | — |
| 564 | Propoxyphene | Acetaminophen | — | — | — | Naltrexone | — |
| 565 | Propoxyphene | Acetaminophen | — | — | — | — | Niacin |
| 566 | Propoxyphene | — | Promethazine | Butalbital | — | — | — |
| 567 | Propoxyphene | — | Promethazine | — | Modafinil | — | — |
| 568 | Propoxyphene | — | Promethazine | — | Caffeine | — | — |
| 569 | Propoxyphene | — | Promethazine | — | — | Naltrexone | — |
| 570 | Propoxyphene | — | Promethazine | — | — | — | Niacin |
| 571 | Propoxyphene | — | — | Butalbital | Modafinil | — | — |
| 572 | Propoxyphene | — | — | Butalbital | Caffeine | — | — |
| 573 | Propoxyphene | — | — | Butalbital | — | Naltrexone | — |
| 574 | Propoxyphene | — | — | Butalbital | — | — | Niacin |
| 575 | Propoxyphene | — | — | — | Modafinil | Naltrexone | — |
| 576 | Propoxyphene | — | — | — | Caffeine | Naltrexone | — |
| 577 | Propoxyphene | — | — | — | Modafinil | — | Niacin |
| 578 | Propoxyphene | — | — | — | Caffeine | — | Niacin |
| 579 | Propoxyphene | — | — | — | — | Naltrexone | Niacin |
| 580 | Propoxyphene | Acetaminophen | Promethazine | Butalbital | — | — | — |
| 581 | Propoxyphene | Acetaminophen | Promethazine | — | Modafinil | — | — |
| 582 | Propoxyphene | Acetaminophen | Promethazine | — | Caffeine | — | — |
| 583 | Propoxyphene | Acetaminophen | Promethazine | — | — | Naltrexone | — |
| 584 | Propoxyphene | Acetaminophen | Promethazine | — | — | — | Niacin |
| 585 | Propoxyphene | Acetaminophen | — | Butalbital | Modafinil | — | — |
| 586 | Propoxyphene | Acetaminophen | — | Butalbital | Caffeine | — | — |
| 587 | Propoxyphene | Acetaminophen | — | Butalbital | — | Naltrexone | — |
| 588 | Propoxyphene | Acetaminophen | — | Butalbital | — | — | Niacin |
| 589 | Propoxyphene | Acetaminophen | — | — | Modafinil | Naltrexone | — |
| 590 | Propoxyphene | Acetaminophen | — | — | Modafinil | — | Niacin |
| 591 | Propoxyphene | Acetaminophen | — | — | Caffeine | Naltrexone | — |
| 592 | Propoxyphene | Acetaminophen | — | — | Caffeine | — | Niacin |
| 593 | Propoxyphene | Acetaminophen | — | — | — | Naltrexone | Niacin |
| 594 | Propoxyphene | — | Promethazine | Butalbital | Modafinil | — | — |
| 595 | Propoxyphene | — | Promethazine | Butalbital | Caffeine | — | — |
| 596 | Propoxyphene | — | Promethazine | Butalbital | — | Naltrexone | — |
| 597 | Propoxyphene | — | Promethazine | Butalbital | — | — | Niacin |
| 598 | Propoxyphene | — | Promethazine | — | Modafinil | Naltrexone | — |
| 599 | Propoxyphene | — | Promethazine | — | Caffeine | Naltrexone | — |

TABLE 1-continued

Multi-drug Compositions

| Composition No. | Opioid agent | Non-opioid agent | Antiemetic agent | Barbiturate agent | Stimulant agent | Opioid antagonist agent | Abuse deterrent agent |
|---|---|---|---|---|---|---|---|
| 600 | Propoxyphene | — | Promethazine | — | Modafinil | — | Niacin |
| 601 | Propoxyphene | — | Promethazine | — | Caffeine | — | Niacin |
| 602 | Propoxyphene | — | Promethazine | — | — | Naltrexone | Niacin |
| 603 | Propoxyphene | — | — | Butalbital | Modafinil | Naltrexone | — |
| 604 | Propoxyphene | — | — | Butalbital | Caffeine | Naltrexone | — |
| 605 | Propoxyphene | — | — | Butalbital | Modafinil | — | Niacin |
| 606 | Propoxyphene | — | — | Butalbital | Caffeine | — | Niacin |
| 607 | Propoxyphene | — | — | Butalbital | — | Naltrexone | Niacin |
| 608 | Propoxyphene | — | — | — | Modafinil | Naltrexone | Niacin |
| 609 | Propoxyphene | — | — | — | Caffeine | Naltrexone | Niacin |
| 610 | Propoxyphene | Acetaminophen | Promethazine | Butalbital | Modafinil | — | — |
| 611 | Propoxyphene | Acetaminophen | Promethazine | Butalbital | Caffeine | — | — |
| 612 | Propoxyphene | Acetaminophen | Promethazine | Butalbital | — | Naltrexone | — |
| 613 | Propoxyphene | Acetaminophen | Promethazine | Butalbital | — | — | Niacin |
| 614 | Propoxyphene | Acetaminophen | Promethazine | — | Modafinil | Naltrexone | — |
| 615 | Propoxyphene | Acetaminophen | Promethazine | — | Caffeine | Naltrexone | — |
| 616 | Propoxyphene | Acetaminophen | Promethazine | — | Modafinil | — | Niacin |
| 617 | Propoxyphene | Acetaminophen | Promethazine | — | Caffeine | — | Niacin |
| 618 | Propoxyphene | Acetaminophen | Promethazine | — | — | Naltrexone | Niacin |
| 619 | Propoxyphene | Acetaminophen | — | Butalbital | Modafinil | Naltrexone | — |
| 620 | Propoxyphene | Acetaminophen | — | Butalbital | Caffeine | Naltrexone | — |
| 621 | Propoxyphene | Acetaminophen | — | Butalbital | Modafinil | — | Niacin |
| 622 | Propoxyphene | Acetaminophen | — | Butalbital | Caffeine | — | Niacin |
| 623 | Propoxyphene | Acetaminophen | — | Butalbital | — | Naltrexone | Niacin |
| 624 | Propoxyphene | Acetaminophen | — | — | Modafinil | Naltrexone | Niacin |
| 625 | Propoxyphene | Acetaminophen | — | — | Caffeine | Naltrexone | Niacin |
| 626 | Propoxyphene | — | Promethazine | Butalbital | Modafinil | Naltrexone | — |
| 627 | Propoxyphene | — | Promethazine | Butalbital | Caffeine | Naltrexone | — |
| 628 | Propoxyphene | — | Promethazine | Butalbital | Modafinil | — | Niacin |
| 629 | Propoxyphene | — | Promethazine | Butalbital | Caffeine | — | Niacin |
| 630 | Propoxyphene | — | Promethazine | Butalbital | — | Naltrexone | Niacin |
| 631 | Propoxyphene | — | — | Butalbital | Caffeine | Naltrexone | Niacin |
| 632 | Propoxyphene | Acetaminophen | Promethazine | Butalbital | Modafinil | Naltrexone | — |
| 633 | Propoxyphene | Acetaminophen | Promethazine | Butalbital | Caffeine | Naltrexone | — |
| 634 | Propoxyphene | Acetaminophen | Promethazine | Butalbital | Modafinil | — | Niacin |
| 635 | Propoxyphene | Acetaminophen | Promethazine | Butalbital | Caffeine | — | Niacin |
| 636 | Propoxyphene | — | Promethazine | Butalbital | Modafinil | Naltrexone | Niacin |
| 637 | Propoxyphene | — | Promethazine | Butalbital | Caffeine | Naltrexone | Niacin |
| 638 | Propoxyphene | Acetaminophen | — | Butalbital | Modafinil | Naltrexone | Niacin |
| 639 | Propoxyphene | Acetaminophen | — | Butalbital | Caffeine | Naltrexone | Niacin |
| 640 | Propoxyphene | Acetaminophen | Promethazine | — | Modafinil | Naltrexone | Niacin |
| 641 | Propoxyphene | Acetaminophen | Promethazine | — | Caffeine | Naltrexone | Niacin |
| 642 | Propoxyphene | Acetaminophen | Promethazine | Butalbital | — | Naltrexone | Niacin |
| 643 | Propoxyphene | Acetaminophen | Promethazine | Butalbital | Modafinil | Naltrexone | Niacin |
| 644 | Propoxyphene | Acetaminophen | Promethazine | Butalbital | Caffeine | Naltrexone | Niacin |
| 645 | Propoxyphene | Naproxen | — | — | — | — | — |
| 646 | Propoxyphene | — | Promethazine | — | — | — | — |
| 647 | Propoxyphene | — | — | Butalbital | — | — | — |
| 648 | Propoxyphene | — | — | — | Modafinil | — | — |
| 649 | Propoxyphene | — | — | — | Caffeine | — | — |
| 650 | Propoxyphene | — | — | — | — | Naltrexone | — |
| 651 | Propoxyphene | — | — | — | — | — | Niacin |
| 652 | Propoxyphene | Naproxen | Promethazine | — | — | — | — |
| 653 | Propoxyphene | Naproxen | — | Butalbital | — | — | — |
| 654 | Propoxyphene | Naproxen | — | — | Modafinil | — | — |
| 655 | Propoxyphene | Naproxen | — | — | Caffeine | — | — |
| 656 | Propoxyphene | Naproxen | — | — | — | Naltrexone | — |
| 657 | Propoxyphene | Naproxen | — | — | — | — | Niacin |
| 658 | Propoxyphene | — | Promethazine | Butalbital | — | — | — |
| 659 | Propoxyphene | — | Promethazine | — | Modafinil | — | — |
| 660 | Propoxyphene | — | Promethazine | — | Caffeine | — | — |
| 661 | Propoxyphene | — | Promethazine | — | — | Naltrexone | — |
| 662 | Propoxyphene | — | Promethazine | — | — | — | Niacin |
| 663 | Propoxyphene | — | — | Butalbital | Modafinil | — | — |
| 664 | Propoxyphene | — | — | Butalbital | Caffeine | — | — |
| 665 | Propoxyphene | — | — | Butalbital | — | Naltrexone | — |
| 666 | Propoxyphene | — | — | Butalbital | — | — | Niacin |
| 667 | Propoxyphene | — | — | — | Modafinil | Naltrexone | — |
| 668 | Propoxyphene | — | — | — | Caffeine | Naltrexone | — |
| 669 | Propoxyphene | — | — | — | Modafinil | — | Niacin |
| 670 | Propoxyphene | — | — | — | Caffeine | — | Niacin |
| 671 | Propoxyphene | — | — | — | — | Naltrexone | Niacin |
| 672 | Propoxyphene | Naproxen | Promethazine | Butalbital | — | — | — |
| 673 | Propoxyphene | Naproxen | Promethazine | — | Modafinil | — | — |

TABLE 1-continued

Multi-drug Compositions

| Composition No. | Opioid agent | Non-opioid agent | Antiemetic agent | Barbiturate agent | Stimulant agent | Opioid antagonist agent | Abuse deterrent agent |
|---|---|---|---|---|---|---|---|
| 674 | Propoxyphene | Naproxen | Promethazine | — | Caffeine | — | — |
| 675 | Propoxyphene | Naproxen | Promethazine | — | — | Naltrexone | — |
| 676 | Propoxyphene | Naproxen | Promethazine | — | — | — | Niacin |
| 677 | Propoxyphene | Naproxen | — | Butalbital | Modafinil | — | — |
| 678 | Propoxyphene | Naproxen | — | Butalbital | Caffeine | — | — |
| 679 | Propoxyphene | Naproxen | — | Butalbital | — | Naltrexone | — |
| 680 | Propoxyphene | Naproxen | — | Butalbital | — | — | Niacin |
| 681 | Propoxyphene | Naproxen | — | — | Modafinil | Naltrexone | — |
| 682 | Propoxyphene | Naproxen | — | — | Modafinil | — | Niacin |
| 683 | Propoxyphene | Naproxen | — | — | Caffeine | Naltrexone | — |
| 684 | Propoxyphene | Naproxen | — | — | Caffeine | — | Niacin |
| 685 | Propoxyphene | Naproxen | — | — | — | Naltrexone | Niacin |
| 686 | Propoxyphene | — | Promethazine | Butalbital | Modafinil | — | — |
| 687 | Propoxyphene | — | Promethazine | Butalbital | Caffeine | — | — |
| 688 | Propoxyphene | — | Promethazine | Butalbital | — | Naltrexone | — |
| 689 | Propoxyphene | — | Promethazine | Butalbital | — | — | Niacin |
| 690 | Propoxyphene | — | Promethazine | — | Modafinil | Naltrexone | — |
| 691 | Propoxyphene | — | Promethazine | — | Caffeine | Naltrexone | — |
| 692 | Propoxyphene | — | Promethazine | — | Modafinil | — | Niacin |
| 693 | Propoxyphene | — | Promethazine | — | Caffeine | — | Niacin |
| 694 | Propoxyphene | — | Promethazine | — | — | Naltrexone | Niacin |
| 695 | Propoxyphene | — | — | Butalbital | Modafinil | Naltrexone | — |
| 696 | Propoxyphene | — | — | Butalbital | Caffeine | Naltrexone | — |
| 697 | Propoxyphene | — | — | Butalbital | Modafinil | — | Niacin |
| 698 | Propoxyphene | — | — | Butalbital | Caffeine | — | Niacin |
| 699 | Propoxyphene | — | — | Butalbital | — | Naltrexone | Niacin |
| 700 | Propoxyphene | — | — | — | Modafinil | Naltrexone | Niacin |
| 701 | Propoxyphene | — | — | — | Caffeine | Naltrexone | Niacin |
| 702 | Propoxyphene | Naproxen | Promethazine | Butalbital | Modafinil | — | — |
| 703 | Propoxyphene | Naproxen | Promethazine | Butalbital | Caffeine | — | — |
| 704 | Propoxyphene | Naproxen | Promethazine | Butalbital | — | Naltrexone | — |
| 705 | Propoxyphene | Naproxen | Promethazine | Butalbital | — | — | Niacin |
| 706 | Propoxyphene | Naproxen | Promethazine | — | Modafinil | Naltrexone | — |
| 707 | Propoxyphene | Naproxen | Promethazine | — | Caffeine | Naltrexone | — |
| 708 | Propoxyphene | Naproxen | Promethazine | — | Modafinil | — | Niacin |
| 709 | Propoxyphene | Naproxen | Promethazine | — | Caffeine | — | Niacin |
| 710 | Propoxyphene | Naproxen | Promethazine | — | — | Naltrexone | Niacin |
| 711 | Propoxyphene | Naproxen | — | Butalbital | Modafinil | Naltrexone | — |
| 712 | Propoxyphene | Naproxen | — | Butalbital | Caffeine | Naltrexone | — |
| 713 | Propoxyphene | Naproxen | — | Butalbital | Modafinil | — | Niacin |
| 714 | Propoxyphene | Naproxen | — | Butalbital | Caffeine | — | Niacin |
| 715 | Propoxyphene | Naproxen | — | Butalbital | — | Naltrexone | Niacin |
| 716 | Propoxyphene | Naproxen | — | — | Modafinil | Naltrexone | Niacin |
| 717 | Propoxyphene | Naproxen | — | — | Caffeine | Naltrexone | Niacin |
| 718 | Propoxyphene | — | Promethazine | Butalbital | Modafinil | Naltrexone | — |
| 719 | Propoxyphene | — | Promethazine | Butalbital | Caffeine | Naltrexone | — |
| 720 | Propoxyphene | — | Promethazine | Butalbital | Modafinil | — | Niacin |
| 721 | Propoxyphene | — | Promethazine | Butalbital | Caffeine | — | Niacin |
| 722 | Propoxyphene | — | Promethazine | Butalbital | — | Naltrexone | Niacin |
| 723 | Propoxyphene | — | — | Butalbital | Caffeine | Naltrexone | Niacin |
| 724 | Propoxyphene | Naproxen | Promethazine | Butalbital | Modafinil | Naltrexone | — |
| 725 | Propoxyphene | Naproxen | Promethazine | Butalbital | Caffeine | Naltrexone | — |
| 726 | Propoxyphene | Naproxen | Promethazine | Butalbital | Modafinil | — | Niacin |
| 727 | Propoxyphene | Naproxen | Promethazine | Butalbital | Caffeine | — | Niacin |
| 728 | Propoxyphene | — | Promethazine | Butalbital | Modafinil | Naltrexone | Niacin |
| 729 | Propoxyphene | — | Promethazine | Butalbital | Caffeine | Naltrexone | Niacin |
| 730 | Propoxyphene | Naproxen | — | Butalbital | Modafinil | Naltrexone | Niacin |
| 731 | Propoxyphene | Naproxen | — | Butalbital | Caffeine | Naltrexone | Niacin |
| 732 | Propoxyphene | Naproxen | Promethazine | — | Modafinil | Naltrexone | Niacin |
| 733 | Propoxyphene | Naproxen | Promethazine | — | Caffeine | Naltrexone | Niacin |
| 734 | Propoxyphene | Naproxen | Promethazine | Butalbital | — | Naltrexone | Niacin |
| 735 | Propoxyphene | Naproxen | Promethazine | Butalbital | Modafinil | Naltrexone | Niacin |
| 736 | Propoxyphene | Naproxen | Promethazine | Butalbital | Caffeine | Naltrexone | Niacin |
| 737 | Propoxyphene | Ibuprofen | — | — | — | — | — |
| 738 | Propoxyphene | — | Promethazine | — | — | — | — |
| 739 | Propoxyphene | — | — | Butalbital | — | — | — |
| 740 | Propoxyphene | — | — | — | Modafinil | — | — |
| 741 | Propoxyphene | — | — | — | Caffeine | — | — |
| 742 | Propoxyphene | — | — | — | — | Naltrexone | — |
| 743 | Propoxyphene | — | — | — | — | — | Niacin |
| 744 | Propoxyphene | Ibuprofen | Promethazine | — | — | — | — |
| 745 | Propoxyphene | Ibuprofen | — | Butalbital | — | — | — |
| 746 | Propoxyphene | Ibuprofen | — | — | Modafinil | — | — |
| 747 | Propoxyphene | Ibuprofen | — | — | Caffeine | — | — |

TABLE 1-continued

Multi-drug Compositions

| Composition No. | Opioid agent | Non-opioid agent | Antiemetic agent | Barbiturate agent | Stimulant agent | Opioid antagonist agent | Abuse deterrent agent |
|---|---|---|---|---|---|---|---|
| 748 | Propoxyphene | Ibuprofen | — | — | — | Naltrexone | — |
| 749 | Propoxyphene | Ibuprofen | — | — | — | — | Niacin |
| 750 | Propoxyphene | — | Promethazine | Butalbital | — | — | — |
| 751 | Propoxyphene | — | Promethazine | — | Modafinil | — | — |
| 752 | Propoxyphene | — | Promethazine | — | Caffeine | — | — |
| 753 | Propoxyphene | — | Promethazine | — | — | Naltrexone | — |
| 754 | Propoxyphene | — | Promethazine | — | — | — | Niacin |
| 755 | Propoxyphene | — | — | Butalbital | Modafinil | — | — |
| 756 | Propoxyphene | — | — | Butalbital | Caffeine | — | — |
| 757 | Propoxyphene | — | — | Butalbital | — | Naltrexone | — |
| 758 | Propoxyphene | — | — | Butalbital | — | — | Niacin |
| 759 | Propoxyphene | — | — | — | Modafinil | Naltrexone | — |
| 760 | Propoxyphene | — | — | — | Caffeine | Naltrexone | — |
| 761 | Propoxyphene | — | — | — | Modafinil | — | Niacin |
| 762 | Propoxyphene | — | — | — | Caffeine | — | Niacin |
| 763 | Propoxyphene | — | — | — | — | Naltrexone | Niacin |
| 764 | Propoxyphene | Ibuprofen | Promethazine | Butalbital | — | — | — |
| 765 | Propoxyphene | Ibuprofen | Promethazine | — | Modafinil | — | — |
| 766 | Propoxyphene | Ibuprofen | Promethazine | — | Caffeine | — | — |
| 767 | Propoxyphene | Ibuprofen | Promethazine | — | — | Naltrexone | — |
| 768 | Propoxyphene | Ibuprofen | Promethazine | — | — | — | Niacin |
| 769 | Propoxyphene | Ibuprofen | — | Butalbital | Modafinil | — | — |
| 770 | Propoxyphene | Ibuprofen | — | Butalbital | Caffeine | — | — |
| 771 | Propoxyphene | Ibuprofen | — | Butalbital | — | Naltrexone | — |
| 772 | Propoxyphene | Ibuprofen | — | Butalbital | — | — | Niacin |
| 773 | Propoxyphene | Ibuprofen | — | — | Modafinil | Naltrexone | — |
| 774 | Propoxyphene | Ibuprofen | — | — | Modafinil | — | Niacin |
| 775 | Propoxyphene | Ibuprofen | — | — | Caffeine | Naltrexone | — |
| 776 | Propoxyphene | Ibuprofen | — | — | Caffeine | — | Niacin |
| 777 | Propoxyphene | Ibuprofen | — | — | — | Naltrexone | Niacin |
| 778 | Propoxyphene | — | Promethazine | Butalbital | Modafinil | — | — |
| 779 | Propoxyphene | — | Promethazine | Butalbital | Caffeine | — | — |
| 780 | Propoxyphene | — | Promethazine | Butalbital | — | Naltrexone | — |
| 781 | Propoxyphene | — | Promethazine | Butalbital | — | — | Niacin |
| 782 | Propoxyphene | — | Promethazine | — | Modafinil | Naltrexone | — |
| 783 | Propoxyphene | — | Promethazine | — | Caffeine | Naltrexone | — |
| 784 | Propoxyphene | — | Promethazine | — | Modafinil | — | Niacin |
| 785 | Propoxyphene | — | Promethazine | — | Caffeine | — | Niacin |
| 786 | Propoxyphene | — | Promethazine | — | — | Naltrexone | Niacin |
| 787 | Propoxyphene | — | — | Butalbital | Modafinil | Naltrexone | — |
| 788 | Propoxyphene | — | — | Butalbital | Caffeine | Naltrexone | — |
| 789 | Propoxyphene | — | — | Butalbital | Modafinil | — | Niacin |
| 790 | Propoxyphene | — | — | Butalbital | Caffeine | — | Niacin |
| 791 | Propoxyphene | — | — | Butalbital | — | Naltrexone | Niacin |
| 792 | Propoxyphene | — | — | — | Modafinil | Naltrexone | Niacin |
| 793 | Propoxyphene | — | — | — | Caffeine | Naltrexone | Niacin |
| 794 | Propoxyphene | Ibuprofen | Promethazine | Butalbital | Modafinil | — | — |
| 795 | Propoxyphene | Ibuprofen | Promethazine | Butalbital | Caffeine | — | — |
| 796 | Propoxyphene | Ibuprofen | Promethazine | Butalbital | — | Naltrexone | — |
| 797 | Propoxyphene | Ibuprofen | Promethazine | Butalbital | — | — | Niacin |
| 798 | Propoxyphene | Ibuprofen | Promethazine | — | Modafinil | Naltrexone | — |
| 799 | Propoxyphene | Ibuprofen | Promethazine | — | Caffeine | Naltrexone | — |
| 800 | Propoxyphene | Ibuprofen | Promethazine | — | Modafinil | — | Niacin |
| 801 | Propoxyphene | Ibuprofen | Promethazine | — | Caffeine | — | Niacin |
| 802 | Propoxyphene | Ibuprofen | Promethazine | — | — | Naltrexone | Niacin |
| 803 | Propoxyphene | Ibuprofen | — | Butalbital | Modafinil | Naltrexone | — |
| 804 | Propoxyphene | Ibuprofen | — | Butalbital | Caffeine | Naltrexone | — |
| 805 | Propoxyphene | Ibuprofen | — | Butalbital | Modafinil | — | Niacin |
| 806 | Propoxyphene | Ibuprofen | — | Butalbital | Caffeine | — | Niacin |
| 807 | Propoxyphene | Ibuprofen | — | Butalbital | — | Naltrexone | Niacin |
| 808 | Propoxyphene | Ibuprofen | — | — | Modafinil | Naltrexone | Niacin |
| 809 | Propoxyphene | Ibuprofen | — | — | Caffeine | Naltrexone | Niacin |
| 810 | Propoxyphene | — | Promethazine | Butalbital | Modafinil | Naltrexone | — |
| 811 | Propoxyphene | — | Promethazine | Butalbital | Caffeine | Naltrexone | — |
| 812 | Propoxyphene | — | Promethazine | Butalbital | Modafinil | — | Niacin |
| 813 | Propoxyphene | — | Promethazine | Butalbital | Caffeine | — | Niacin |
| 814 | Propoxyphene | — | Promethazine | Butalbital | — | Naltrexone | Niacin |
| 815 | Propoxyphene | — | — | Butalbital | Caffeine | Naltrexone | Niacin |
| 816 | Propoxyphene | Ibuprofen | Promethazine | Butalbital | Modafinil | Naltrexone | — |
| 817 | Propoxyphene | Ibuprofen | Promethazine | Butalbital | Caffeine | Naltrexone | — |
| 818 | Propoxyphene | Ibuprofen | Promethazine | Butalbital | Modafinil | — | Niacin |
| 819 | Propoxyphene | Ibuprofen | Promethazine | Butalbital | Caffeine | — | Niacin |
| 820 | Propoxyphene | — | Promethazine | Butalbital | Modafinil | Naltrexone | Niacin |
| 821 | Propoxyphene | — | Promethazine | Butalbital | Caffeine | Naltrexone | Niacin |

TABLE 1-continued

Multi-drug Compositions

| Composition No. | Opioid agent | Non-opioid agent | Antiemetic agent | Barbiturate agent | Stimulant agent | Opioid antagonist agent | Abuse deterrent agent |
|---|---|---|---|---|---|---|---|
| 822 | Propoxyphene | Ibuprofen | — | Butalbital | Modafinil | Naltrexone | Niacin |
| 823 | Propoxyphene | Ibuprofen | — | Butalbital | Caffeine | Naltrexone | Niacin |
| 824 | Propoxyphene | Ibuprofen | Promethazine | — | Modafinil | Naltrexone | Niacin |
| 825 | Propoxyphene | Ibuprofen | Promethazine | — | Caffeine | Naltrexone | Niacin |
| 826 | Propoxyphene | Ibuprofen | Promethazine | Butalbital | — | Naltrexone | Niacin |
| 827 | Propoxyphene | Ibuprofen | Promethazine | Butalbital | Modafinil | Naltrexone | Niacin |
| 828 | Propoxyphene | Ibuprofen | Promethazine | Butalbital | Caffeine | Naltrexone | Niacin |
| 829 | Propoxyphene | Ibuprofen | — | — | — | — | — |
| 830 | — | Acetaminophen | — | — | Modafinil | — | — |
| 831 | — | Acetaminophen | — | — | Caffeine | — | — |
| 832 | — | Ibuprofen | — | — | Modafinil | — | — |
| 833 | — | Ibuprofen | — | — | Caffeine | — | — |
| 834 | — | Naproxen | — | — | Modafinil | — | — |
| 835 | — | Naproxen | — | — | Caffeine | — | — |
| 836 | — | Acetaminophen | — | Butalbital | Modafinil | — | — |
| 837 | — | Acetaminophen | — | Butalbital | Caffeine | — | — |
| 838 | — | Ibuprofen | — | Butalbital | Modafinil | — | — |
| 839 | — | Ibuprofen | — | Butalbital | Caffeine | — | — |
| 840 | — | Naproxen | — | Butalbital | Modafinil | — | — |
| 841 | — | Naproxen | — | Butalbital | Caffeine | — | — |

Note:
— indicates that the respective agent is absent from a particular composition.

TABLE 2

Multi-drug Compositions

| Composition No. | Triptan | Antiemetic agent |
|---|---|---|
| 842 | naratriptan | promethazine |
| 843 | naratriptan | aprepitant |
| 844 | naratriptan | dronabinol |
| 845 | naratriptan | perphenazine |
| 846 | naratriptan | palonosetron |
| 847 | naratriptan | trimethyobenzamide |
| 848 | naratriptan | metoclopromide |
| 849 | naratriptan | domperidone |
| 850 | naratriptan | prochlorperazine |
| 851 | naratriptan | promethazine |
| 852 | naratriptan | chlorpromazine |
| 853 | naratriptan | trimethobenzamide |
| 854 | naratriptan | ondansetron |
| 855 | naratriptan | granisetron |
| 856 | naratriptan | hydroxyzine |
| 857 | naratriptan | acetylleucine |
| 858 | naratriptan | monoethanolamine |
| 859 | naratriptan | alizapride |
| 860 | naratriptan | azasetron |
| 861 | naratriptan | benzquinamide |
| 862 | naratriptan | bietanautine |
| 863 | naratriptan | bromopride |
| 864 | naratriptan | buclizine |
| 865 | naratriptan | clebopride |
| 866 | naratriptan | cyclizine |
| 867 | naratriptan | dimenhydrinate |
| 868 | naratriptan | diphenidol |
| 869 | naratriptan | dolasetron |
| 870 | naratriptan | meclizine |
| 871 | naratriptan | methallatal |
| 872 | naratriptan | metopimazine |
| 873 | naratriptan | nabilone |
| 874 | naratriptan | oxyperndyl |
| 875 | naratriptan | pipamazine |
| 876 | naratriptan | scopolamine |
| 877 | naratriptan | sulpiride |
| 878 | naratriptan | tetrahydrocannabinol |
| 879 | naratriptan | thiethylperazine |
| 880 | naratriptan | thioproperazine |
| 881 | naratriptan | tropisetron |
| 882 | naratriptan | droperidol |
| 883 | naratriptan | haloperidol |
| 884 | naratriptan | prochloperazine |
| 885 | naratriptan | metoclopramide |
| 886 | naratriptan | diphenhydramine |
| 887 | naratriptan | *cannabis* |
| 888 | naratriptan | midazolam |
| 889 | naratriptan | lorazepam |
| 890 | naratriptan | hyoscine |
| 891 | naratriptan | dexamethasone |
| 892 | naratriptan | emetrol |
| 893 | naratriptan | propofol |
| 894 | almotriptan | promethazine |
| 895 | almotriptan | aprepitant |
| 896 | almotriptan | dronabinol |
| 897 | almotriptan | perphenazine |
| 898 | almotriptan | palonosetron |
| 899 | almotriptan | trimethyobenzamide |
| 900 | almotriptan | metoclopromide |
| 901 | almotriptan | domperidone |
| 902 | almotriptan | prochlorperazine |
| 903 | almotriptan | promethazine |
| 904 | almotriptan | chlorpromazine |
| 905 | almotriptan | trimethobenzamide |
| 906 | almotriptan | ondansetron |
| 907 | almotriptan | granisetron |
| 908 | almotriptan | hydroxyzine |
| 909 | almotriptan | acetylleucine |
| 910 | almotriptan | monoethanolamine |
| 911 | almotriptan | alizapride |
| 912 | almotriptan | azasetron |
| 913 | almotriptan | benzquinamide |
| 914 | almotriptan | bietanautine |
| 915 | almotriptan | bromopride |
| 916 | almotriptan | buclizine |
| 917 | almotriptan | clebopride |
| 918 | almotriptan | cyclizine |
| 919 | almotriptan | dimenhydrinate |
| 920 | almotriptan | diphenidol |
| 921 | almotriptan | dolasetron |
| 922 | almotriptan | meclizine |
| 923 | almotriptan | methallatal |
| 924 | almotriptan | metopimazine |
| 925 | almotriptan | nabilone |

TABLE 2-continued

Multi-drug Compositions

| Composition No. | Triptan | Antiemetic agent |
|---|---|---|
| 926 | almotriptan | oxyperndyl |
| 927 | almotriptan | pipamazine |
| 928 | almotriptan | scopolamine |
| 929 | almotriptan | sulpiride |
| 930 | almotriptan | tetrahydrocannabinol |
| 931 | almotriptan | thiethylperazine |
| 932 | almotriptan | thioproperazine |
| 933 | almotriptan | tropisetron |
| 934 | almotriptan | droperidol |
| 935 | almotriptan | haloperidol |
| 936 | almotriptan | prochloperazine |
| 937 | almotriptan | metoclopramide |
| 938 | almotriptan | diphenhydramine |
| 939 | almotriptan | *cannabis* |
| 940 | almotriptan | midazolam |
| 941 | almotriptan | lorazepam |
| 942 | almotriptan | hyoscine |
| 943 | almotriptan | dexamethasone |
| 944 | almotriptan | emetrol |
| 945 | almotriptan | propofol |
| 946 | sumatriptan | promethazine |
| 947 | sumatriptan | aprepitant |
| 948 | sumatriptan | dronabinol |
| 949 | sumatriptan | perphenazine |
| 950 | sumatriptan | palonosetron |
| 951 | sumatriptan | trimethyobenzamide |
| 952 | sumatriptan | metoclopromide |
| 953 | sumatriptan | domperidone |
| 954 | sumatriptan | prochlorperazine |
| 955 | sumatriptan | promethazine |
| 956 | sumatriptan | chlorpromazine |
| 957 | sumatriptan | trimethobenzamide |
| 958 | sumatriptan | ondansetron |
| 959 | sumatriptan | granisetron |
| 960 | sumatriptan | hydroxyzine |
| 961 | sumatriptan | acetylleucine |
| 962 | sumatriptan | monoethanolamine |
| 963 | sumatriptan | alizapride |
| 964 | sumatriptan | azasetron |
| 965 | sumatriptan | benzquinamide |
| 966 | sumatriptan | bietanautine |
| 967 | sumatriptan | bromopride |
| 968 | sumatriptan | buclizine |
| 969 | sumatriptan | clebopride |
| 970 | sumatriptan | cyclizine |
| 971 | sumatriptan | dimenhydrinate |
| 972 | sumatriptan | diphenidol |
| 973 | sumatriptan | dolasetron |
| 974 | sumatriptan | meclizine |
| 975 | sumatriptan | methallatal |
| 976 | sumatriptan | metopimazine |
| 977 | sumatriptan | nabilone |
| 978 | sumatriptan | oxyperndyl |
| 979 | sumatriptan | pipamazine |
| 980 | sumatriptan | scopolamine |
| 981 | sumatriptan | sulpiride |
| 982 | sumatriptan | tetrahydrocannabinol |
| 983 | sumatriptan | thiethylperazine |
| 984 | sumatriptan | thioproperazine |
| 985 | sumatriptan | tropisetron |
| 986 | sumatriptan | droperidol |
| 987 | sumatriptan | haloperidol |
| 988 | sumatriptan | prochloperazine |
| 989 | sumatriptan | metoclopramide |
| 990 | sumatriptan | diphenhydramine |
| 991 | sumatriptan | *cannabis* |
| 992 | sumatriptan | midazolam |
| 993 | sumatriptan | lorazepam |
| 994 | sumatriptan | hyoscine |
| 995 | sumatriptan | dexamethasone |
| 996 | sumatriptan | emetrol |
| 997 | sumatriptan | propofol |
| 998 | zolmitriptan | promethazine |
| 999 | zolmitriptan | aprepitant |
| 1000 | zolmitriptan | dronabinol |
| 1001 | zolmitriptan | perphenazine |
| 1002 | zolmitriptan | palonosetron |
| 1003 | zolmitriptan | trimethyobenzamide |
| 1004 | zolmitriptan | metoclopromide |
| 1005 | zolmitriptan | domperidone |
| 1006 | zolmitriptan | prochlorperazine |
| 1007 | zolmitriptan | promethazine |
| 1008 | zolmitriptan | chlorpromazine |
| 1009 | zolmitriptan | trimethobenzamide |
| 1010 | zolmitriptan | ondansetron |
| 1011 | zolmitriptan | granisetron |
| 1012 | zolmitriptan | hydroxyzine |
| 1013 | zolmitriptan | acetylleucine |
| 1014 | zolmitriptan | monoethanolamine |
| 1015 | zolmitriptan | alizapride |
| 1016 | zolmitriptan | azasetron |
| 1017 | zolmitriptan | benzquinamide |
| 1018 | zolmitriptan | bietanautine |
| 1019 | zolmitriptan | bromopride |
| 1020 | zolmitriptan | buclizine |
| 1021 | zolmitriptan | clebopride |
| 1022 | zolmitriptan | cyclizine |
| 1023 | zolmitriptan | dimenhydrinate |
| 1024 | zolmitriptan | diphenidol |
| 1025 | zolmitriptan | dolasetron |
| 1026 | zolmitriptan | meclizine |
| 1027 | zolmitriptan | methallatal |
| 1028 | zolmitriptan | metopimazine |
| 1029 | zolmitriptan | nabilone |
| 1030 | zolmitriptan | oxyperndyl |
| 1031 | zolmitriptan | pipamazine |
| 1032 | zolmitriptan | scopolamine |
| 1033 | zolmitriptan | sulpiride |
| 1034 | zolmitriptan | tetrahydrocannabinol |
| 1035 | zolmitriptan | thiethylperazine |
| 1036 | zolmitriptan | thioproperazine |
| 1037 | zolmitriptan | tropisetron |
| 1038 | zolmitriptan | droperidol |
| 1039 | zolmitriptan | haloperidol |
| 1040 | zolmitriptan | prochloperazine |
| 1041 | zolmitriptan | metoclopramide |
| 1042 | zolmitriptan | diphenhydramine |
| 1043 | zolmitriptan | *cannabis* |
| 1044 | zolmitriptan | midazolam |
| 1045 | zolmitriptan | lorazepam |
| 1046 | zolmitriptan | hyoscine |
| 1047 | zolmitriptan | dexamethasone |
| 1048 | zolmitriptan | emetrol |
| 1049 | zolmitriptan | propofol |
| 1050 | eletriptan | promethazine |
| 1051 | eletriptan | aprepitant |
| 1052 | eletriptan | dronabinol |
| 1053 | eletriptan | perphenazine |
| 1054 | eletriptan | palonosetron |
| 1055 | eletriptan | trimethyobenzamide |
| 1056 | eletriptan | metoclopromide |
| 1057 | eletriptan | domperidone |
| 1058 | eletriptan | prochlorperazine |
| 1059 | eletriptan | promethazine |
| 1060 | eletriptan | chlorpromazine |
| 1061 | eletriptan | trimethobenzamide |
| 1062 | eletriptan | ondansetron |
| 1063 | eletriptan | granisetron |
| 1064 | eletriptan | hydroxyzine |
| 1065 | eletriptan | acetylleucine |
| 1066 | eletriptan | monoethanolamine |
| 1067 | eletriptan | alizapride |
| 1068 | eletriptan | azasetron |
| 1069 | eletriptan | benzquinamide |
| 1070 | eletriptan | bietanautine |
| 1071 | eletriptan | bromopride |
| 1072 | eletriptan | buclizine |
| 1073 | eletriptan | clebopride |
| 1074 | eletriptan | cyclizine |
| 1075 | eletriptan | dimenhydrinate |
| 1076 | eletriptan | diphenidol |
| 1077 | eletriptan | dolasetron |

TABLE 2-continued

Multi-drug Compositions

| Composition No. | Triptan | Antiemetic agent |
|---|---|---|
| 1078 | eletriptan | meclizine |
| 1079 | eletriptan | methallatal |
| 1080 | eletriptan | metopimazine |
| 1081 | eletriptan | nabilone |
| 1082 | eletriptan | oxyperndyl |
| 1083 | eletriptan | pipamazine |
| 1084 | eletriptan | scopolamine |
| 1085 | eletriptan | sulpiride |
| 1086 | eletriptan | tetrahydrocannabinol |
| 1087 | eletriptan | thiethylperazine |
| 1088 | eletriptan | thioproperazine |
| 1089 | eletriptan | tropisetron |
| 1090 | eletriptan | droperidol |
| 1091 | eletriptan | haloperidol |
| 1092 | eletriptan | prochloperazine |
| 1093 | eletriptan | metoclopramide |
| 1094 | eletriptan | diphenhydramine |
| 1095 | eletriptan | *cannabis* |
| 1096 | eletriptan | midazolam |
| 1097 | eletriptan | lorazepam |
| 1098 | eletriptan | hyoscine |
| 1099 | eletriptan | dexamethasone |
| 1100 | eletriptan | emetrol |
| 1101 | eletriptan | propofol |
| 1102 | frovatriptan | promethazine |
| 1103 | frovatriptan | aprepitant |
| 1104 | frovatriptan | dronabinol |
| 1105 | frovatriptan | perphenazine |
| 1106 | frovatriptan | palonosetron |
| 1107 | frovatriptan | trimethyobenzamide |
| 1108 | frovatriptan | metoclopromide |
| 1109 | frovatriptan | domperidone |
| 1110 | frovatriptan | prochlorperazine |
| 1111 | frovatriptan | promethazine |
| 1112 | frovatriptan | chlorpromazine |
| 1113 | frovatriptan | trimethobenzamide |
| 1114 | frovatriptan | ondansetron |
| 1115 | frovatriptan | granisetron |
| 1116 | frovatriptan | hydroxyzine |
| 1117 | frovatriptan | acetylleucine |
| 1118 | frovatriptan | monoethanolamine |
| 1119 | frovatriptan | alizapride |
| 1120 | frovatriptan | azasetron |
| 1121 | frovatriptan | benzquinamide |
| 1122 | frovatriptan | bietanautine |
| 1123 | frovatriptan | bromopride |
| 1124 | frovatriptan | buclizine |
| 1125 | frovatriptan | clebopride |
| 1126 | frovatriptan | cyclizine |
| 1127 | frovatriptan | dimenhydrinate |
| 1128 | frovatriptan | diphenidol |
| 1129 | frovatriptan | dolasetron |
| 1130 | frovatriptan | meclizine |
| 1131 | frovatriptan | methallatal |
| 1132 | frovatriptan | metopimazine |
| 1133 | frovatriptan | nabilone |
| 1134 | frovatriptan | oxyperndyl |
| 1135 | frovatriptan | pipamazine |
| 1136 | frovatriptan | scopolamine |
| 1137 | frovatriptan | sulpiride |
| 1138 | frovatriptan | tetrahydrocannabinol |
| 1139 | frovatriptan | thiethylperazine |
| 1140 | frovatriptan | thioproperazine |
| 1141 | frovatriptan | tropisetron |
| 1142 | frovatriptan | droperidol |
| 1143 | frovatriptan | haloperidol |
| 1144 | frovatriptan | prochloperazine |
| 1145 | frovatriptan | metoclopramide |
| 1146 | frovatriptan | diphenhydramine |
| 1147 | frovatriptan | *cannabis* |
| 1148 | frovatriptan | midazolam |
| 1149 | frovatriptan | lorazepam |
| 1150 | frovatriptan | hyoscine |
| 1151 | frovatriptan | dexamethasone |
| 1152 | frovatriptan | emetrol |
| 1153 | frovatriptan | propofol |
| 1154 | rizatriptan | promethazine |
| 1155 | rizatriptan | aprepitant |
| 1156 | rizatriptan | dronabinol |
| 1157 | rizatriptan | perphenazine |
| 1158 | rizatriptan | palonosetron |
| 1159 | rizatriptan | trimethyobenzamide |
| 1160 | rizatriptan | metoclopromide |
| 1161 | rizatriptan | domperidone |
| 1162 | rizatriptan | prochlorperazine |
| 1163 | rizatriptan | promethazine |
| 1164 | rizatriptan | chlorpromazine |
| 1165 | rizatriptan | trimethobenzamide |
| 1166 | rizatriptan | ondansetron |
| 1167 | rizatriptan | granisetron |
| 1168 | rizatriptan | hydroxyzine |
| 1169 | rizatriptan | acetylleucine |
| 1170 | rizatriptan | monoethanolamine |
| 1171 | rizatriptan | alizapride |
| 1172 | rizatriptan | azasetron |
| 1173 | rizatriptan | benzquinamide |
| 1174 | rizatriptan | bietanautine |
| 1175 | rizatriptan | bromopride |
| 1176 | rizatriptan | buclizine |
| 1177 | rizatriptan | clebopride |
| 1178 | rizatriptan | cyclizine |
| 1179 | rizatriptan | dimenhydrinate |
| 1180 | rizatriptan | diphenidol |
| 1181 | rizatriptan | dolasetron |
| 1182 | rizatriptan | meclizine |
| 1183 | rizatriptan | methallatal |
| 1184 | rizatriptan | metopimazine |
| 1185 | rizatriptan | nabilone |
| 1186 | rizatriptan | oxyperndyl |
| 1187 | rizatriptan | pipamazine |
| 1188 | rizatriptan | scopolamine |
| 1189 | rizatriptan | sulpiride |
| 1190 | rizatriptan | tetrahydrocannabinol |
| 1191 | rizatriptan | thiethylperazine |
| 1192 | rizatriptan | thioproperazine |
| 1193 | rizatriptan | tropisetron |
| 1194 | rizatriptan | droperidol |
| 1195 | rizatriptan | haloperidol |
| 1196 | rizatriptan | prochloperazine |
| 1197 | rizatriptan | metoclopramide |
| 1198 | rizatriptan | diphenhydramine |
| 1199 | rizatriptan | *cannabis* |
| 1200 | rizatriptan | midazolam |
| 1201 | rizatriptan | lorazepam |
| 1202 | rizatriptan | hyoscine |
| 1203 | rizatriptan | dexamethasone |
| 1204 | rizatriptan | emetrol |
| 1205 | rizatriptan | propofol |

As to any pharmaceutically active agent disclosed in the foregoing Table 1 or Table 2, it should be noted that any pharmaceutically acceptable salt of the pharmaceutically active agent is within the various embodiments of the present invention. Furthermore, non-limiting examples of such pharmaceutically acceptable salts are disclosed herein.

While particular embodiments described herein have been shown and described herein, such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. A solid oral pharmaceutical composition, wherein the solid oral pharmaceutical composition comprises:
   a. a first matrix, wherein the first matrix comprises an effective amount of a first pharmaceutically active agent for treating or preventing a condition in a subject in need thereof; and
   b. a second matrix, wherein the second matrix comprises an effective amount of a second pharmaceutically active agent for preventing or reducing a secondary symptom associated with the condition, and wherein the second matrix is an immediate release matrix,
   wherein the first pharmaceutically active agent comprises a serotonin receptor agonist that comprises an ergot, and wherein the ergot comprises ergotamine, methysergide, or zonisamide.

2. A solid oral pharmaceutical composition, wherein the solid oral pharmaceutical composition comprises:
   a. a first matrix, wherein the first matrix comprises an effective amount of a first pharmaceutically active agent for treating or preventing a condition in a subject in need thereof; and
   b. a second matrix, wherein the second matrix comprises an effective amount of a second pharmaceutically active agent for preventing or reducing a secondary symptom associated with the condition, and wherein the second matrix is an immediate release matrix,
   wherein the first pharmaceutically active agent comprises a serotonin receptor agonist that comprises a triptan, and wherein the triptan comprises naratriptan, almotriptan, sumatriptan, zolmitriptan, eletriptan, frovatriptan, or rizatriptan.

3. A solid oral pharmaceutical composition, wherein the solid oral pharmaceutical composition comprises:
   a. a first matrix, wherein the first matrix comprises an effective amount of a first pharmaceutically active agent for treating or preventing a condition in a subject in need thereof; and
   b. a second matrix, wherein the second matrix comprises an effective amount of a second pharmaceutically active agent for preventing or reducing a secondary symptom associated with the condition, and wherein the second matrix is an immediate release matrix,
   wherein the first pharmaceutically active agent comprises a beta blocker, and wherein the beta blocker comprises acebutolol, arotinolol, atenolol, betaxolol, bisoprolol, butoxamine, carvedilol, carteolol, esmolol, carteolol, carvedilol, labetalol, levobunolol, mepindolol, metoprolol, nebivolol, nadolol, oxprenolol, penbutolol, propranolol, pindolol, sotalol, or timolol.

4. A solid oral pharmaceutical composition, wherein the solid oral pharmaceutical composition comprises:
   a. a first matrix, wherein the first matrix comprises an effective amount of a first pharmaceutically active agent for treating or preventing a condition in a subject in need thereof; and
   b. a second matrix, wherein the second matrix comprises an effective amount of a second pharmaceutically active agent for preventing or reducing a secondary symptom associated with the condition, and wherein the second matrix is an immediate release matrix,
   wherein the first pharmaceutically active agent comprises a vasoconstrictor, and wherein the vasoconstrictor comprises isometheptene mucate, caffeine, pseudoephedrine, ergine, methylphenidate, or psilocybin.

5. A solid oral pharmaceutical composition, wherein the solid oral pharmaceutical composition comprises:
   a. a first matrix, wherein the first matrix comprises an effective amount of a first pharmaceutically active agent for treating or preventing a condition in a subject in need thereof; and
   b. a second matrix, wherein the second matrix comprises an effective amount of a second pharmaceutically active agent for preventing or reducing a secondary symptom associated with the condition, and wherein the second matrix is an immediate release matrix,
   wherein the first pharmaceutically active agent comprises a anti-platelet agent, and wherein the anti-platelet agent comprises acetylsalycyclic acid, clopidogrel, ticlopidine, cilostazol, abciximab, eptifibatide, tirofiban defibrotide, or dipyridamole.

6. A solid oral pharmaceutical composition, wherein the solid oral pharmaceutical composition comprises:
   a. a first matrix, wherein the first matrix comprises an effective amount of a first pharmaceutically active agent for treating or preventing a condition in a subject in need thereof; and
   b. a second matrix, wherein the second matrix comprises an effective amount of a second pharmaceutically active agent for preventing or reducing a secondary symptom associated with the condition, and wherein the second matrix is an immediate release matrix,
   wherein the first pharmaceutically active agent comprises an anti-covulsant, and wherein the anti-convulsant comprises topiramate, divaprex, pehnobarbital, methlyphenobarbital, metharbital, barbexaclone, stiripentol, clobazam, clonazepam, clorazepate, diazepam, midazolam, lorazepam, nitrazepam, temazepam, nimetazepam, potassium bromide, felbamate, carbamazepine, oxcarbazepine, vigabatrin, progabide, tiagabine, gabapentin, prgabalin, ethotoin, phenytoin, mephenytoin, fosphenytoin, paramethadione, trimethadione, ethadione, beclamide, primidone, brivaracetam, levetiracetam, seletracetam, ethsuximide, phesuximide, mesuximide, acetazolamide, sulthiame, methazolamide, zonisamide, lamotrigine, pheneturide, phenacemide, valpromide, or valnoctamide.

7. A solid oral pharmaceutical composition, wherein the solid oral pharmaceutical composition comprises:
   a. a first matrix, wherein the first matrix comprises an effective amount of a first pharmaceutically active agent for treating or preventing a condition in a subject in need thereof; and
   b. a second matrix, wherein the second matrix comprises an effective amount of a second pharmaceutically active agent for preventing or reducing a secondary symptom associated with the condition, and wherein the second matrix is an immediate release matrix,
   wherein the first pharmaceutically active agent comprises a calcitonin-gene-related peptide (CGRP) receptor antagonist, and wherein the CGRP receptor antagonist comprises MK-0974, CGRP8-37, BIBN 4096 BS, quinine, nitrobenzamide, 4-oxobutanamide, a cyclopropane derivative, or a benzimidazolinyl piperidine.

* * * * *